(12) United States Patent
Carpenter et al.

(10) Patent No.: US 7,285,557 B2
(45) Date of Patent: Oct. 23, 2007

(54) PYRIMIDINONES AS MELANIN CONCENTRATING HORMONE RECEPTOR 1

(75) Inventors: Andrew J Carpenter, Durham, NC (US); Joel P Cooper, Durham, NC (US); Anthony L Handlon, Durham, NC (US); Donald L Hertzog, Durham, NC (US); Clifton E Hyman, Durham, NC (US); Yu C Guo, Durham, NC (US); Jason D Speake, Durham, NC (US); David Richard Witty, Harlow (GB)

(73) Assignee: SmithKline Beecham P.L.C., Brentford, Middlesex (GB)

(*) Notice: Subject to any disclaimer, the term of this patent is extended or adjusted under 35 U.S.C. 154(b) by 295 days.

(21) Appl. No.: 10/492,641

(22) PCT Filed: Oct. 15, 2002

(86) PCT No.: PCT/US02/32739

§ 371 (c)(1),
(2), (4) Date: Apr. 14, 2004

(87) PCT Pub. No.: WO03/033476

PCT Pub. Date: Apr. 24, 2003

(65) Prior Publication Data

US 2004/0220404 A1    Nov. 4, 2004

(30) Foreign Application Priority Data

Oct. 15, 2001 (GB) ................... 0124627.1

(51) Int. Cl.
| A61K 31/519 | (2006.01) |
| C07D 495/04 | (2006.01) |
| C07D 333/78 | (2006.01) |
| A61K 31/55 | (2006.01) |
| A61K 31/5377 | (2006.01) |
| A61K 31/517 | (2006.01) |
| C07D 401/12 | (2006.01) |
| C07D 403/12 | (2006.01) |
| C07D 239/82 | (2006.01) |
| C07D 498/02 | (2006.01) |

(52) U.S. Cl. ................ 514/260.1; 514/217.06; 514/234.5; 514/266.2; 514/266.22; 514/266.31; 544/116; 544/278; 544/287; 540/600

(58) Field of Classification Search ............ 514/260.1; 544/278
See application file for complete search history.

(56) References Cited

U.S. PATENT DOCUMENTS

| 5,202,328 A * | 4/1993 | de Laszlo et al. ........ 514/263.3 |
| 5,962,457 A * | 10/1999 | Chenard et al. ......... 514/260.1 |
| 6,469,166 B2 * | 10/2002 | Webb et al. ................ 544/278 |
| 6,921,764 B2 * | 7/2005 | Chenard et al. ......... 514/260.1 |
| 2007/0093509 A1 * | 4/2007 | Washburn et al. ....... 514/260.1 |

FOREIGN PATENT DOCUMENTS

| WO | WO97/41097 | 11/1997 |
| WO | WO 01/21577 | 3/2001 |

OTHER PUBLICATIONS

Saxena S et al., *Anti-Inflammatory Quinazolinones*, Indian Journal of Pharmaceutical Sciences 53(2): 48-52 (Mar. 1991).
Database Caplus Online, Chemical Abstrats Service, Coloumbus Ohio, US, Database accession No. 1991:122049 XP002233183 abstract & PL 137 227 B (Uniwersytet Lodzki, Lodz (Polska) Mar. 31, 1987 table.

* cited by examiner

*Primary Examiner*—Emily Bernhardt
*Assistant Examiner*—Tamthom N Truong
(74) *Attorney, Agent, or Firm*—Bonnie L. Deppenbrock

(57) ABSTRACT

A compound of formula (Ia) comprising a pharmaceutically acceptable salt or solvate thereof, formulations, processes of preparing, and methods of administering to mammals are provided

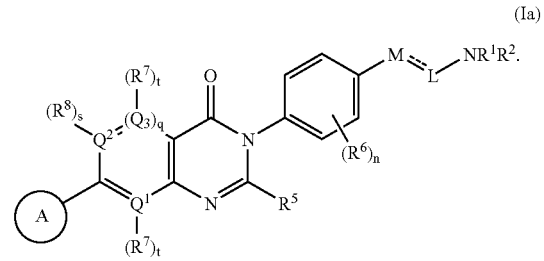

(Ia)

25 Claims, No Drawings

PYRIMIDINONES AS MELANIN CONCENTRATING HORMONE RECEPTOR 1

This application is filed pursuant to 35 U.S.C. § 371 as a United States National Phase Application of International Application No. PCT/US02/32739 filed Oct. 15, 2002, which claims priority from GB 0124627.1 filed Oct. 15, 2001.

This invention relates to novel pyrimidinones which are antagonists at the melanin-concentrating hormone receptor 1 (MCHR1), also referred to as 11CBy, to pharmaceutical compositions containing them, to processes for their preparation, and to their use in therapy.

Obesity is a medical condition that is reaching epidemic proportions among humans in a number of countries throughout the world. It is a condition that is also associated with or induces other diseases or conditions that disrupt life activities and lifestyles. Obesity is recognized as a serious risk factor for other diseases and conditions such as diabetes, hypertension, and arteriosclerosis. It is also known that increased body weight due to obesity can place a burden on joints, such as knee joints, causing arthritis, pain, and stiffness.

Because overeating and obesity have become such a problem in the general population, many individuals are now interested in losing weight, reducing weight, and/or maintaining a healthy body weight and desirable lifestyle.

WO01/21577 (Takeda) relates to a compound of the formula $$Ar^1-X-Ar-Y-N\begin{matrix}R^1\\R^2\end{matrix}$$

wherein $Ar^1$ is a cyclic group which may have substituents, X is a spacer having a main chain of 1 to 6 atoms, Y is a bond or a spacer having a main chain of 1 to 6 atoms, Ar is a monocyclic aromatic ring which may be condensed with a 4 to 8 membered non-aromatic ring, and may have further substituents; $R^1$ and $R^2$ are independently hydrogen or a hydrocarbon group which may have substituents; $R^1$ and $R^2$ together with the adjacent nitrogen atom may form a nitrogen containing hetero ring which may have substituents; $R^2$ may form a spiro ring together with Ar; or $R^2$ together with the adjacent nitrogen atom may form a nitrogen containing hetero ring which may have substituents; or a salt thereof; and which compounds are antagonists of a melanin-concentrating hormone. Such compounds are suggested as being useful for preventing or treating obesity.

In particular, it is known that melanin-concentrating hormone ("MCH") originates in the hypothalamus and has orexigenic action (see *Nature*, Vol. 396, p. 670, (1998), for example). There is an on-going need for the development of a melanin-concentrating hormone antagonist useful in the treatment of obesity and other associated or related diseases and conditions.

Accordingly, we have now found a novel group of pyrimidinones that exhibit a useful profile of activity as antagonists of the melanin-concentrating hormone receptor (MCHR1) disclosed in Nature, Vol. 400, p. 261-265 (1999).

SUMMARY OF THE INVENTION

The present invention provides a compound of formula (Ia) comprising:

(Ia)

a pharmaceutically acceptable salt, solvate, or physiologically functional derivative thereof, wherein:

Ⓐ is aryl or heteroaryl, optionally substituted by one to four $C_{1-6}$ straight or branched alkyl, alkenyl, halo, amino, alkylamino, dialkylamino, hydroxy, $C_{1-6}$ alkoxy, cyano, or alkylthio groups;

a dashed line represents an optional double bond;

q, r, s, and t are each independently 0 or 1;

when q is 1, the dashed line is a double bond;

$Q^1$ and $Q^3$ are each independently C or N;

when q is 0 then $Q^2$ is N, S, or O;

when q is 1, then $Q^2$ is C or N; when q is 1 and $Q^2$ is N, then s is 0;

when $Q^2$ is S or O, s is 0;

when q is 1 and $Q^2$ is C or when q is 0 and $Q^2$ is N, then $R^8$ is selected from hydrogen, $C_{1-6}$ straight or branched alkyl, $C_{3-6}$ cycloalkyl, $C_{1-6}$ alkoxy, amino, alkylamino, dialkylamino, hydroxy, cyano, alkylthio, and halo;

when $Q^1$ or $Q^3$ is C, then each corresponding $R^7$ is independently selected from the group consisting of hydrogen, $C_{1-6}$ straight or branched alkyl, $C_{3-6}$ cycloalkyl, $C_{1-6}$ alkoxy, amino, alkylamino, dialkylamino, hydroxy, cyano, alkylthio, and halo;

when $Q^1$ is N, r is 0;

when $Q^3$ is N, t is 0;

$R^5$ is selected from the group consisting of hydrogen, $C_{1-6}$ straight or branched alkyl, $C_{3-6}$ cycloalkyl, and $C_{1-3}$ alkylthio;

each $R^6$ is selected from the group consisting of hydrogen, $C_{1-6}$ straight or branched alkyl, $C_{1-6}$ alkoxy, trihaloalkyl, trihaloalkoxy, amino, alkylamino, dialkylamino, hydroxy, cyano, acetyl, alkylthio, and halo; and n is 1 to 4;

M is selected from the group consisting of O, S, $S(O)_2$, $S(O)_2NR$, N—R, C(O), $C(R)_2$, N—C(O)R, and N—$S(O)_2R$, wherein R is selected from the group consisting of hydrogen, phenyl, heteroaryl, $C_{1-6}$ straight or branched alkyl, and $C_{3-6}$ cycloalkyl;

L is $C_{2-3}$ alkyl, $C_{2-3}$ alkenyl, or —$C(O)(CH_2)$—;

(i) $R^1$ and $R^2$ each independently are selected from the group consisting of hydrogen, $C_{1-6}$ straight or branched alkyl, $C_{3-6}$ cycloalkyl, and a 5- or 6-membered heterocycle wherein said alkyl, said cycloalkyl and said heterocycle are optionally substituted by phenyl, one to four $C_{1-3}$ alkyl, hydroxy, oxo (i.e., =O), alkoxy or halo;

or (ii) $R^1$ and $R^2$ may be selected from the group consisting of aryl and a 5- or 6-membered heteroaryl containing 1, 2, or 3 heteroatoms selected from N, O, and S, wherein said aryl and said heteroaryl are optionally substituted 1, 2, or 3 times with a substituent selected from halo, $C_{1-6}$ straight or branched alkyl, $C_{3-6}$ cycloalkyl, $C_{1-6}$ alkenyl, $C_{3-6}$ cycloalkenyl, hydroxy, $C_{1-6}$ alkoxy, oxo (i.e., =O), amino, $C_{1-6}$alkylamino, $C_{1-6}$ dialkylamino, $C_{1-6}$ alkylthio, $C_{1-6}$ alkylsulfinyl, and phenyl;

or (iii) $R^1$ and $R^2$ together with the nitrogen atom to which they are bonded form a 4-8 membered heterocyclic ring or a 7-11 membered bicyclic heterocyclic ring, each of said 4-8 membered heterocyclic ring and said 7-11 membered bicyclic heterocyclic ring contain 1, 2 or 3 heteroatoms selected from the group consisting of N, O, and S, and wherein either said heterocyclic ring or said bicyclic heterocyclic ring may be optionally substituted by phenyl, one to four $C_{1-3}$ alkyl, hydroxy, $C_{1-3}$ alkoxy, oxo (i.e., =O), or halo;

or (iv) $R^1$ and $R^2$ may be independently linked either to the group L or linked to the group M when M is selected from the group consisting of $S(O)_2NR$, N—R, $C(R)_2$, N—C(O)R, and N—$S(O)_2R$, and wherein R is $C_{1-6}$ straight or branched alkyl, to form a 3-7 membered cyclic group which may be optionally substituted by phenyl, one to four $C_{1-3}$ alkyl, hydroxy, alkoxy, oxo (i.e., =O), or halo.

In another aspect of the invention, there is provided a pharmaceutical composition for use in the treatment, prophylaxis or both of one or more conditions or indications set forth herein comprising a compound of formula (Ia), or a physiologically acceptable salt, solvate, or physiologically functional derivative thereof, and a pharmaceutically acceptable carrier.

In a further embodiment of the invention, there are provided processes for the preparation a compound of formula (Ia).

DETAILED DESCRIPTION OF THE INVENTION

As used herein, "a compound of the invention" or "a compound of formula (Ia)" means a compound of formula (Ia) or a pharmaceutically acceptable salt, solvate, of physiologically functional derivative (such as, e.g. a prodrug), thereof.

As used herein, unless otherwise specified, the term "alkyl" and "alkylene" refer to straight or branched hydrocarbon chains containing 1 to 6 carbon atoms. Examples of "alkyl" as used herein include, but are not limited to, methyl, ethyl, n-propyl, n-butyl, n-pentyl, isobutyl, isopropyl, tert-butyl, and hexyl. Examples of "alkylene" as used herein include, but are not limited to, methylene, ethylene, propylene, butylene, and isobutylene. "Alkyl" also includes substituted alkyl. The alkyl groups may optionally be substituted with hydroxy, alkoxy, halo, amino, thio, and cyano. Halo, alkoxy, and hydroxy are particularly preferred.

As used herein, unless otherwise specified, the term "cycloalkyl" refers to a non-aromatic carbocyclic ring having from 3 to 8 carbon atoms (unless otherwise specified) and no carbon-carbon double bonds. "Cycloalkyl" includes by way of example cyclopropyl, cyclobutyl, cyclopentyl, cyclohexyl, cycloheptyl, and cyclooctyl. "Cycloalkyl" also includes substituted cycloalkyl. The cycloalkyl may be optionally substituted with substituents selected from the group consisting of hydroxy, cyano, halo, alkoxy, and alkyl. Halo, hydroxy, and alkoxy are preferred.

As used herein, unless otherwise specified, the term "alkenyl" refers to straight or branched hydrocarbon chains containing 2 to 8 carbon atoms and at least one and up to three carbon-carbon double bonds. Examples of "alkenyl" as used herein include, but are not limited to, ethenyl and propenyl. "Alkenyl" also includes substituted alkenyl. The alkenyl groups may be optionally substituted with alkyl, halo, hydroxy, alkoxy, and cyano. Halo, hydroxy, and alkoxy are preferred.

As used herein, unless otherwise specified, the term "cycloalkenyl" refers to a non-aromatic carbocyclic ring having from 3 to 8 carbon atoms (unless otherwise specified) and up to 3 carbon-carbon double bonds. "Cycloalkenyl" includes by way of example, cyclobutenyl, cyclopentenyl, and cyclohexenyl. "Cycloalkenyl" also includes substituted cycloalkenyl. The ring may be optionally substituted with at least one substituent selected from the group consisting of cyano, halo, hydroxy, $NH_2$, —$N_3$, —CN, —O—$C_{1-3}$alkyl, —NH($C_{1-3}$alkyl), —N($C_{1-3}$alkyl)$_2$ and $C_{1-3}$alkyl (including haloalkyl).

As used herein, the terms "halo" or "halogen" refer to fluorine, chlorine, bromine, and iodine. Preferred among these are chlorine (or "chloro") and fluorine (or "fluoro").

Unless otherwise specified, the term, "aryl" refers to monocyclic carbocyclic groups and fused bicyclic carbocylic groups having from 6 to 12 carbon atoms and having at least one aromatic ring. Examples of particular aryl groups include but are not limited to phenyl and naphthyl. "Aryl" also includes substituted aryl, especially substituted phenyl. Aryl rings may be optionally substituted with substituents selected from the group consisting of halo, alkyl (including haloalkyl), alkenyl, cycloalkyl, cycloalkenyl, alkoxy, amino, hydroxy, hydroxyalkyl, aminoalkyl, carboxy, carboxamide, sulfonamide, heteroaryl (abbreviated as "Het"), amidine, cyano, nitro, and azido. Preferred aryl groups according to the invention include but are not limited to phenyl and substituted phenyl. Preferred substituted phenyl is a phenyl containing one or more halo groups, particularly chloro and fluoro groups.

The term "heterocyclic", unless otherwise specified, refers to monocyclic saturated or unsaturated non-aromatic groups and fused bicyclic non-aromatic groups, having the specified number of members (e.g., carbon and heteroatoms N and/or O and/or S) in a single ring and containing 1, 2, 3, or 4 heteroatoms selected from N, O and S. Examples of particular heterocyclic groups include but are not limited to tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiopyran, tetrahydrothiophene, and the like. "Heterocyclic" also includes substituted heterocyclic. The heterocyclic group may be optionally substituted with substituents selected from the group consisting of halo, alkyl (including haloalkyls), alkenyl, cycloalkyl, cycloalkenyl, perfluoroalkyl, alkoxy, amino, hydroxy, alkylhydroxy, alkylamine, carboxy, carboxamide, sulfonamide, Het, amidine, cyano, nitro, and azido. Preferred heterocyclic groups according to the invention include, but are not limited to, substituted and unsubstituted tetrahydrofuran, pyrrolidine, piperidine, morpholine, thiomorpholine, and piperazine. Piperidine, morpholine, piperazine, and pyrrolidine are particularly preferred, with pyrrolidine being most preferred.

The term "heteroaryl", unless otherwise specified, refers to aromatic monocyclic groups and aromatic fused bicyclic groups having the specified number of members (e.g., carbon and heteroatoms N and/or O and/or S) and containing 1, 2, 3, or 4 heteroatoms selected from N, O, and S. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. "Heteroaryl" also includes substituted heteroaryl. The heteroaryl group may be optionally substituted with substituents selected from the group consisting of halo, alkyl (including perhaloalkyl, e.g., perfluoroalkyl), alkenyl, cycloalkyl, cycloalkenyl, alkoxy, amino, hydroxy, alkylhydroxy, alkylamine, carboxy, carboxamide, sulfonamide, Het, amidine, cyano, nitro, and azido. Preferred heteroaryl groups according to the invention include, but are not limited to, substituted an unsubstituted pyridine, furan, thiophene, pyrrole, imidazole, oxadiazole, pyrazole, oxazole, thiazole, and pyrimidine. Pyridine, oxadiazole, and thiazole are most preferred.

As used herein, the term "optionally" means that the subsequently described event(s) may or may not occur, and includes both event(s) that occur and events that do not occur.

Formula (Ia) of the invention is set forth in detail as follows.

Ⓐ is aryl or heteroaryl, optionally substituted by one to four $C_{1-6}$ straight or branched alkyl, alkenyl, halo, amino, alkylamino, dialkylamino, hydroxy, $C_{1-6}$ alkoxy, cyano or alkylthio groups. Preferred among these substituted groups are halo, $C_{1-3}$ alkyl, and $C_{1-3}$ alkoxy. Most preferred are fluoro, chloro, and methoxy. In a preferred embodiment said aryl is substituted with a halo group, q is 0, $Q^1$ is carbon, and $R^7$ is hydrogen or halo. For example, aryl is 4-chlorophenyl and $R^5$ and $R^7$ are each hydrogen.

In the formula, a dashed line represents an optional double bond and q, r, s, and t are each independently 0 or 1.

In formula (Ia), q is 0 or 1. When q is 1 the dashed line between $Q^2$ and $Q^3$ in formula (Ia) is a double bond. When q is 0 there is no dashed line, and the bond between $Q^2$ and $Q^3$ is a single bond. When q is 0 then Q2 is N, S, or O. And when q is 1, $Q^2$ is C or N. When q is 1 and $Q^2$ is N, then s is 0 and there is no $R^8$ substituent.

$Q^1$ and $Q^3$ are each independently carbon (C) or nitrogen (N). In one embodiment, $Q^1$, $Q^2$, and $Q^3$ are carbon and q, r, s, and t are 1. In another embodiment, $Q^1$ is carbon, $Q^2$ is sulfur, q and s are 0, and r is 1.

In the formula, r and t are each independently 0 or 1. When r and t are each independently 0, then there is no $R^7$ substituent. When r and t are each independently 1, $Q^1$ and $Q^3$ are each independently bonded by the group $R^7$. Each $R^7$ is the same or different and is independently selected from hydrogen, $C_{1-6}$ straight or branched alkyl, $C_{3-6}$ cycloalkyl, $C_{1-6}$ alkoxy, amino, alkylamino, dialkylamio, hydroxy, cyano, alkylthio, and halo.

In formula (Ia), s is 0 or 1. When $Q^2$ is S or O, then s is 0 and there is no $R^8$ group. When $Q^2$ is C, then s is 1 and $R^8$ is selected from the group consisting of hydrogen, $C_{1-6}$ straight or branched alkyl, $C_{3-6}$ cycloalkyl, $C_{1-6}$ alkoxy, amino, alkylamino, dialkylamino, hydroxy, cyano, alkylthio, and halo. When $Q^2$ is C, preferably $R^8$ is hydrogen or a $C_{1-3}$ alkyl; most preferably $R^8$ is hydrogen or methyl.

When $Q^2$ is N, and s is 1, $R^8$ is selected from the group consisting of hydrogen, $C_{1-6}$ straight or branched alkyl, $C_{3-6}$ cycloalkyl, $C_{1-6}$ alkoxy, amino, alkylamino, dialkyl amino, hydroxy, cyano, alkylthio, and halo. When $Q^2$ is N, preferably $R^8$ is hydrogen or a $C_{1-3}$ alkyl; most preferably $R^8$ is hydrogen or methyl.

When either or both $Q^1$ and $Q^3$ are C, then $R^7$ is selected from the group consisting of hydrogen, $C_{1-6}$ straight or branched alkyl, $C_{3-6}$ cycloalkyl, $C_{1-6}$ alkoxy, amino, alkylamino, dialkylamino, hydroxy, cyano, alkylthio, and halo.

Preferably, when either or both $Q^1$ and $Q^3$ are C, $R^7$ is hydrogen or $C_{1-3}$ alkyl; most preferably $R^7$ is hydrogen or methyl.

In formula (Ia), $R^5$ is selected from the group consisting of hydrogen, $C_{1-6}$ straight or branched alkyl, and $C_{3-6}$ cycloalkyl. Preferably, $R^5$ is hydrogen or a $C_{1-3}$ alkyl; most preferably $R^5$ is hydrogen or methyl.

In formula (Ia), $R^6$ is selected from the group consisting of hydrogen, $C_{1-6}$ straight or branched alkyl, $C_{1-6}$ alkoxy, trihaloalkyl, trihaloalkoxy, amino, alkylamino, dialkylamino, hydroxy, cyano, acetyl, alkylthio, and halo and n is 1 to 4. Preferably $R^6$ is selected from the group consisting of hydrogen, $C_{1-3}$ alkyl, $C_{1-3}$ alkoxy, and halo, and n is 1 or 2. Most preferably $R^6$ is selected from the group consisting of hydrogen and methoxy, and n is 1.

In the formula (Ia), M is selected from the group consisting of O, S, S(O)$_2$, S(O)$_2$NR, N—R, C(O), C(R)$_2$, N—C(O)R, and N—S(O)$_2$R, wherein R is selected from the group consisting of hydrogen, phenyl, heteroaryl, $C_{1-6}$ straight or branched alkyl, and $C_{3-6}$ cycloalkyl. Preferably M is selected from the group consisting of O, S, S(O)$_2$NR, N—R, N—C(O)R, and N—S(O)$_2$R; most preferably M is selected from the group consisting of O, N—R, and N—C(O)R. Preferably R is selected from the group consisting of hydrogen, phenyl, $C_{1-6}$ straight or branched alkyl, and $C_{3-6}$ cycloalkyl; most preferably R is selected from the group consisting of hydrogen, $C_{1-6}$ straight or branched alkyl, and $C_{3-6}$ cycloalkyl.

L of formula (Ia) is $C_{2-3}$ alkyl, $C_{2-3}$ alkenyl, or C(O)(CH$_2$)—. Preferably, L is $C_{2-3}$ alkyl or $C_{2-3}$ alkenyl; most preferably L is $C_{2-3}$ alkyl. C(O)(CH$_2$)— is only present when M is N.

In (i) $R^1$ and $R^2$ in formula (Ia) are each independently selected from the group consisting of hydrogen, $C_{1-6}$ straight or branched alkyl, $C_{3-6}$ cycloalkyl, phenyl, and 5- or 6-membered heterocycle, wherein said alkyl, said cycloalkyl, and said heterocycle are optionally substituted by phenyl, one to four $C_{1-3}$ alkyl, hydroxy, oxo, alkoxy, or halo. Preferably, $R^1$ and $R^2$ are selected from the group consisting of hydrogen, $C_{1-6}$ straight or branched alkyl, and $C_{3-6}$ cycloalkyl. Most preferably, $R^1$ and $R^2$ are selected from the group consisting of hydrogen, $C_{1-3}$ alkyl, and $C_{3-6}$ cycloalkyl.

Or, in (ii) $R^1$ and $R^2$ may be selected from the group consisting of aryl and a 5- or 6-membered heteroaryl containing 1, 2, or 3 heteroatoms selected from N, O, and S, wherein said aryl and said heteroaryl are optionally substituted 1, 2, or 3 times with a substituent selected from the group consisting of halo, $C_{1-6}$ straight or branched alkyl, $C_{3-6}$ cycloalkyl, $C_{1-6}$ alkenyl, $C_{3-6}$ cycloalkenyl, hydroxy, $C_{1-6}$ alkoxy, oxo, amino, $C_{1-6}$ alkylamino, $C_{1-6}$ dialkylamino, $C_{1-6}$ alkylthio, $C_{1-6}$ alkylsulfinyl, and phenyl. Preferably, when either $R^1$ or $R^2$ is aryl or heteroaryl, the other remaining $R^1$ or $R^2$ is hydrogen, $C_{1-6}$ alkyl, or a $C_{3-6}$ cycloalkyl.

Additionally, in (iii) $R^1$ and $R^2$ together with the nitrogen atom to which they are bonded can form a 4-8 membered heterocyclic ring or a 7-11 membered bicyclic heterocyclic ring. The 4-8 membered heterocyclic ring and/or the 7-11 membered bicyclic heterocyclic ring may contain 1, 2, or 3 heteroatoms selected from the group consisting of N, O, and S. And either the heterocyclic ring or the bicyclic heterocyclic ring may be optionally substituted by phenyl, one to four $C_{1-3}$ alkyl, hydroxy, $C_{1-3}$ alkoxy, oxo, or halo. Here neither group $R^1$ or $R^2$ is linked back to M or L. Preferably, $R^1$ and $R^2$ together form a 5- or 6-membered heterocyclic ring or an 8- to 11-membered bicylic heterocyclic ring, having 1 or 2 heteroatoms selected from the group N, O, and S wherein said heterocyclic ring and said bicyclic heterocyclic ring may be optionally substituted up to two times with a substituent selected from the group consisting of oxo and halo.

Also additionally, in (iv) $R^1$ and $R^2$ may be independently linked either to the group L or linked to the group M when M is selected from the group consisting of $S(O)_2NR$, N—R, $C(R)_2$, N—C(O)R, and N—$S(O)_2R$, (where R is $C_{1-6}$ straight or branched alkyl), to form a 3-7 membered cyclic group. The 3-7 membered cyclic group may be optionally substituted by phenyl, one to four $C_{1-3}$ alkyl, hydroxy, alkoxy, oxo, or halo. Preferably, either or both $R^1$ and $R^2$ are linked to M when M is selected from the group consisting of $S(O)_2NR$, N—R, $C(R)_2$, N—C(O)R, and N—$S(O)_2R$, (wherein R is $C_{1-6}$ straight or branched alkyl), to form a 4-7 membered ring. Most preferably a 5-7 membered ring is formed. The 5-7 membered ring or cyclic group may be optionally substituted by phenyl, one to four $C_{1-3}$ alkyl, hydroxy, alkoxy, oxo, or halo. Here, either the $R^1$ group or the $R^2$ group, or both $R^1$ and $R^2$ are linked back to the group L. Preferably, only one of the groups $R^1$ and $R^2$ are linked back to the group L.

In one embodiment when L is $C_2$-$C_3$ alkyl or $C_2$-$C_3$ alkenyl, in (i), $R^1$ and $R^2$ are selected from the group consisting of hydrogen, $C_1$-$C_3$ straight or branched alkyl, $C_3$-$C_6$ cycloalkyl substituted with a substituent selected from the group consisting of halo, alkyl, hydroxy, oxo, and alkoxy. Or, when L is $C_2$-$C_3$ alkyl or $C_2$-$C_3$ alkenyl, in (iii), $R^1$ and $R^2$ together with the nitrogen atom to which they are bonded form a 4-6 membered heterocyclic ring wherein said heterocyclic ring is optionally substituted with a substituent selected from the group consisting of one to four $C_1$-$C_3$ alkyl, hydroxy, alkoxy, oxo, and halo.

In another embodiment, when L is a $C_2$-$C_3$ alkyl, in (i), $R^1$ and $R^2$ are each independently selected from the group consisting of hydrogen and $C_3$-$C_6$ cycloalkyl substituted with a substituent selected from the group consisting of oxo and halo. Or, when L is a $C_2$-$C_3$ alkyl, in (iii), $R^1$ and $R^2$ together with the nitrogen atom to which they are bonded form a 5- or 6-membered heterocyclic that is optionally substituted with a substituent selected from the group consisting of one to two oxo and halo. In a further embodiment L is $CH_2CH_2$ and, in (iii), $R^1$ and $R^2$ together with the nitrogen atom to which they are bonded form a pyrrolidine ring substituted at the 3-position with a fluorine atom.

In still another embodiment M is O, N—R or N—C(O)R, where R is hydrogen or $C_1$-$C_6$ straight or branched alkyl, and $R^6$ is selected from the group consisting of hydrogen, $C_1$-$C_6$ straight or branched alkyl, $C_1$-$C_3$ alkoxy, trihaloalkyl, trihaloalkoxy, cyano, and halo. Preferably, M is O or N—R where R is hydrogen and $R^6$ is selected from the group consisting of hydrogen, $C_1$-$C_2$ straight or branched alkyl, $C_1$-$C_2$ alkoxy, or halo. Most preferably in this embodiment, M is O and $R^6$ is methoxy.

Most preferred compounds according to this invention are selected from the group consisting of 6-(4-chlorophenyl)-3-{3-methoxy-4-[2-(3-oxopyrrolidin-1-yl)ethoxy]phenyl}thieno[3,2-d]pyrimidin-4(3H)-one and 6-(4-chlorophenyl)-3-{4-[2-(3-fluoropyrrolidin-1-yl)ethoxy]-3-methoxyphenyl}thieno[3,2-d]pyrimidin-4(3H)-one.

Certain compounds of formula (Ia) may exist in stereoisomeric forms (e.g., they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (Ia) as mixtures with isomers thereof in which one or more chiral centers are inverted. Certain compounds of formula (Ia) may be prepared as regioisomers. The present invention covers both the mixture of regioisomers as well as individual compounds. Likewise, it is understood that compounds of formula (Ia) may exist in tautomeric forms other than that shown in the formula and these are also included within the scope of the present invention.

It is to be understood that the present invention includes all combinations and subsets of the particular groups defined hereinabove.

Specific compounds of formula (Ia) include but are not limited those set forth in Table I below and/or those prepared examples herein.

| Example No. | Structure | Name |
|---|---|---|
| H1 | 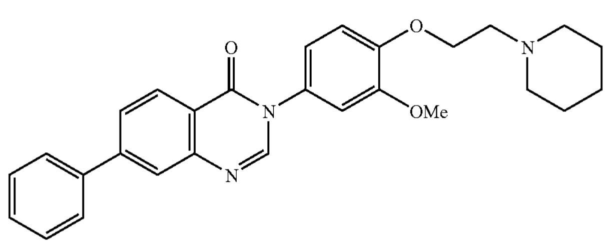 | 3-{3-methoxy-4-[2-(1-piperidinyl)ethoxy]phenyl}-7-phenyl-4(3H)-quinazolinone |
| H2 | 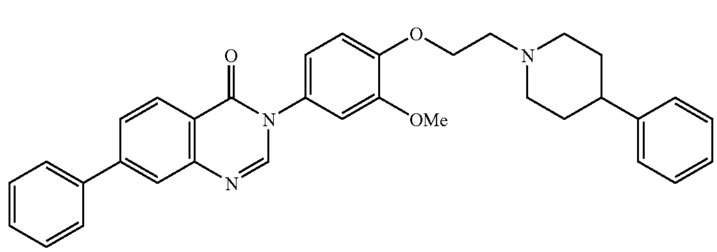 | 3-{3-methoxy-4-[2-(4-phenyl-1-piperidinyl)ethoxy]phenyl}-7-phenyl-4(3H)-quinazolinone |

-continued

| Example No. | Structure | Name |
|---|---|---|
| H3 | 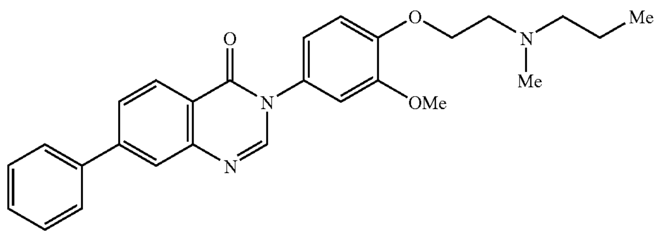 | 3-(3-methoxy-4-{2-[methyl(propyl)amino]ethoxy}-phenyl)-7-phenyl-4(3H)-quinazolinone |
| H4 | 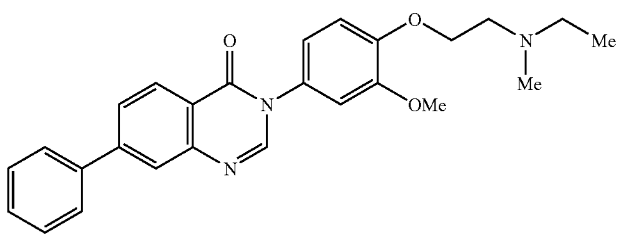 | 3-(4-{2-[ethyl(methyl)amino]-ethoxy}-3-methoxyphenyl)-7-phenyl-4(3H)-quinazolinone |
| H5 | 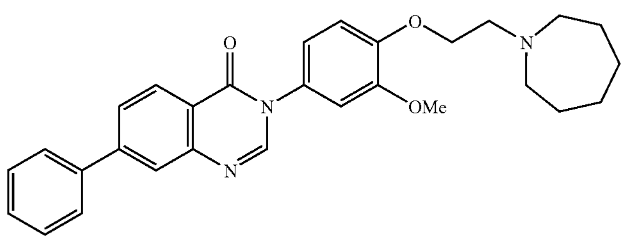 | 3-{4-[2-(1-azepanyl)ethoxy]-3-methoxyphenyl}-7-phenyl-4(3H)-quinazolinone |
| H6 | 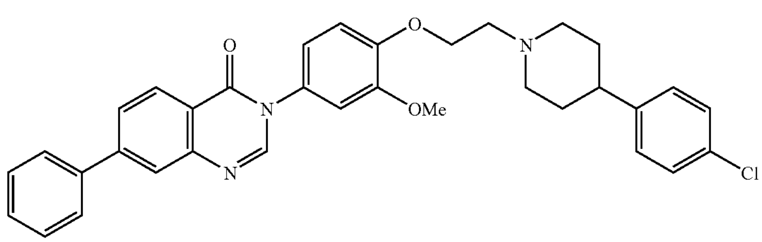 | 3-(4-{2-[4-(4-chlorophenyl)-1-piperidinyl]ethoxy}-3-methoxyphenyl)-7-phenyl-4(3H)-quinazolinone |
| H7 | 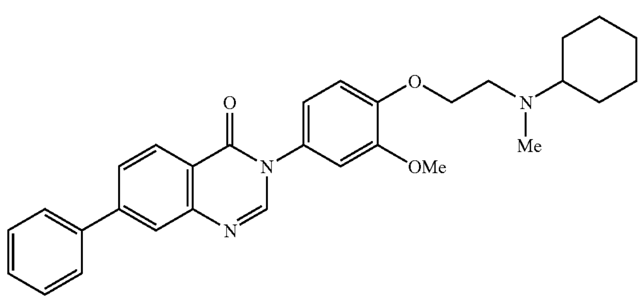 | 3-(4-{2-[cyclohexyl(methyl)-amino]ethoxy}-3-methoxy-phenyl)-7-phenyl-4(3H)-quinazolinone |
| H8 | 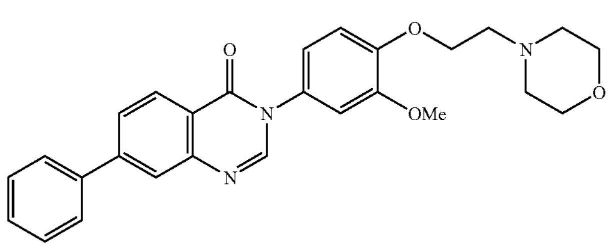 | 3-{3-methoxy-4-[2-(4-morpholinyl)ethoxy]phenyl}-7-phenyl-4(3H)-quinazolinone |

-continued

| Example No. | Structure | Name |
|---|---|---|
| H9 | 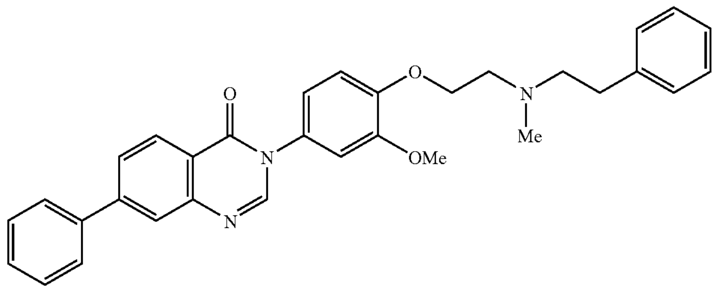 | 3-(3-methoxy-4-{2-[methyl(2-phenylethyl)amino]ethoxy}-phenyl)-7-phenyl-4(3H)-quinazolinone |
| H10 | 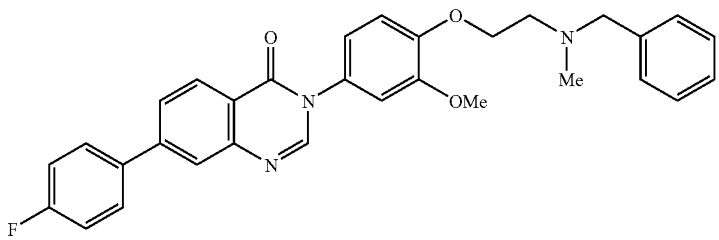 | 3-(4-{2-[benzyl(methyl)amino]-ethoxy}-3-methoxyphenyl)-7-(4-fluorophenyl)-4(3H)-quinazolinone |
| H11 | 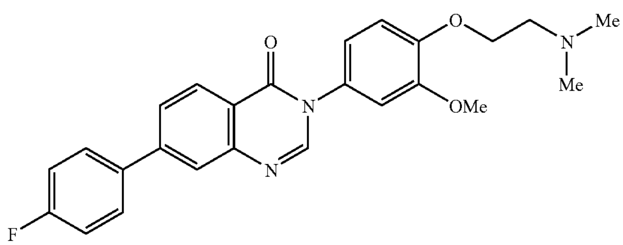 | 3-{4-[2-(dimethylamino)-ethoxy]-3-methoxyphenyl}-7-(4-fluorophenyl)-4(3H)-quinazolinone |
| H12 | 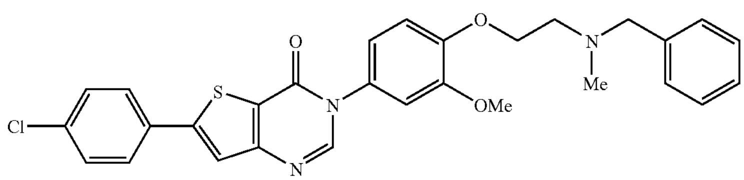 | 3-(4-{2-[benzyl(methyl)amino]-ethoxy}-3-methoxyphenyl)-6-(4-chlorophenyl)thieno[3,2-d]pyrimidin-4(3H)-one |
| H13 | 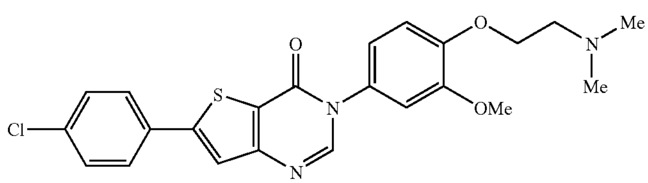 | 6-(4-chlorophenyl)-3-{4-[2-(dimethylamino)ethoxy]-3-methoxyphenyl}thieno[3,2-d]pyrimidin-4(3H)-one |
| H14 | 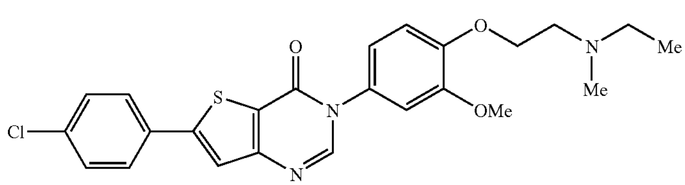 | 6-(4-chlorophenyl)-3-(4-{2-[ethyl(methyl)amino]ethoxy}-3-methoxyphenyl)thieno[3,2-d]pyrimidin-4(3H)-one |
| H15 | 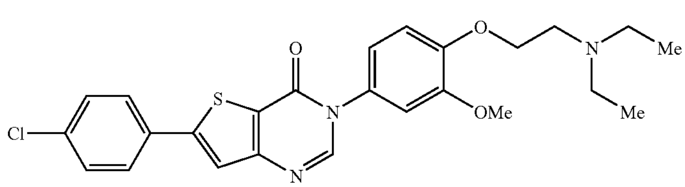 | 6-(4-chlorophenyl)-3-{4-[2-(diethylamino)ethoxy]-3-methoxyphenyl}thieno[3,2-d]pyrimidin-4(3H)-one |

-continued

| Example No. | Structure | Name |
|---|---|---|
| H16 | 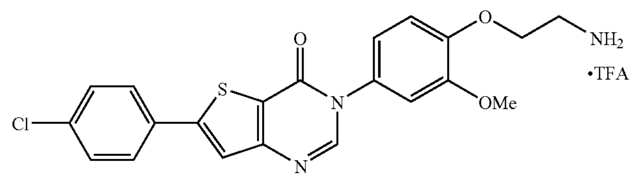 | 3-[4-(2-aminoethoxy)-3-methoxyphenyl]-6-(4-chlorophenyl)thieno[3,2-d]pyrimidin-4(3H)-one trifluoroacetate salt |
| H17 | 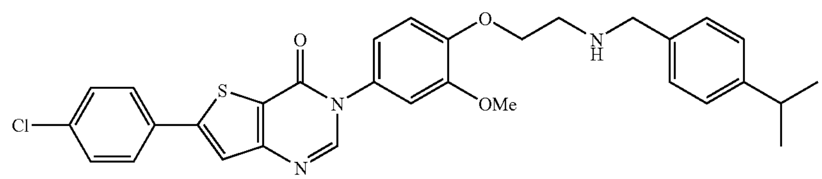 | 6-(4-chlorophenyl)-3-(4-{2-[(4-isopropylbenzyl)amino]ethoxy}-3-methoxyphenyl)thieno[3,2-d]pyrimidin-4(3H)-one |
| H18 | 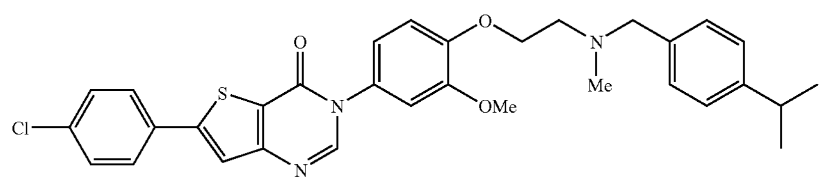 | 6-(4-chlorophenyl)-3-(4-{2-[(4-isopropylbenzyl)(methyl)amino]-ethoxy}-3-methoxyphenyl)thieno[3,2-d]pyrimidin-4(3H)-one |
| H19 | 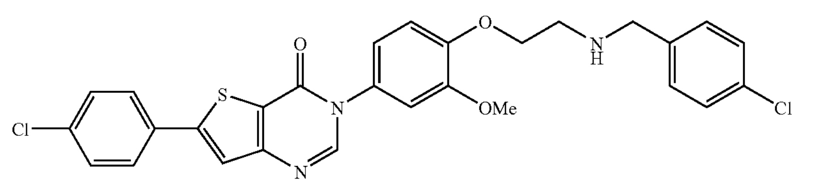 | 3-(4-{2-[(4-chlorobenzyl)amino]ethoxy}-3-methoxyphenyl)-6-(4-chlorophenyl)thieno[3,2-d]pyrimidin-4(3H)-one |
| H20 | 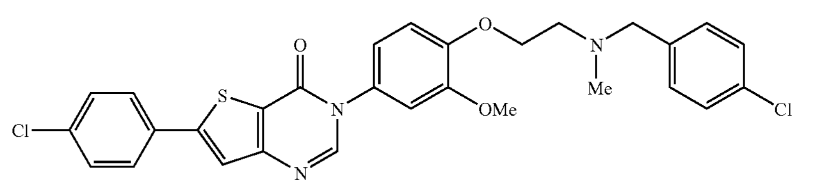 | 3-(4-{2-[(4-chlorobenzyl)(methyl)amino]ethoxy}-3-methoxyphenyl)-6-(4-chlorophenyl)thieno[3,2-d]pyrimidin-4(3H)-one |
| H21 | 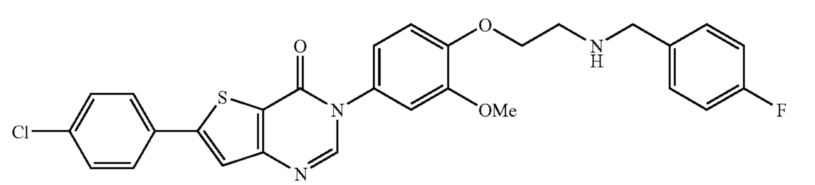 | 6-(4-chlorophenyl)-3-(4-{2-[(4-fluorobenzyl)amino]ethoxy}-3-methoxyphenyl)thieno[3,2-d]pyrimidin-4(3H)-one |
| H22 | 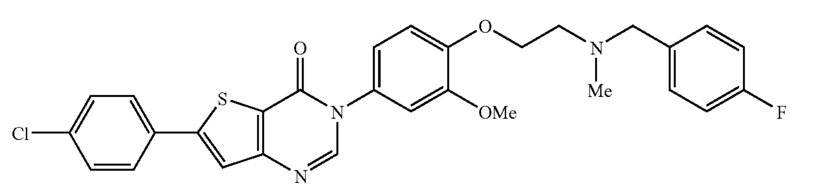 | 6-(4-chlorophenyl)-3-(4-{2-[(4-fluorobenzyl)(methyl)amino]-ethoxy}-3-methoxyphenyl)-thieno[3,2-d]pyrimidin-4(3H)-one |
| H23 | 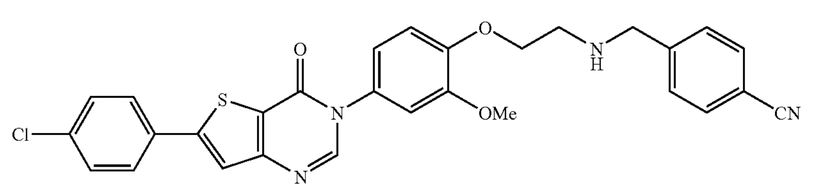 | 4-[({2-[4-(6-(4-chlorophenyl)-4-oxothieno[3,2-d]pyrimidin-3(4H)-yl)-2-methoxyphenoxy]-ethyl}amino)methyl]benzonitrile |

-continued

| Example No. | Structure | Name |
|---|---|---|
| H24 | 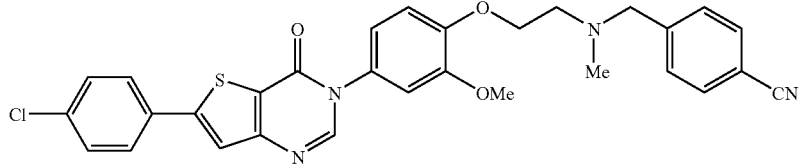 | 4-{[{2-[4-(6-(4-chlorophenyl)-4-oxothieno[3,2-d]pyrimidin-3(4H)-yl)-2-methoxyphenoxy]-ethyl}(methyl)amino]methyl}-benzonitrile |
| H25 | 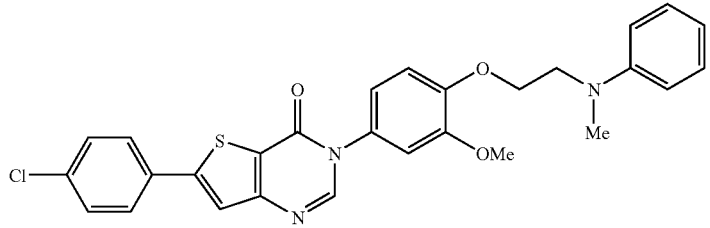 | 6-(4-chlorophenyl)-3-{3-methoxy-4-[2-(methylanilino)-ethoxy]phenyl}thieno[3,2-d]pyrimidin-4(3H)-one |
| H26 | 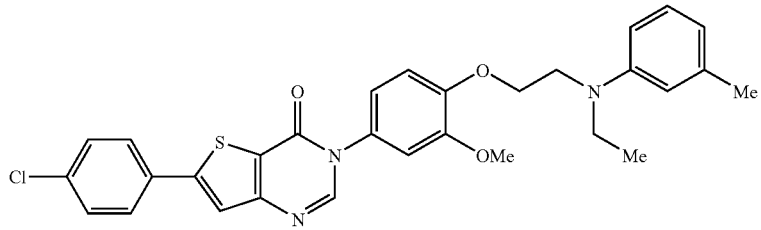 | 6-(4-chlorophenyl)-3-{4-[2-(ethyl-3-methylanilino)ethoxy]-3-methoxyphenyl}thieno[3,2-d]pyrimidin-4(3H)-one |
| H27 | 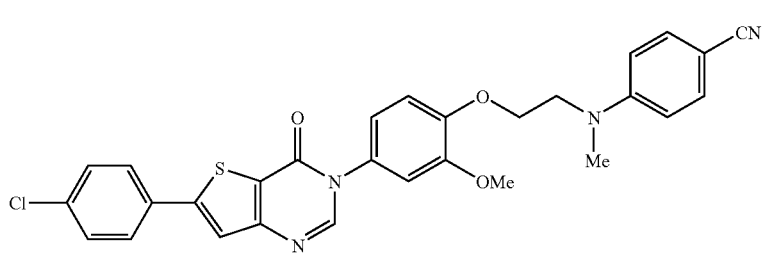 | 4-[{2-[4-(6-(4-chlorophenyl)-4-oxothieno[3,2-d]pyrimidin-3(4H)-yl)-2-methoxyphenoxy]-ethyl}(methyl)amino]-benzonitrile |
| H28 | 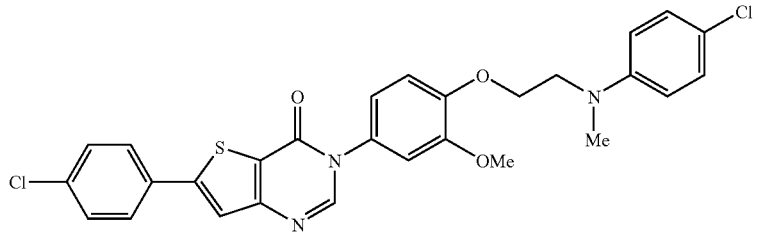 | 3-(4-{2-[4-chloro(methyl)anilino]ethoxy}-3-methoxy-phenyl)-6-(4-chlorophenyl)-thieno[3,2-d]pyrimidin-4(3H)-one |
| H29 | 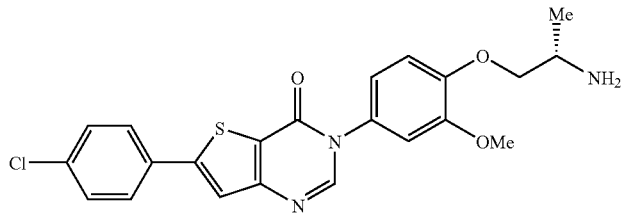 | 3-(4-{[(2S)-2-aminopropyl]-oxy}-3-methoxyphenyl)-6-(4-chlorophenyl)thieno[3,2-d]pyrimidin-4(3H)-one |

-continued

| Example No. | Structure | Name |
|---|---|---|
| H30 | 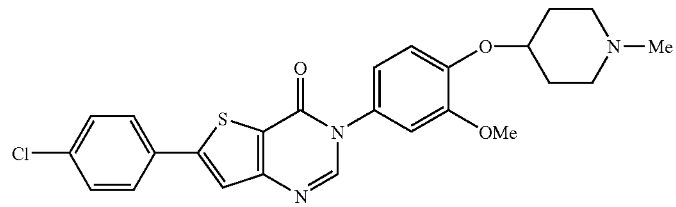 | 6-(4-ohlorophenyl)-3-{3-methoxy-4-[(1-methyl-4-piperidinyl)oxy]phenyl}-thieno[3,2-d]pyrimidin-4(3H)-one |
| I1 | 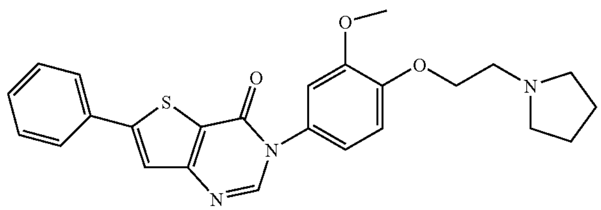 | 3-[3-Methoxy-4-(2-pyrrolidin-1-ylethoxy)phenyl]-6-phenyl-thieno[3,2-d]pyrimidin-4(3H)-one |
| I2 | 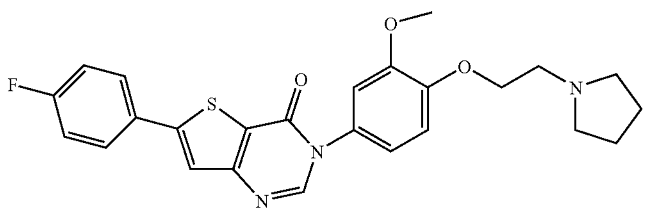 | 6-(4-Fluorophenyl)-3-[3-methoxy-4-(2-pyrrolidin-1-ylethoxy)phenyl]thieno[3,2-d]pyrimidin-4(3H)-one |
| I3 | 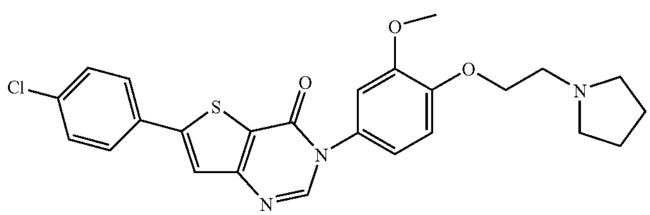 | 6-(4-Chlorophenyl)-3-[3-methoxy-4-(2-pyrrolidin-1-ylethoxy)phenyl]thieno[3,2-d]pyrimidin-4(3H)-one |
| I4 | 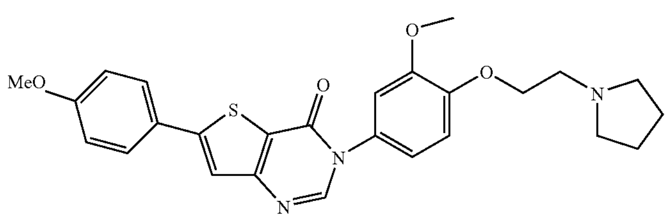 | 6-(4-Methoxyphenyl)-3-[3-methoxy-4-(2-pyrrolidin-1-ylethoxy)phenyl]thieno[3,2-d]pyrimidin-4(3H)-one |
| I5 | 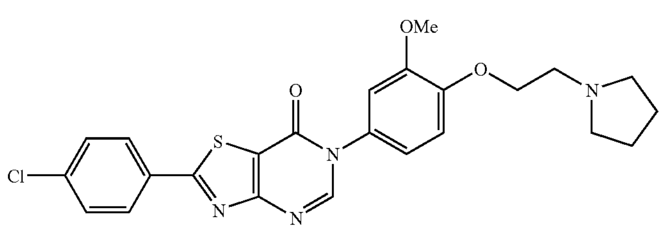 | 2-(4-Chlorophenyl)-6-[3-methoxy-4-(2-pyrrolidin-1ylethoxy)phenyl][1,3]thiazolo[-4,5-d]pyrimidin-7(6H)-one |
| I6 | 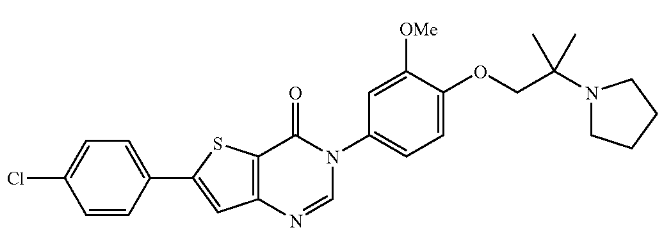 | 6-(4-Chlorophenyl)-3-[3-methoxy-4-(2-methyl-2-pyrrolidin-1-ylpropoxy)phenyl]-thieno[3,2-d]pyrimidin-4(3H)-one |

| Example No. | Structure | Name |
|---|---|---|
| I7 | 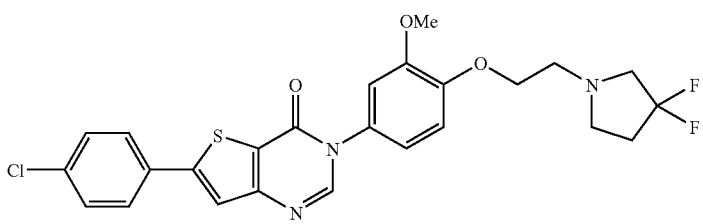 | 6-(4-Chlorophenyl)-3-{4-[2-(3,3-difluoropyrrolidin-1-yl)-ethoxy]-3-methoxyphenyl}-thieno[3,2-d]pyrimidin-4(3H)-one |
| I8 | 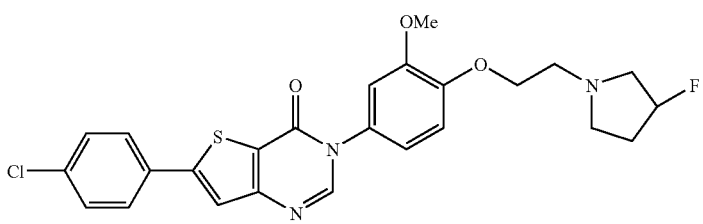 | 6-(4-chlorophenyl)-3-{4-[2-(3-fluoropyrrolidin-1-yl)ethoxy]-3-methoxyphenyl}thieno[3,2-d]-pyrimidin-4(3H)-one |
| J1 | 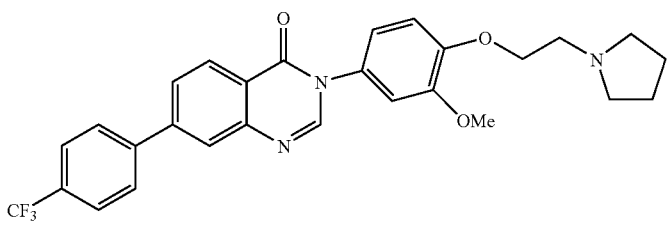 | 3-{3-methoxy-4-[2-(1-pyrrolidinyl)ethoxy]phenyl}-7-[4-(trifluoromethyl)phenyl]-4(3H)-quinazolinone |
| J2 | 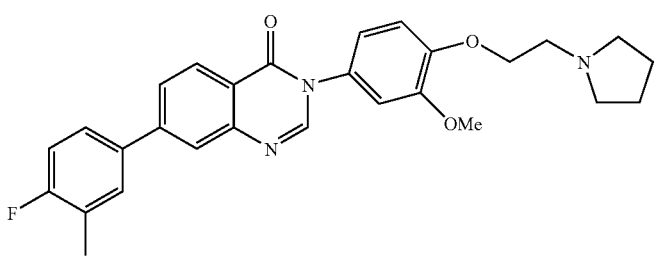 | 7-(4-fluoro-3-methylphenyl)-3-{3-methoxy-4-[2-(1-pyrrolidinyl)ethoxy]phenyl}-4(3H)-quinazolinone |
| J3 | 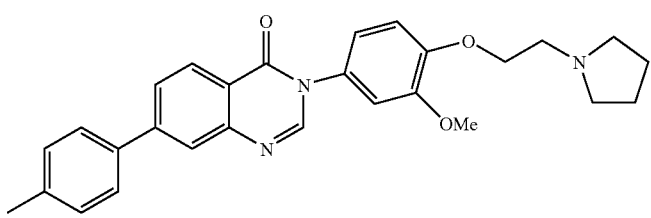 | 3-{3-methoxy-4-[2-(1-pyrrolidinyl)ethoxy]phenyl}-7-(4-methylphenyl)-4(3H)-quinazolinone |
| J4 | 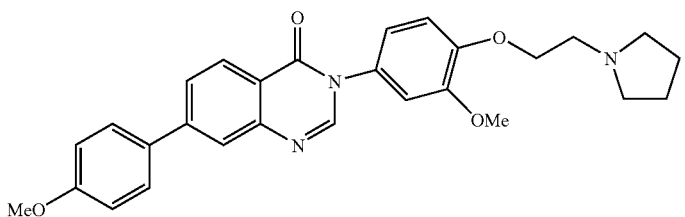 | 7-(4-methoxyphenyl)-3-{3-methoxy-4-[2-(1-pyrrolidinyl)-ethoxy]phenyl}-4(3H)-quinazolinone |

-continued

| Example No. | Structure | Name |
|---|---|---|
| J5 | 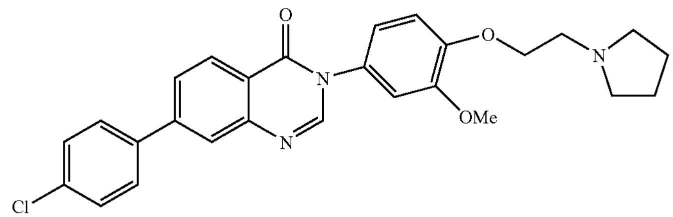 | 7-(4-chlorophenyl)-3-{3-methoxy-4-[2-(1-pyrrolidinyl)-ethoxy]phenyl}-4(3H)-quinazolinone |
| J6 | 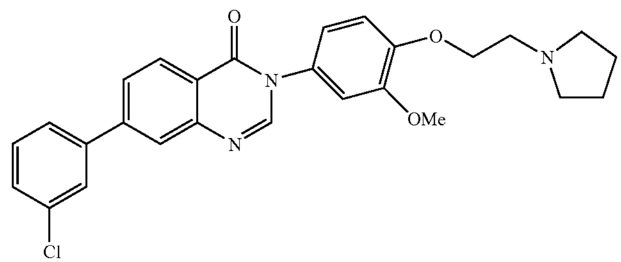 | 7-(3-chlorophenyl)-3-{3-methoxy-4-[2-(1-pyrrolidinyl)-ethoxy]phenyl}-4(3H)-quinazolinone |
| J7 | 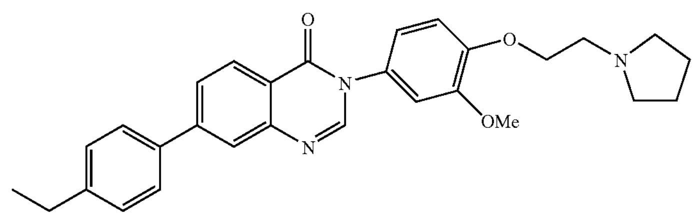 | 7-(4-ethylphenyl)-3-{3-methoxy-4-[2-(1-pyrrolidinyl)-ethoxy]phenyl}-4(3H)-quinazolinone |
| J8 | 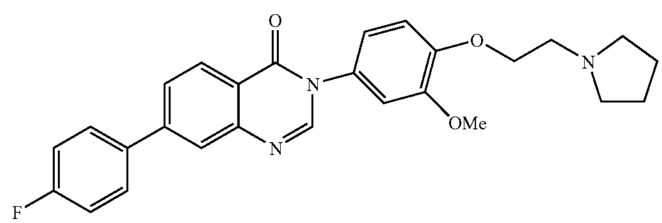 | 7-(4-fluorophenyl)-3-{3-methoxy-4-[2-(1-pyrrolidinyl)-ethoxy]phenyl}-4(3H)-quinazolinone |
| J9 | 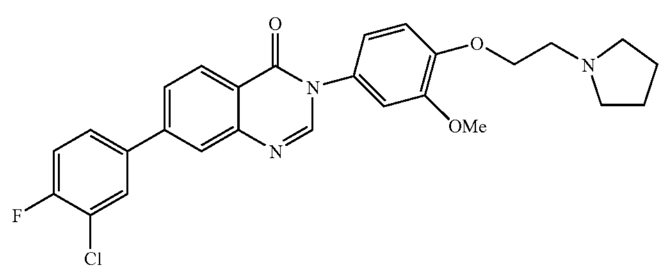 | 7-(3-chloro-4-fluorophenyl)-3-{3-methoxy-4-[2-(1-pyrrolidinyl)ethoxy]phenyl}-4(3H)-quinazolinone |
| J10 | 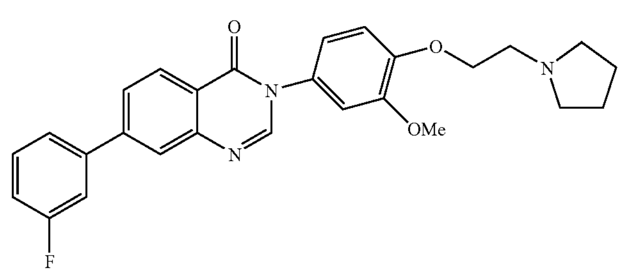 | 7-(3-fluorophenyl)-3-{3-methoxy-4-[2-(1-pyrrolidinyl)-ethoxy]phenyl}-4(3H)-quinazolinone |

-continued

| Example No. | Structure | Name |
|---|---|---|
| J11 | 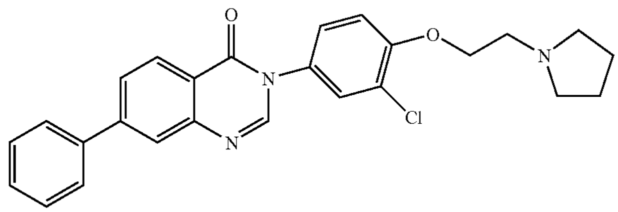 | 3-{3-chloro-4-[2-(1-pyrrolidinyl)ethoxy]phenyl}-7-phenyl-4(3H)-quinazolinone |
| J12 | 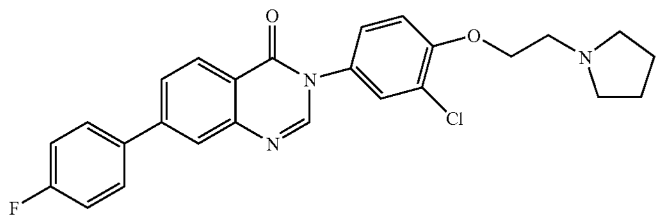 | 3-{3-chloro-4-[2-(1-pyrrolidinyl)ethoxy]phenyl}-7-(4-fluorophenyl)-4(3H)-quinazolinone |
| J13 | 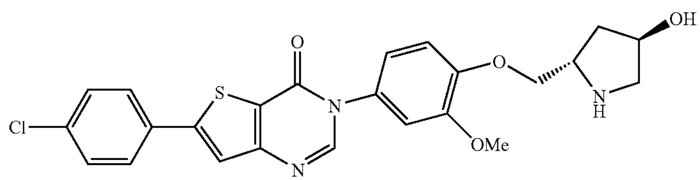 | 6-(4-chlorophenyl)-3-(4-{[(2S,4R)-4-hydroxy-pyrrolidinyl]methoxy}-3-methoxyphenyl)thieno[3,2-d]pyrimidin-4(3H)-one |
| J14 | 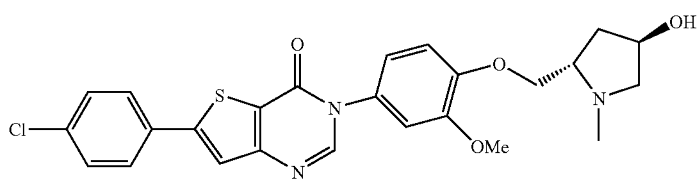 | 6-(4-chlorophenyl)-3-(4-{[(2S,4R)-4-hydroxy-1-methylpyrrolidinyl]methoxy}-3-methoxyphenyl)thieno[3,2-d]pyrimidin-4(3H)-one |
| J15 | 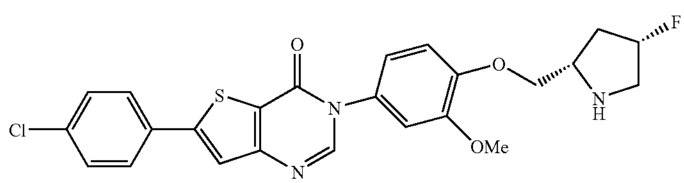 | 6-(4-chlorophenyl)-3-(4-{[(2S,4S)-4-fluoropyrrolidinyl]-methoxy)-3-methoxyphenyl)-thieno[3,2-d]pyrimidin-4(3H)-one |
| J16 | 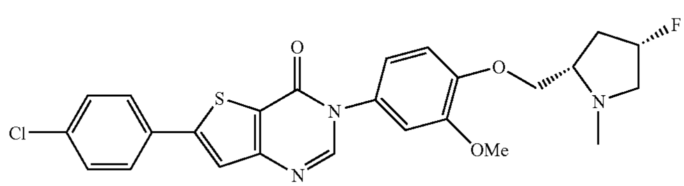 | 6-(4-chlorophenyl)-3-(4-{[(2S,4S)-4-fluoro-1-methyl-pyrrolidinyl]methoxy}-3-methoxyphenyl)thieno[3,2-d]pyrimidin-4(3H)-one |
| J17 | 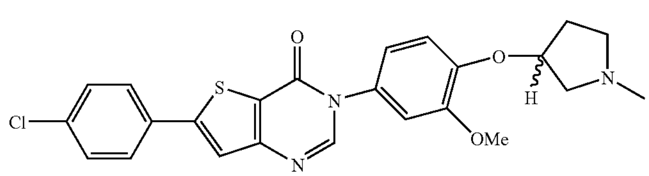 | 6-(4-chlorophenyl)-3-{3-methoxy-4-[(1-methyl-3-pyrrolidinyl)oxy]phenyl}thieno-[3,2-d]pyrimidin-4(3H)-one |
| J18 | 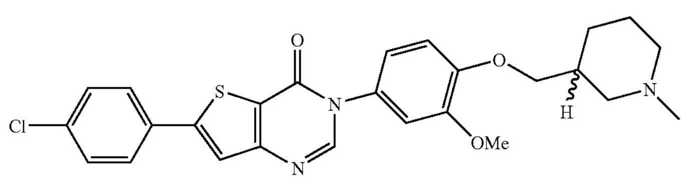 | 6-(4-chlorophenyl)-3-{3-methoxy-4-[(1-methyl-3-piperidinyl)methoxy]phenyl}-thieno[3,2-d]pyrimidin-4(3H)-one |

-continued

| Example No. | Structure | Name |
|---|---|---|
| J19 | 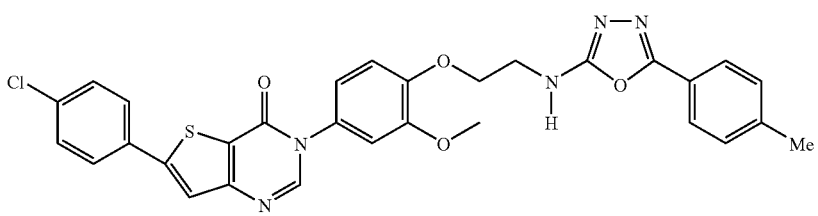 | 6-(4-chlorophenyl)-3-[3-methoxy-4-(2-{[5-(4-methyl-phenyl)-1,3,4-oxadiazol-2-yl]-amino}ethoxy)phenyl]thieno-[3,2-d]pyrimidin-4(3H)-one |
| K1 | 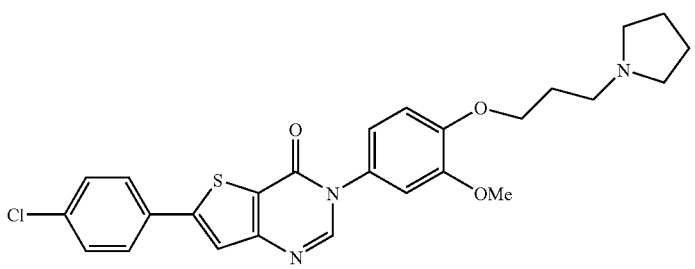 | 6-(4-Chlorophenyl)-3-[3-methoxy-4-(3-pyrrolidin-1-yl-propoxy)phenyl] thieno[3,2-d]pyrimidin-4(3H)-one (1) |
| K2 | 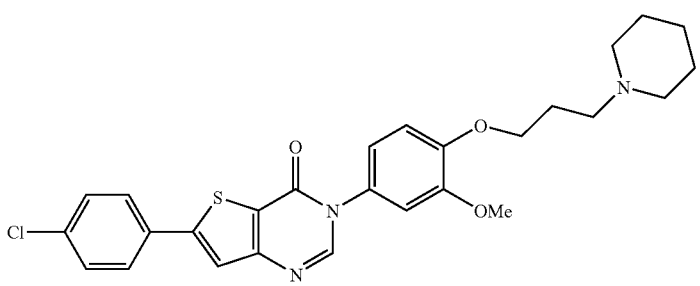 | 6-(4-Chlorophenyl)-3-[3-methoxy-4-(3-piperidin-1-yl-propoxy)phenyl] thieno[3,2-d]pyrimidin-4(3H)-one |
| K3 | 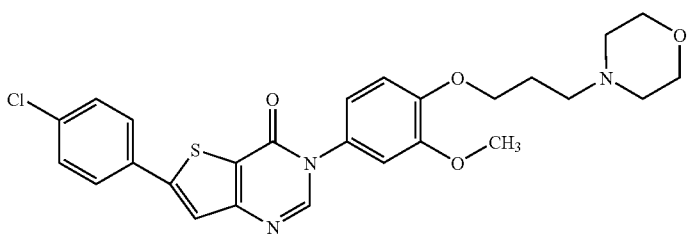 | 6-(4-Chlorophenyl)-3-[3-methoxy-4-(3-morpholin-4-yl-propoxy)phenyl] thieno[3,2-d]pyrimidin-4(3H)-one |
| K4 | 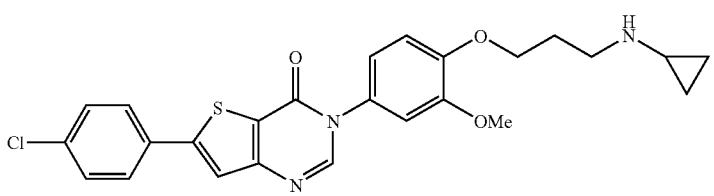 | 6-(4-Chlorophenyl)-3-{4-[3-(cyclopropylamino)propoxy]-3-methoxy-phenyl}thieno[3,2-d]pyrimidin-4(3H)-one |
| K5 | 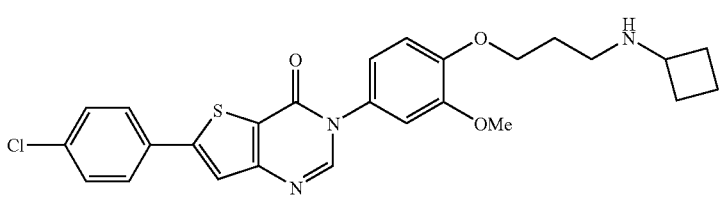 | 6-(4-Chlorophenyl)-3-{4-[3-(cyclobutylamino)propoxy]-3-methoxy-phenyl}thieno[3,2-d]pyrimidin-4(3H)-one |

| Example No. | Structure | Name |
|---|---|---|
| K6 | 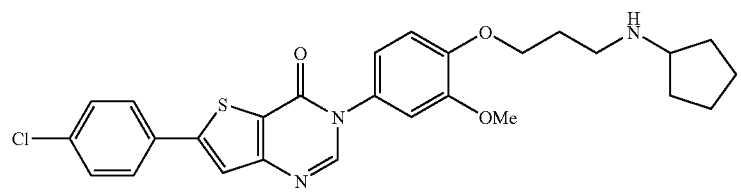 | 6-(4-Chlorophenyl)-3-{4-[3-(cyclopentylamino)propoxy]-3-methoxy-phenyl}thieno[3,2-d]pyrimidin-4(3H)-one |
| K7 | 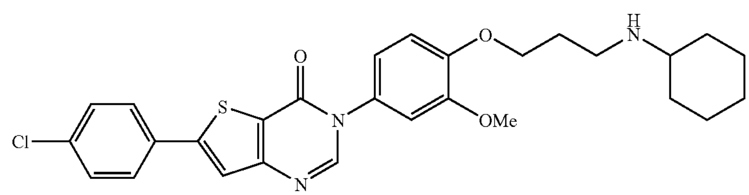 | 6-(4-Chlorophenyl)-3-{4-[3-(cyclohexylamino)propoxy]-3-methoxy-phenyl}thieno[3,2-d]pyrimidin-4(3H)-one |
| K8 | 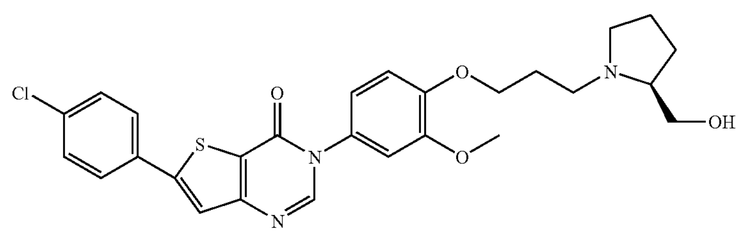 | 6-(4-Chlorophenyl)-3-(4-{3-[(2S)-2-(hydroxymethyl)-pyrrolidin-1-yl]propoxy}-3-methoxyphenyl) thieno[3,2-d]pyrimidin-4(3H)-one |
| K9 | 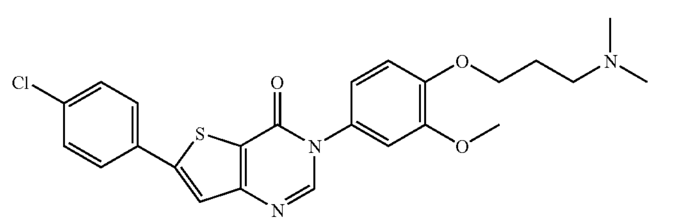 | 6-(4-Chlorophenyl)-3-{4-[3-(dimethylamino)propoxy]-3-methoxy-phenyl}thieno[3,2-d]pyrimidin-4(3H)-one |
| K10 | 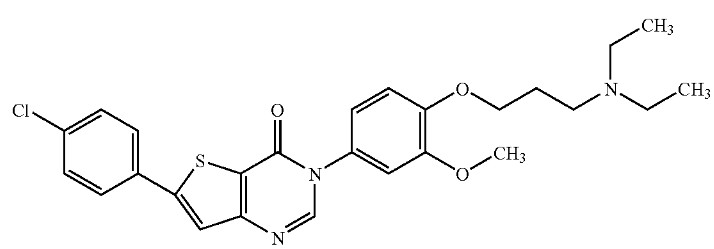 | 6-(4-Chlorophenyl)-3-{4-[3-(diethylamino)propoxy]-3-methoxyphenyl} thieno[3,2-d]pyrimidin-4(3H)-one |
| K11 | 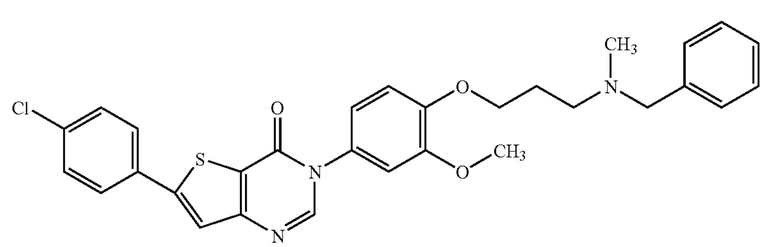 | 3-(4-{3-[benzyl(methyl)amino]-propoxy}-3-methoxyphenyl)-6-(4-chlorophenyl)thieno[3,2-d]pyrimidin-4(3H)-one |

-continued

| Example No. | Structure | Name |
|---|---|---|
| K12 | 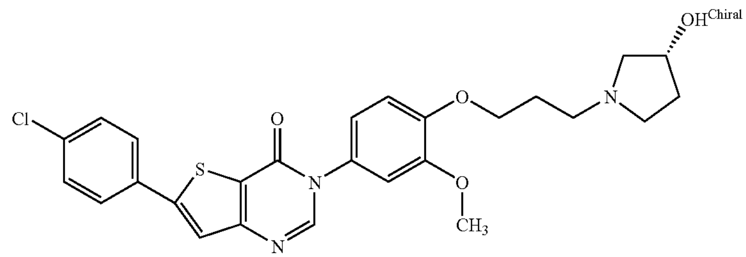 | 6-(4-Chlorophenyl)-3-(4-{3-[(3R)-3-hydroxypyrrolidin-1-yl]propoxy}-3-methoxyphenyl)-thieno[3,2-d]pyrimidin-4(3H)-one |
| K13 | 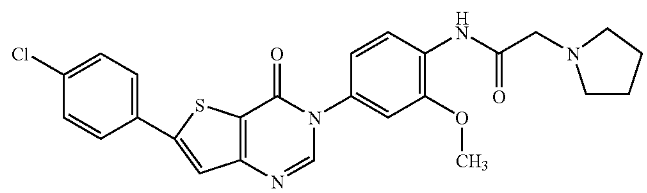 | N-{4-[6-(4-chlorophenyl)-4-oxothieno[3,2-d]pyrimidin-3(4H)-yl]-2-methoxyphenyl}-2-pyrrolidin-1-ylacetamide |
| K14 | 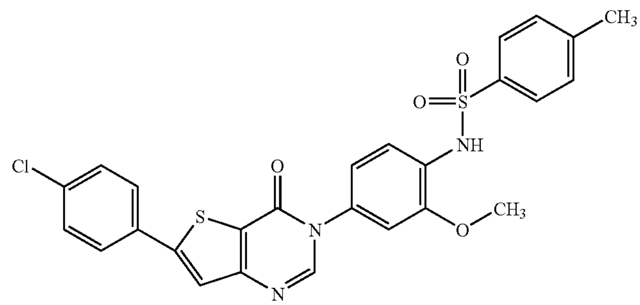 | N-{4-[6-(4-chlorophenyl)-4-oxothieno[3,2-d]pyrimidin-3(4H)-yl]-2-methoxyphenyl}-4-methylbenzenesulfonamide |
| K15 | 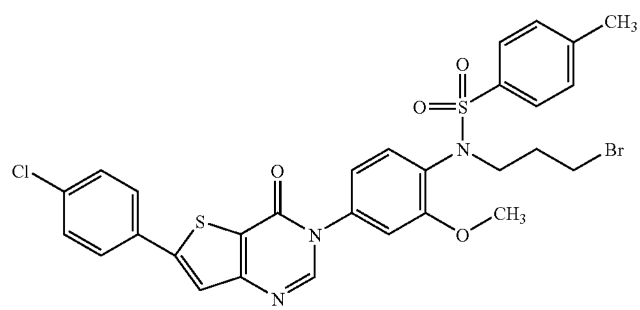 | N-(3-bromopropyl)-N-{4-[6-(4-chlorophenyl)-4-oxothieno[3,2-d]pyrimidin-3(4H)-yl]-2-methoxyphenyl}-4-methylbenzenesulfonamide |
| K16 | 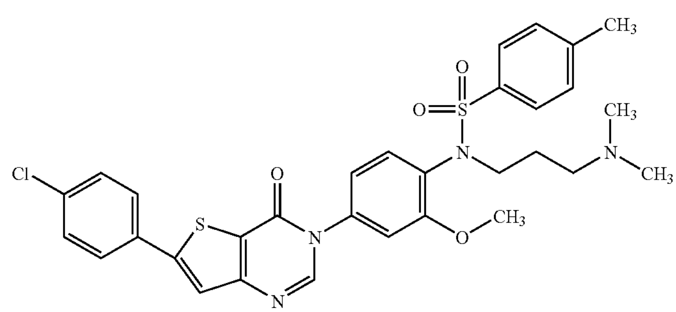 | N-{4-[6-(4-chlorophenyl)-4-oxothieno[3,2-d]pyrimidin-3(4H)-yl]-2-methoxyphenyl}-N-[3-(dimethylamino)propyl]-4-methylbenzene-sulfonamide (14) |

| Example No. | Structure | Name |
|---|---|---|
| K17 | 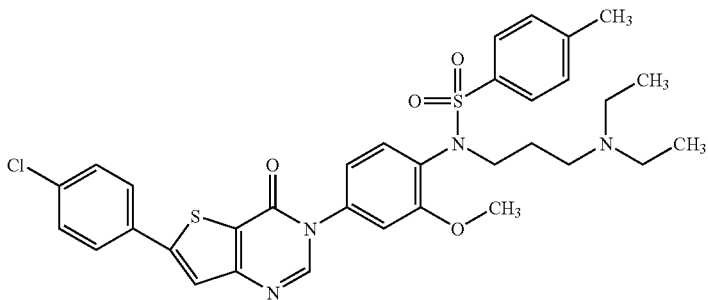 | N-{4-[6-(4-chlorophenyl)-4-oxothieno[3,2-d]pyrimidin-3(4H)-yl]-2-methoxyphenyl}-N-[3-(diethylamino)propyl]-4-methylbenzene-sulfonamide (14) |
| K18 | 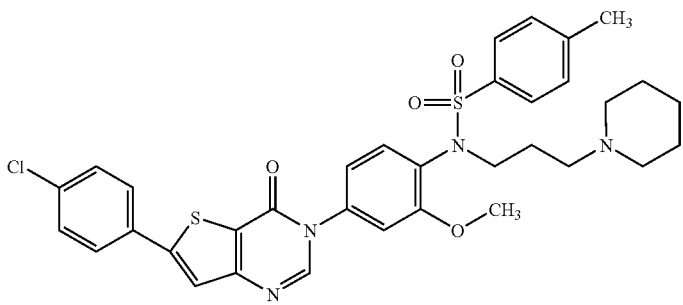 | N-{4-[6-(4-chlorophenyl)-4-oxothieno[3,2-d]pyrimidin-3(4H)-yl]-2-methoxyphenyl}-4-methyl-N-(3-piperidin-1-ylpropyl)benzene-sulfonamide |
| K19 | 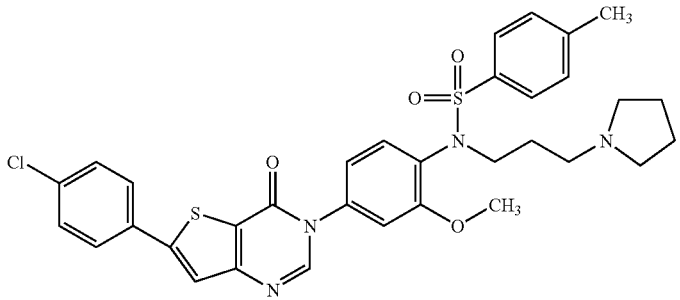 | N-{4-[6-(4-chlorophenyl)-4-oxothieno[3,2-d]pyrimidin-3(4H)-yl]-2-methoxyphenyl}-4-methyl-N-(3-pyrrolidin-1-ylpropyl)benzene-sulfonamide |
| K20 | 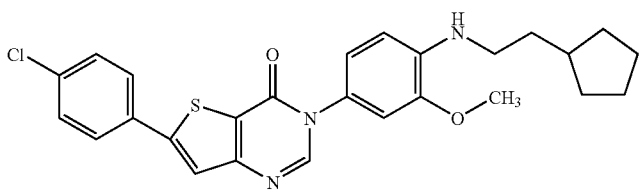 | 6-(4-chlorophenyl)-3-{3-methoxy-4-[(2-pyrrolidin-1-yl-ethyl)amino] phenyl}thieno[3,2-d]pyrimidin-4(3H)-one |
| K21 | 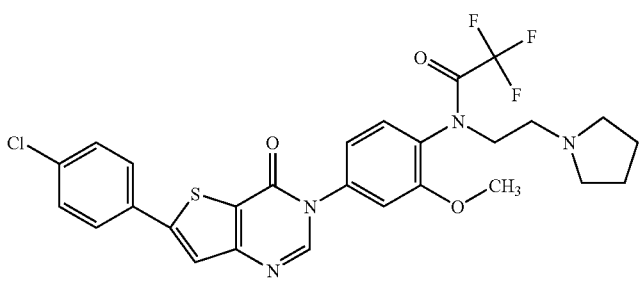 | N-{4-[6-(4-chlorophenyl)-4-oxothieno[3,2-d]pyrimidin-3(4H)-yl]-2-methoxyphenyl}-2,2,2-trifluoro-N-(2-pyrrolidin-1-ylethyl)acetamide |

-continued

| Example No. | Structure | Name |
|---|---|---|
| K22 | 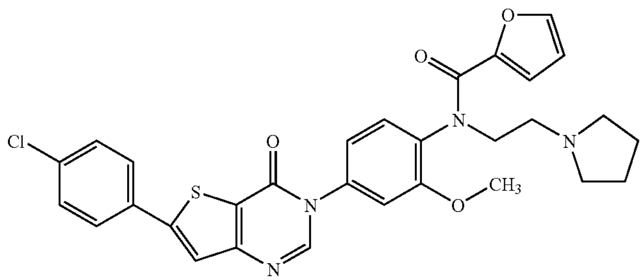 | N-{4-[6-(4-chlorophenyl)-4-oxothieno[3,2-d]pyrimidin-3(4H)-yl]-2-methoxyphenyl}-N-(2-pyrrolidin-1-ylethyl)-2-furamide |
| K23 | 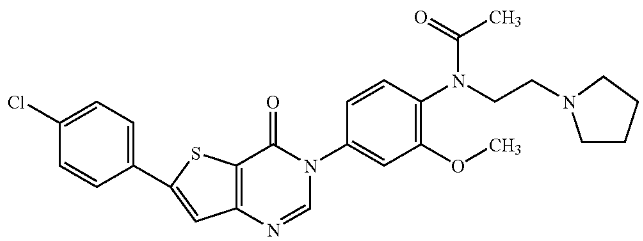 | N-{4-[6-(4-chlorophenyl)-4-oxothieno[3,2-d]pyrimidin-3(4H)-yl]-2-methoxyphenyl}-N-(2-pyrrolidin-1-ylethyl)-acetamide |
| K24 | 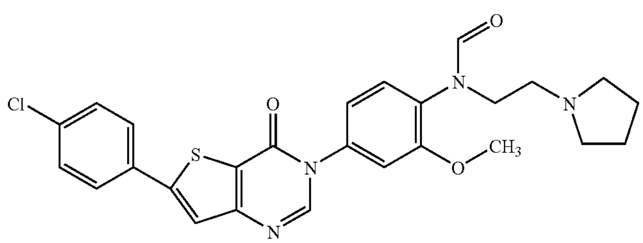 | 4-[6-(4-Chlorophenyl)-4-oxothieno[3,2-d]pyrimidin-3(4H)-yl]-2-methoxyphenyl(2-pyrrolidin-1-ylethyl)formamide |
| K25 | 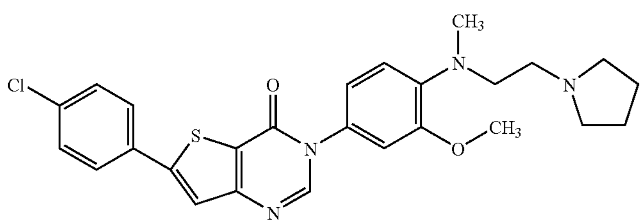 | 6-(4-Chlorophenyl)-3-{3-methoxy-4-[methyl(2-pyrrolidin-1-ylethyl)-amino]phenyl}-thieno[3,2-d]pyrimidin-4(3H)-one |
| K26 | Chiral | 6-(4-Chlorophenyl)-3-(3-methoxy-4-{[(2S)-1-methyl-pyrrolidin-2-yl] methoxy}-phenyl)thieno[3,2-d]pyrimidin-4(3H)-one |
| K27 | 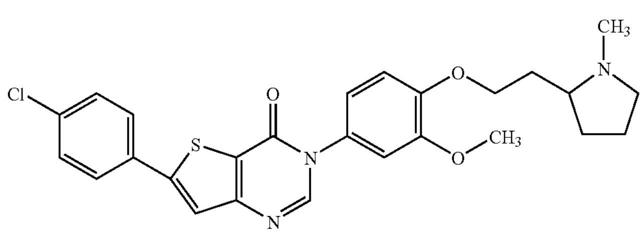 | 6-(4-Chlorophenyl)-3-{3-methoxy-4-[2-(1-methyl-pyrrolidin-2-yl)ethoxy] phenyl}-thieno[3,2-d]pyrimidin-4(3H)-one |

| Example No. | Structure | Name |
|---|---|---|
| K28 | 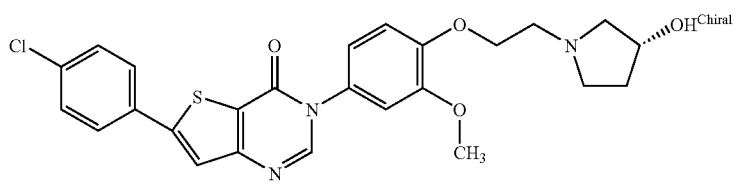 | 6-(4-Chlorophenyl)-3-(4-{2-[(3R)-3-hydroxypyrrolidin-1-yl]ethoxy}-3-methoxyphenyl)-thieno[3,2-d]pyrimidin-4(3H)-one |
| K29 | 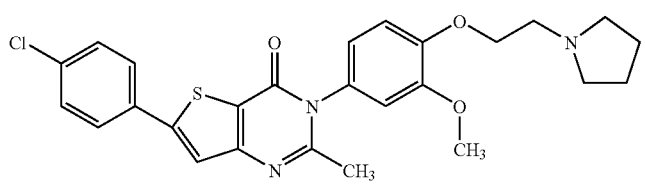 | 6-(4-Chlorophenyl)-3-[3-methoxy-4-(2-pyrrolidin-1-yl-ethoxy)phenyl]-2-methyl-thieno[3,2-d]pyrimidin-4(3H)-one |
| K30 | 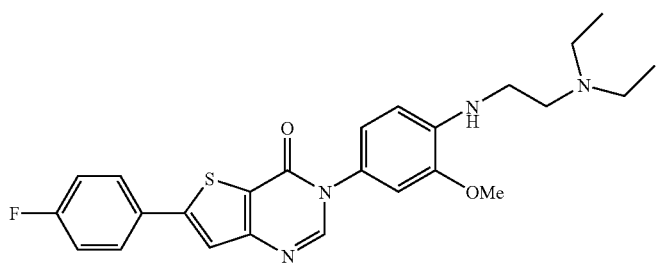 | 3-(4-{[2-(diethylamino)ethyl]-amino}-3-methoxyphenyl)-6-(4-fluorophenyl) thieno[3,2-d]-pyrimidin-4(3H)-one |
| K31 | 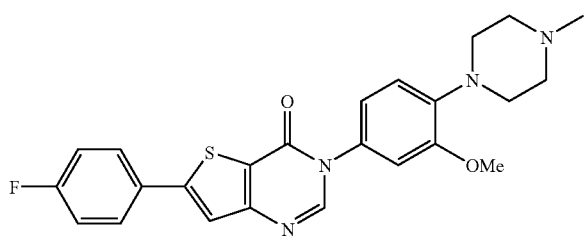 | 6-(4-Fluorophenyl)-3-[3-methoxy-4-(4-methylpiperazin-1-yl)phenyl]thieno[3,2-d]pyrimidin-4(3H)-one |
| K32 | 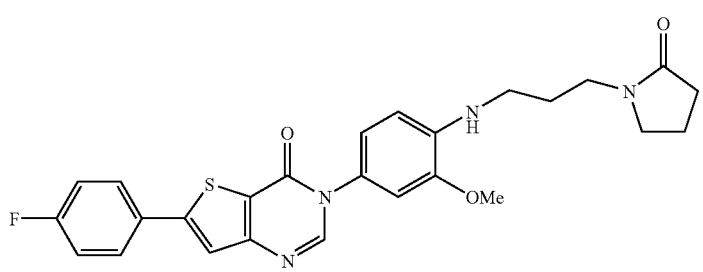 | 6-(4-Fluorophenyl)-3-(3-methoxy-4-{[3-(2-oxopyrrolidin-1-yl)propyl]-amino}phenyl) thieno[3,2-d]pyrimidin-4(3H)-one |
| K33 | 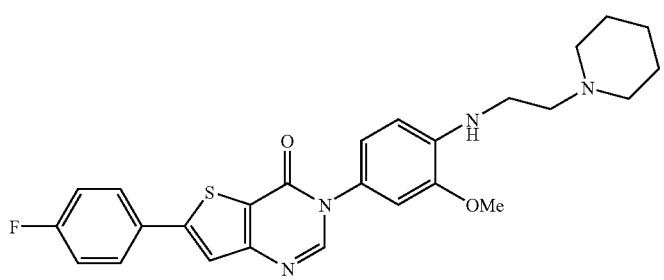 | 6-(4-Fluorophenyl)-3-{3-methoxy-4-[(2-piperidin-1-yl-ethyl)amino]phenyl} thieno[3,2-d]pyrimidin-4(3H)-one |

-continued

| Example No. | Structure | Name |
|---|---|---|
| K34 | 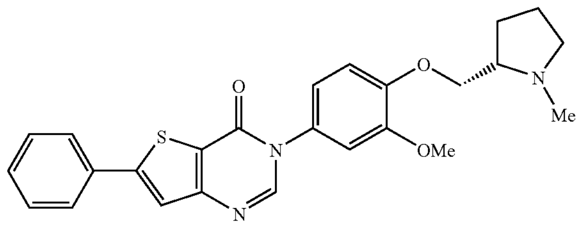 | 3-(3-Methoxy-4-{[(2R)-1-methylpyrrolidin-2-yl]-methoxy}phenyl)-6-phenyl-thieno [3,2-d]pyrimidin-4(3H)-one |
| K35 | 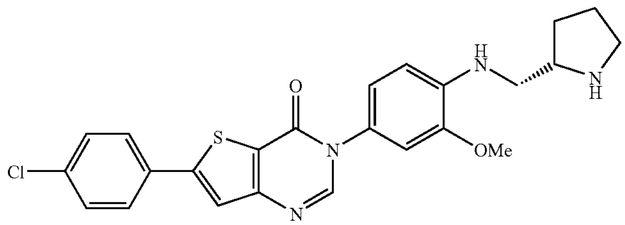 | 6-(4-Chlorophenyl)-3-(3-methoxy-4-{[(2R)-pyrrolidin-2-ylmethyl]amino}phenyl) thieno[3,2-d]pyrimidin-4(3H)-one |
| K36 | 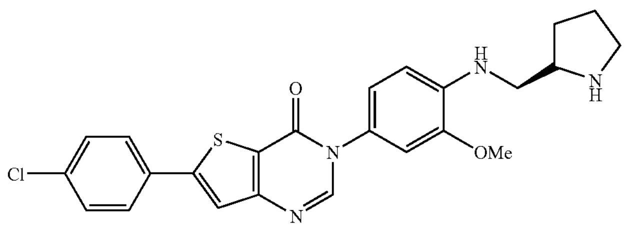 | 6-(4-Chlorophenyl)-3-(3-methoxy-4-{[(2S)-pyrrolidin-2-ylmethyl]amino}phenyl) thieno[3,2-d]pyrimidin-4(3H)-one |
| K37 | 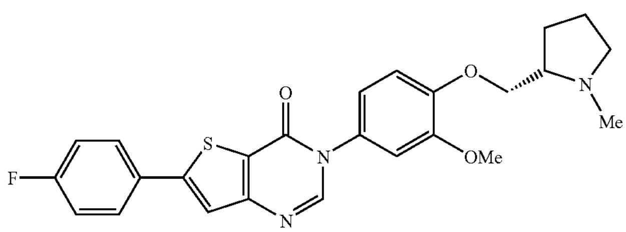 | 6-(4-Fluorophenyl)-3-(3-methoxy-4-{[(2R)-1-methyl-pyrrolidin-2-yl]methoxy}-phenyl) thieno[3,2-d]pyrimidin-4(3H)-one |
| L1 | 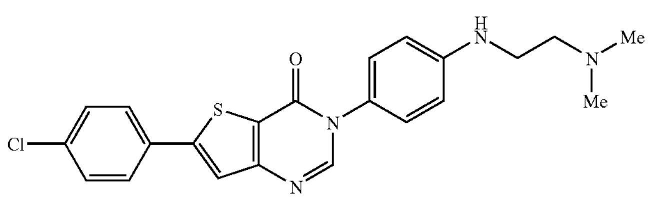 | 6-(4-chlorophenyl)-3-(4-{[2-(dimethylamino)ethyl]amino}-phenyl)thieno[3,2-d]pyrimidin-4(3H)-one |
| L2 | 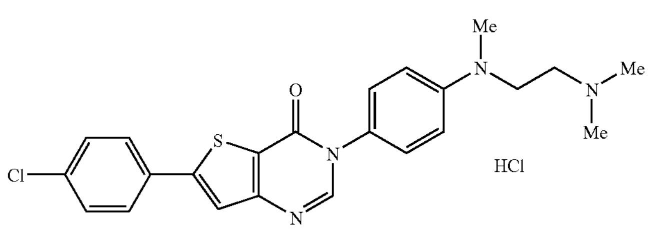 | 6-(4-chlorophenyl)-3-{4-[[2-(dimethylamino)ethyl](methyl)-amino]phenyl}thieno[3,2-d]pyrimidin-4(3H)-one hydrochloride |
| L3 | 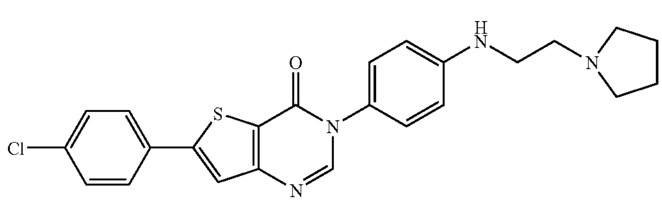 | 6-(4-chlorophenyl)-3-(4-{[2-(1-pyrrolidinyl)ethyl]amino}-phenyl)thieno[3,2-d]pyrimidin-4(3H)-one |

-continued

| Example No. | Structure | Name |
|---|---|---|
| L4 | 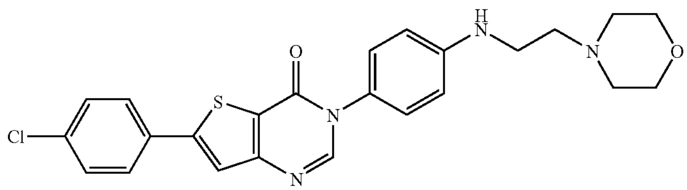 | 6-(4-chlorophenyl)-3-(4-{[2-(4-morpholinyl)ethyl]amino}-phenyl)thieno[3,2-d]pyrimidin-4(3H)-one |
| L5 | 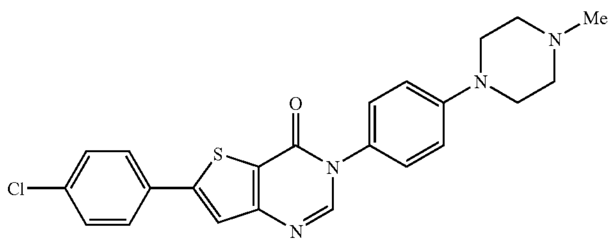 | 6-(4-chlorophenyl)-3-[4-(4-methyl-1-piperazinyl)phenyl]-thieno[3,2-d]pyrimidin-4(3H)-one |
| M1 | 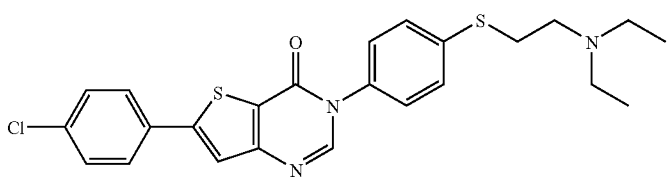 | 6-(4-chlorophenyl)-3-(4-{[2-(diethylamino)ethyl]sulfanyl}-phenyl)thieno[3,2-d]pyrimidin-4(3H)-one |
| M2 | 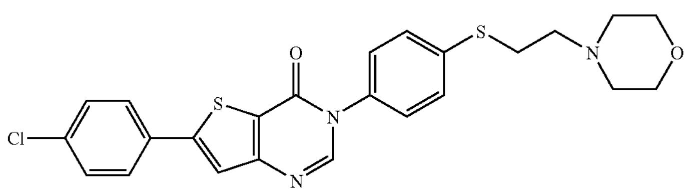 | 6-(4-chlorophenyl)-3-(4-{[2-(4-morpholinyl)ethyl]sulfanyl}-phenyl)thieno[3,2-d]pyrimidin-4(3H)-one |
| N1 | 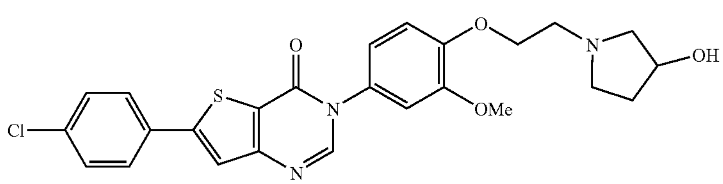 | 6-(4-chlorophenyl)-3-{4-[2-(3-hydroxypyrrolidin-1-yl)ethoxy]-3-methoxyphenyl}thieno[3,2-d]pyrimidin-4(3H)-one |
| N2 | 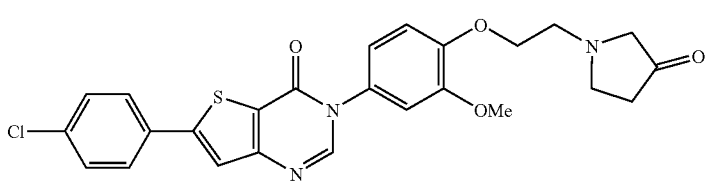 | 6-(4-chlorophenyl)-3-{3-methoxy-4-[2-(3-oxopyrrolidin-1-yl)ethoxy]phenyl}thieno[3,2-d]pyrimidin-4(3H)-one |
| O1 | 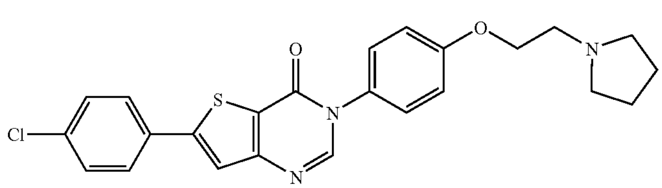 | 6-(4-chlorophenyl)-3-[4-(2-pyrrolidin-1-ylethoxy)phenyl]-thieno[3,2-d]pyrimidin-4(3H)-one |

| Example No. | Structure | Name |
|---|---|---|
| O2 | 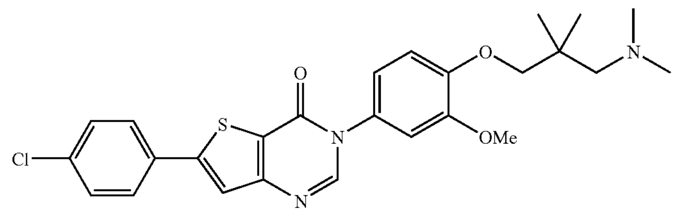 | 6-(4-Chlorophenyl)-3-{4-[3-(dimethylamino)-2,2-dimethyl-propoxy]-3-methoxyphenyl}-thieno[3,2-d]pyrimidin-4(3H)-one |
| O3 | 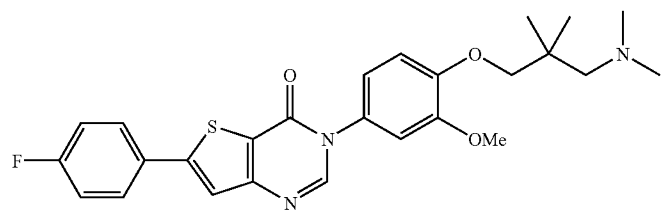 | 6-(4-Fluorophenyl)-3-{4-[3-(dimethylamino)-2,2-dimethyl-propoxy]-3-methoxyphenyl}-thieno[3,2-d]pyrimidin-4(3H)-one |
| O4 | 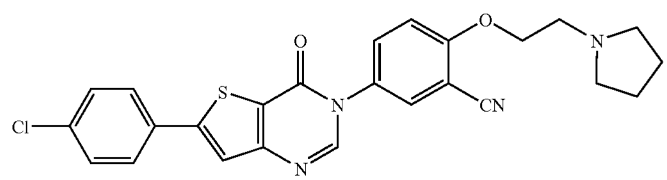 | 5-[6-(4-Chlorophenyl)-4-oxo-thieno[3,2-d]pyrimidin-3(4H)-yl]-2-(2-pyrrolidin-1-ylethoxy)-benzonitrile |
| O5 | 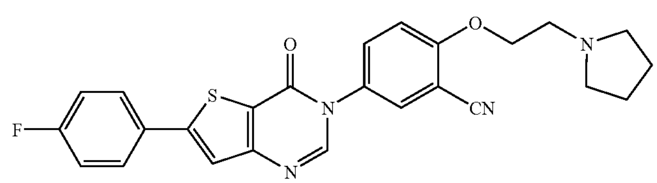 | 5-[6-(4-Fluorophenyl)-4-oxo-thieno[3,2-d]pyrimidin-3(4H)-yl]-2-(2-pyrrolidin-1-ylethoxy)-benzonitrile |
| O6 | 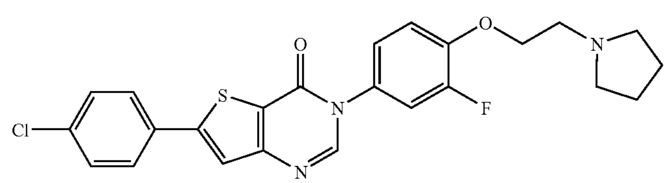 | 6-(4-Chlorophenyl)-3-[3-fluoro-4-(2-pyrrolidin-1-ylethoxy)-phenyl]thieno[3,2-d]pyrimidin-4(3H)-one |

It will be appreciated by those skilled in the art that the compounds of the present invention may also be utilized in the form of a pharmaceutically acceptable salt or solvate or physiologically functional derivative thereof (e.g., a prodrug). The pharmaceutically acceptable salts of the compounds of formula (Ia) include conventional salts formed from pharmaceutically acceptable inorganic or organic acids or bases as well as quaternary ammonium salts. More specific examples of suitable acid salts include maleic, hydrochloric, hydrobromic, sulfuric, phosphoric, nitric, perchloric, fumaric, acetic, propionic, succinic, glycolic, formic, lactic, aleic, tartaric, citric, palmoic, malonic, hydroxymaleic, phenylacetic, glutamic, benzoic, salicylic, fumaric, toluenesulfonic, methanesulfonic (mesylate), naphthaliene-2-sulfonic, benzenesulfonic, hydroxynaphthoic, hydroiodic, malic, steroic, tannic, and the like.

Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminum, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (Ia)) and a solvent. Solvents, by way of example, include water, methanol, ethanol, and acetic acid.

The term "physiologically functional derivative" as used herein refers to any pharmaceutically acceptable derivative of a compound of the present invention, for example, a ester or an amide of a compound of formula (Ia), which upon administration to an animal, particularly a mammal, such as a human, is capable of providing (directly or indirectly) a compound of the present invention or an active metabolite thereof. See, for example, Burger's Medicinal Chemistry and Drug Discovery, 5$^{th}$ Edition, Vol. 1: Principles and Practice.

Processes for preparing pharmaceutically salts, solvates, and physiologically functional derivatives of the compounds of formula (Ia) are conventional in the art. See, e.g., Burger's Medicinal Chemistry and Drug Discovery, 5$^{th}$ Edition, Vol.1: Principles and Practice.

Compounds of formula (Ia) below are conveniently prepared in accordance with the reaction schemes and/or processes outlined or described below.

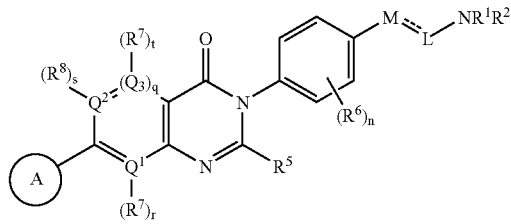

(Ia)

As will be apparent to those skilled in the art, in the processes described below for the preparation of compounds of formula (Ia), certain intermediates, may be in the form of pharmaceutically salts, solvates or physiologically functional derivatives of the compound. Those terms as applied to any intermediate employed in the process of preparing compounds of formula (Ia) have the same meanings as noted above with respect to compounds of formula (Ia). Processes for preparing pharmaceutically acceptable salts, solvates and physiologically functional derivatives of such intermediates are known in the art and are analogous to the process for preparing pharmaceutically acceptable salts, solvates and physiological functional derivatives of the compounds of formula (Ia). Unless otherwise stated, (A), $R^8$, $R^7$, $R^6$, $R^5$, $R^2$, $R^1$, M, L, $Q^1$, $Q^2$, $Q^3$, q, r, s, t, and n are as defined in formula (Ia).

Thus compounds of formula (Ia) may be prepared by reaction of an aniline of formula (II) below with a compound of formula (III) and wherein (A), $R^8$, $R^7$, $R^6$, $R^5$, $R^2$, $R^1$, M, L, $Q^1$, $Q^2$, $Q^3$, q, r, s, t, and n are as defined in formula (Ia).

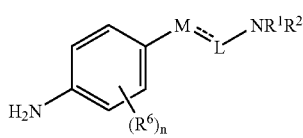

(II)

Compounds of formula (Ia) wherein $R^5$ is H can be prepared from formamidine ester (III) by heating with the appropriate aniline (II) in a solvent such as ethanol or decalin and wherein (A), $R^8$, $R^7$, $R^6$, $R^5$, $R^2$, $R^1$, M, L, $Q^1$, $Q^2$, $Q^3$, q, r, s, t, and n are as defined in formula (Ia).

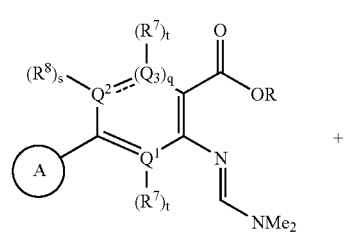

(III)

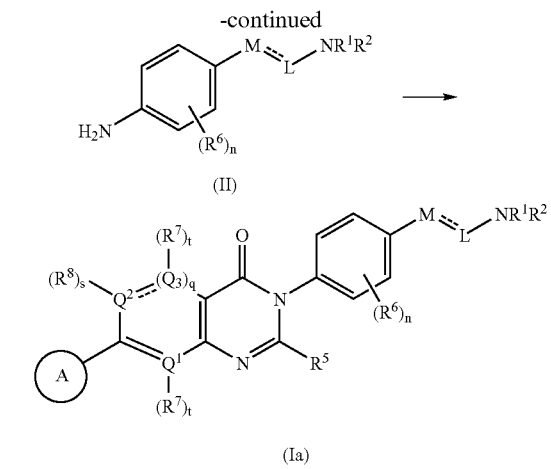

Compounds of formula (Ia) can also be prepared by an amide coupling of the corresponding amino acid (IV) and the desired aniline (II) in a solvent, such as methylene chloride, with amide coupling agents such as EDC, followed by cyclization in refluxing carboxylic acids, such as formic acid and wherein (A), $R^8$, $R^7$, $R^6$, $R^5$, $R^2$, $R_1$, M, L, $Q^1$, $Q^2$, $Q^3$, q, r, s, t, and n are as defined in formula (Ia).

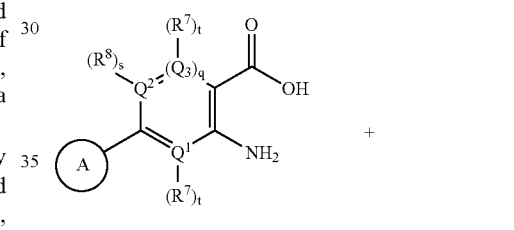

(IV)

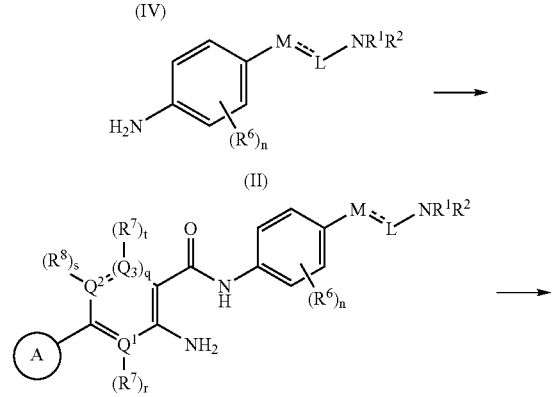

(V)

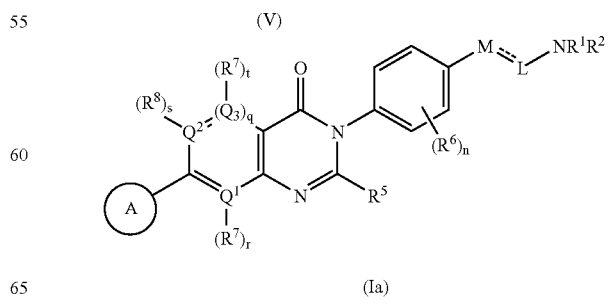

(Ia)

Compounds of formula (Ia) may also be prepared by reaction of a compound of formula (Va)

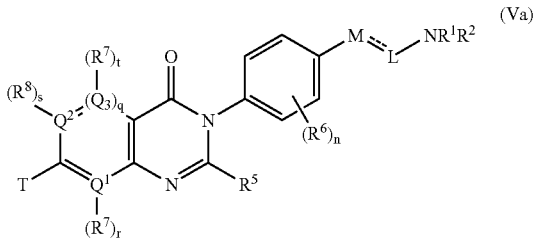

with a compound capable of introducing the group Ⓐ, and wherein Ⓐ, $R^8$, $R^7$, $R^6$, $R^5$, $R^2$, $R^1$, M, L, $Q^1$, $Q^2$, $Q^3$, q, r, s, t, and n are as defined in formula (Ia) and T is a leaving group.

Thus compounds of formula (Ia) may be prepared from the compound of formula (Va) with thea boronic acid and a palladium catalyst using a Suzuki coupling reaction or with an organostannane reagent and a palladium catalyst using a Stille coupling reaction.

Compounds of formula (Ia) wherein $R^5$ is hydrogen may also be prepared by reaction of a sulfur-containing compound such as VI with a reductant, such as Raney Nickel, in a solvent such as ethanol and wherein Ⓐ, $R^{8, R7}$, $R^6$, $R^5$, $R^2$, $R^1$, M, L, $Q^1$, $Q^2$, $Q^3$, q, r, s, t, and n are as defined in formula (Ia).

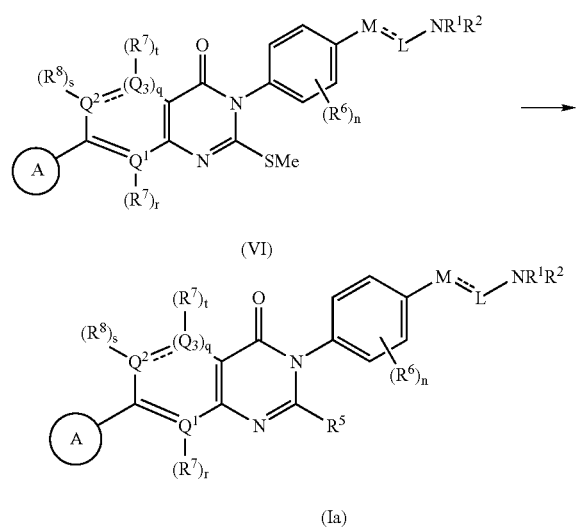

Compounds of formula (II) may be prepared by reduction of the corresponding nitro aromatic (VII) using hydrogen and a catalyst (e.g. 10% Pd on carbon), stannous chloride, or sodium dithionite

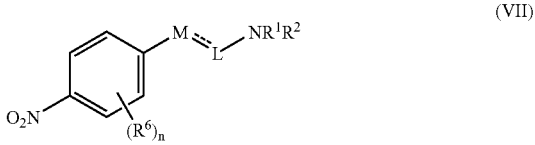

wherein $R^6$, M, L, $R^1$ and $R^2$, and n have the meanings defined in formula (Ia) or a group convertible thereto.

Compounds of formula VII wherein M is O and $R^6$, L, $R^1$, $R^2$, and n have the meanings defined in formula (Ia) can be prepared from halo aromatics (VIII) wherein X is chloro or fluoro and an alcohol of formula (IX) in the presence of a suitable base such as cesium carbonate, potassium carbonate or sodium hydride and a polar aprotic solvent such as DMF or DMSO and wherein Ⓐ, $R^8$, $R^7$, $R^6$, $R^5$, $R^2$, $R^1$, M, L, $Q^1$, $Q^2$, $Q^3$, q, r, s, t, and n are as defined in formula (Ia).

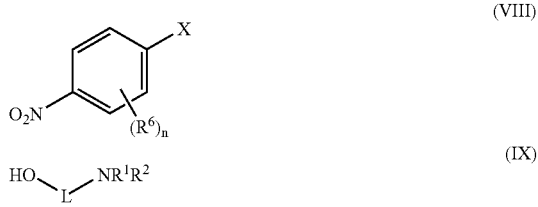

Alternatively, compounds of formula (VII) wherein M is O and $R^6$, L, $R^1$, $R^2$, and n have the meanings defined in formula (Ia) can be prepared from phenols of formula (X) and alcohols of formula (IX) via a Mitsunobu coupling.

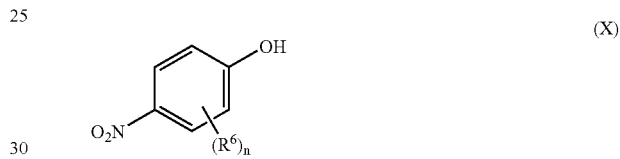

Alternatively, compounds of formula VII wherein M is O or S and $R^6$, L, $R^1$, $R^2$, and n have the meanings defined in formula (Ia) can be prepared from phenols of formula (X) and thiophenols of formula (XI) by alkylation with a compound of formula (XII) wherein T is a leaving group such as chloro, bromo, tosylate or mesylate.

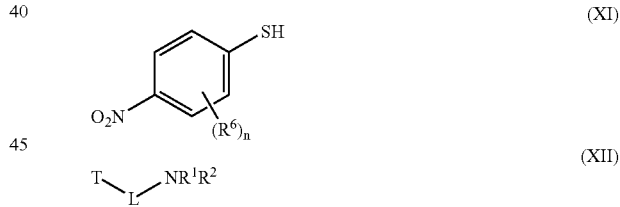

Compounds of formula (VII) wherein M is N and $R^6$, L, $R^1$, $R^2$, and n have the meanings defined in formula (Ia) can be prepared from halo aromatics (VIII) wherein X is chloro or fluoro and an amine of formula (XIII) in the presence of a base such as excess amine (XIII) or a trialkylamine.

Compounds of formula (VII) wherein M is $S(O)_2NR$ and $R^6$, L, $R^1$, $R^2$, and n have the meanings defined in formula (Ia) can be prepared by reaction of amine (XIII) with 4-nitrobenzenesulfonylchloride.

Compounds of formula (Ia) in which M is $N-S(O)_2R$ can be prepared by reaction of compounds of formula (Ia) in which M is NH with sulfonyl chlorides in the presence of a tertiary amine such as triethylamine. Compounds of formula (Ia) may be prepared by alkylation of an amine of formula (XV) with an alkylating agent of formula (XIV) wherein M is O, T is a leaving group and $R^1$ and $R^2$ have the meanings defined in formula (Ia).

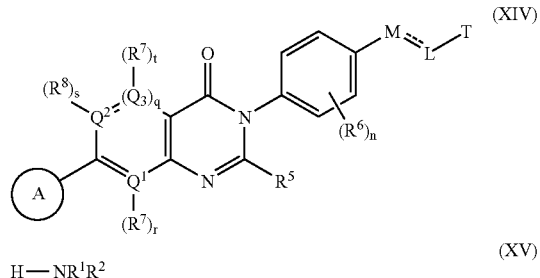

(XIV)

H—$NR^1R^2$ (XV)

Compounds of formula (Ia) in which M is N(CO)R can be prepared by acylation of aniline of general formula (XVI) by an acylating agent of formula (XVII) and wherein wherein $R^9$ is selected from the group consisting of hydrogen, phenyl, heteroaryl, $C_{1-6}$ straight or branched alkyl, and $C_{3-6}$ cycloalkyl.

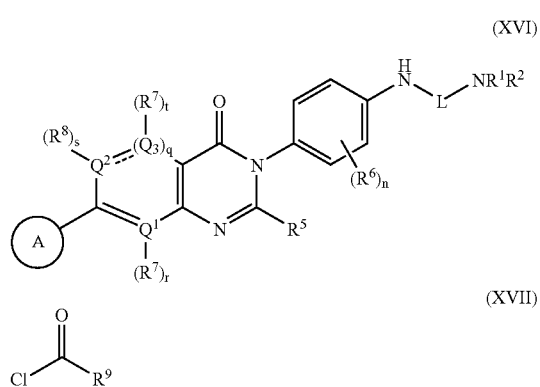

(XVI)

(XVII)

Compounds of formula (Ia) in which M is N can be prepared by reductive alkylation of aniline of general formula (XIX) by an aldehyde of formula (XVIII) in the presence of a borohydride reducing agent or hydrogen and a catalyst and in which the L of formula (XVIII) is $CH_2$ or $CH_2CH_2$ and wherein Ⓐ, $R^8$ $R^7$, $R^6$, $R^5$, $R^2$, $R^1$, M, $Q^1$, $Q^2$, $Q^3$, q, r, s, t, and n are as defined in formula (Ia).

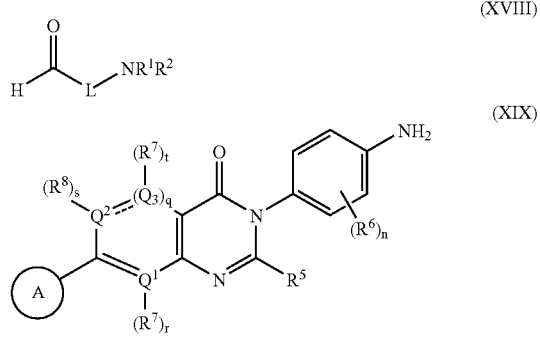

(XVIII)

(XIX)

Compounds of formula (Ia) in which M is O can be prepared by alkylation of a phenol of formula (XX) by an alkylating agent of formula (XXI) in which T is a leaving group and wherein Ⓐ, $R^8$, $R^7$, $R^6$, $R^5$, $R^2$, $R^1$, M, L, $Q^1$, $Q^2$, $Q^3$, q, r, s, t, and n are as defined in formula (Ia).

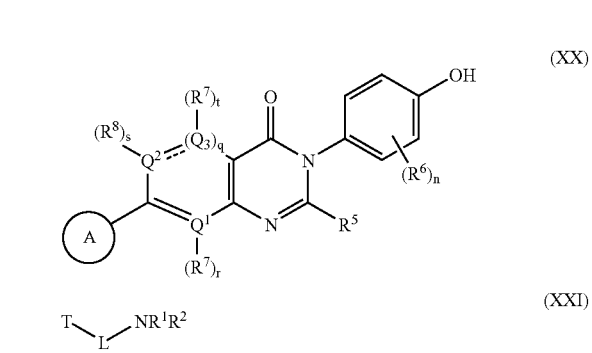

(XX)

(XXI)

Alternatively, compounds of this type can be made by reductive amination of an aldehyde of formula (XXII) by an amine of formula (XV) in the presence of a reducing agent such as a borohydride or hydrogen and a catalyst and wherein L is $CH_2$ or $CH_2CH_2$ and Ⓐ, $R^8$, $R^7$, $R^6$, $R^5$, $R^2$, $R^1$, M, $Q^1$, $Q^2$, $Q^3$, q, r, s, t, and n are as defined in formula (Ia).

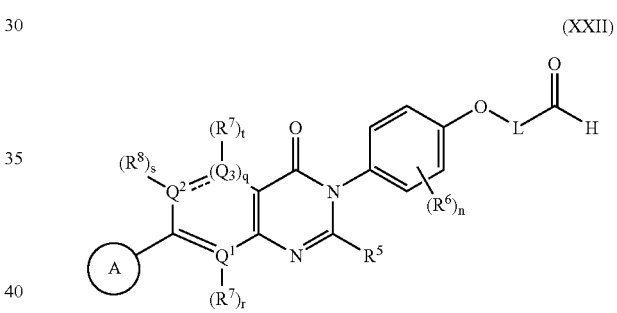

(XXII)

Compounds of formula (XXII) can be prepared by acid treatment of an acetal of formula (XXIII) in which $R^{10}$ is alkyl and wherein Ⓐ, $R^8$, $R^7$, $R^6$, $R^5$, $R^2$, $R^1$, M, L, $Q^1$, $Q^2$, $Q^3$, q, r, s, t, and n are as defined in formula (Ia).

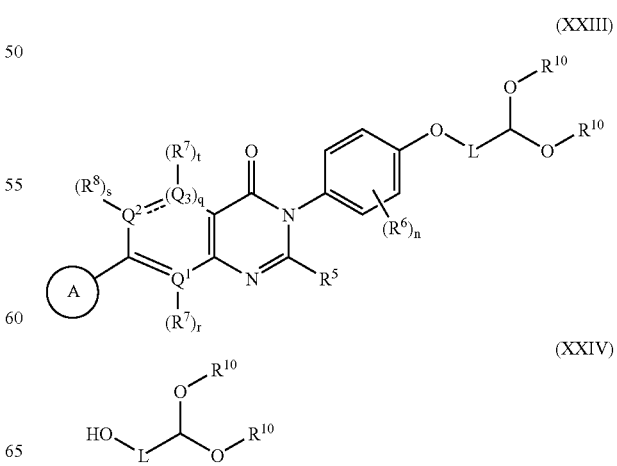

(XXIII)

(XXIV)

Compounds of formula (XXIII) can be made via alkylation of an alcohol of formula (XX) with a compound of formula (XXIII) followed by the protocol as hereinbefore described.

Compounds of formula (Ia) in which M is O and Ⓐ, $R^8$, $R^7$, $R^6$, $R^5$, $R^1$, M, $Q^1$, $Q^2$, $Q^3$, q, r, s, t, and n are as defined in formula (Ia) can be made by reductive alkylation of amines of formula (XXV) with an aldehyde and wherein for formula (XXV) G is H and Ⓐ, $R^8$, $R^7$, $R^6$, $R^5$, $R^2$, $R^1$, M, L, $Q^1$, $Q^2$, $Q^3$, q, r, s, t, and n are as defined in formula (Ia). Amines of formula (XXV) can be made by acid treatment of N-t-butoxycarbonyl protected derivatives of formula (XXVI) that in turn can be prepared by alkylation of alcohols of formula (XXVII) in which G is t-butoxycarbonyl with a compound of formula (VIII) followed by the protocol as hereinbefore described.

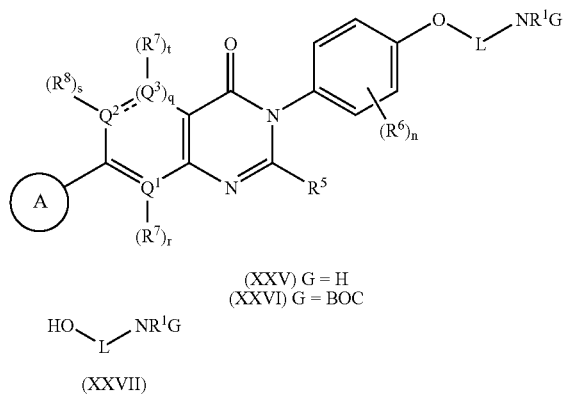

(XXV) G = H
(XXVI) G = BOC (XXVII)

Compounds of formula (Ia) in which L is —C(O)CH$_2$— can be prepared by reaction of an amine of formula (XV) with an alkylating agent of formula (XXVIII) in which T is a leaving group such as chloro or bromo and wherein Ⓐ, $R^8$, $R^7$, $R^6$, $R^5$, $R^2$, $R^1$, M, L, $Q^1$, $Q^2$, $Q^3$, q, r, s, t, and n are as defined in formula (Ia).

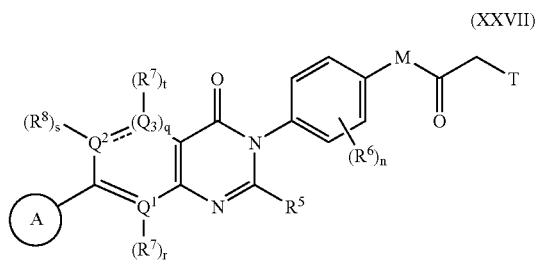

(XXVII)

The compounds of formula (Ia) are believed to have a role in the treatment of obesity and/or diabetes. Compounds of the present invention are antagonists of a MCHR1 and can be used for the treatment of a disease caused by or attributable to a melanin-concentrating hormone. Compounds of the invention may reduce hunger, suppress appetite, control eating, and/or induce satiety.

The present invention provides methods for the treatment of several conditions or diseases such as obesity, diabetes, depression (eg., major depression and/or bipolar disorder), and/or anxiety. Such treatment comprises the step of administering a therapeutically effective amount of the compound of formula (Ia), including a salt, solvate, or physiologically functional derivative thereof. Such treatment can also comprise the step of administering a therapeutically effective amount of a pharmaceutical composition containing a compound of formula (Ia), including a salt, solvate, or physiologically functional derivative thereof. As used herein, the term "treatment" refers to alleviating the specified condition, eliminating or reducing the symptoms of the condition, slowing or eliminating the progression of the condition, and preventing or delaying the reoccurrence of the condition in a previously afflicted patient or subject.

As used herein, the term "therapeutically effective amount" means an amount of a compound of formula (Ia) which is sufficient, in the subject to which it is administered, to elicit the biological or medical response of a cell culture, tissue, system, animal (including human) that is being sought, for instance by a researcher or clinician.

The precise therapeutically effective amount of the compounds of formula (Ia) will depend on a number of factors including, but not limited to, the age and weight of the subject being treated, the precise disorder requiring treatment and its severity, the nature of the formulation, and the route of administration, and will ultimately be at the discretion of the attendant physician or veterinarian. Typically, the compound of formula (Ia) will be given for treatment in the range of 0.1 to 200 mg/kg body weight of recipient (animal) per day and more usually in the range of 1 to 100 mg/kg body weight per day. Acceptable daily dosages, may be from about 0.1 to about 200 mg/day, and preferably from about 0.1 to about 100 mg/day.

The administration of compounds of the invention to an animal, particularly a mammal such as a human, may be by way of oral (including sub-lingual), parenteral, nasal, rectal or transdermal administration. Preferably oral administration is employed.

While it is possible that, for use in therapy, a therapeutically effective amount of a compound of formula (Ia) may be administered as the raw chemical, it is typically presented as the active ingredient of a pharmaceutical composition or formulation. Accordingly, the invention further provides a pharmaceutical composition comprising a compound of formula (Ia). The pharmaceutical composition may further comprise one or more pharmaceutically acceptable carriers, diluents, and/or excipients. The carrier(s), diluent(s), and/or excipient(s) must be acceptable in the sense of being compatible with the other ingredients of the formulation and not deleterious to the recipient thereof.

In accordance with another aspect of the invention there is also provided a process for the preparation of a pharmaceutical formulation including admixing a compound of formula (Ia) with one or more pharmaceutically acceptable carriers, diluents, and/or excipients.

Pharmaceutical formulations may be presented in unit dose form containing a predetermined amount of active ingredient per unit dose. Such a unit may contain a therapeutically effective dose of the compound of formula (Ia) or a fraction of a therapeutically effective dose such that multiple unit dosage forms might be administered at a given time to achieve the desired therapeutically effective dose. Preferred unit dosage formulations are those containing a daily dose of sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example, by the oral (including buccal or sublingual), rectal, nasal, topical (including buccal, sublingual, or transdermal), vaginal or parenteral (including subcutaneous, intramuscular, intravenous or intradermal) route. Such formulations may be prepared by any method know in the art of pharmacy, for example, by bringing into association the active ingredient with the carrier(s), diluent(s), and/or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions. For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent or dye can also be present.

Capsules are made by preparing a powder mixture as described above, and filling formed gelatin sheaths. Glidants and lubricants, such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators (disintegrents) include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granuated by wetting with a binder such as a syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into dablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of active ingredient. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like. The compound of formula (Ia) can also be incorporated into a candy, a wafer, and/or tongue tape formulation for administration as a "quick-dissolve" medicament.

Additionally, the present invention comprises a compound of formula (Ia) in combination with at least one specie selected from the group consisting of an agent for treating diabetes, an agent for treating hypertension, and an agent for treating arteriosclerosis.

The following examples are intended for illustration only and are not intended to limit the scope of the invention in any way, the invention being defined by the claims which follow.

Reagents are commercially available or are prepared according to procedures in the literature.

EXAMPLE H1

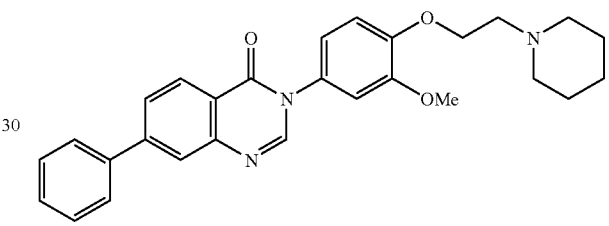

3-{3-methoxy-4-[2-(1-piperidinyl)ethoxy]phenyl}-7-phenyl-4(3H)-quinazolinone

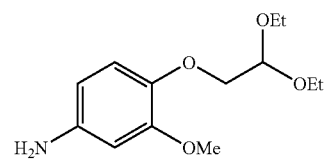

4-(2,2-diethoxyethoxy)-3-methoxyaniline

To a solution of 2,2-diethoxyethanol (50 mmol, 6.71 g) was added 60% sodium hydride (50 mmol, 2.0 g) and the solution was stirred for 10 minutes at which point a solution of 2-chloro-5-nitroanisole (50 mmol, 9.38 g) in DMF was added dropwise. The reaction mixture was stirred for 18 h. The DMF was removed by rotary evaporation. The residue was partitioned between ethyl acetate and water. The organic layer was washed with brine. The organic phase was dried over $Na_2SO_4$ and concentrated. The principal component was purified by silica gel column chromatography. The product was subjected to reduction over 18 h using 1 atm hydrogen and 10% Pd on carbon. After the reaction took up a theoretical amount of hydrogen the catalyst was removed by filtration.

The filtrate was concentrated giving the intermediate (5.21 g, 41%). $^1$H NMR (DMSO-D6): δ 1.12 (6H, t), 3.62-3.81 (9H, m), 4.73 (3H, m), 6.05 (1H, d, J=6.8 Hz), 6.25 (1H, d, J=1.8 Hz), 6.63 (1H, m). LCMS m/z=278 (m+Na+).

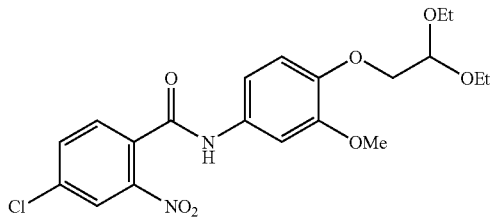

4-chloro-N-[4-(2,2-diethoxyethoxy)-3-methoxyphenyl]-2-nitrobenzamide

To a solution of 2-nitro-4-chlorobenzoic acid (5.09, 25.2 mmol) in DCM (100 mL) was added oxalyl chloride (16.8 mL, 34 mmol, 2M in DCM) and DMF (5 drops). The solution was stirred for 1 h and then concentrated by rotary evaporation. The resulting acid chloride was dissolved in DCM. To a solution of 4-(2,2-diethoxyethoxy)-3-methoxyaniline (5.36 g, 21 mmol), triethylamine (4.2 g) and DMAP (0.48 g) in DCM at 0° C. was added the acid chloride solution in 4 portions over 15 min. The reaction was stirred for 18 h and the ice was allowed to melt. The solvents were removed by rotary evaporation and the residue partitioned between water and ethyl acetate. The organic layer was washed with brine, dried and concentrated. The product was purified by by silica gel column chromatography affording the intermediate as a yellow solid (7.91 g, 86%). ¹H NMR (DMSO-D6): δ 1.18 (6H, t, J=6.9 Hz), 3.57 (2H, q, J=12.1 Hz), 3.67 (2H, q, J=12.2 Hz), 3.75 (s, 3H), 3.91 (2H, d, J=5.1 Hz), 4.79 (1H, t, J=5.1 Hz), 7.00 (1H, m), 7.18 (1H, d), 7.34 (1H, s), 7.82 (1H, d), 7.95 (1H, d), 8.26 (1H, s), 10.57 (1H, d). LCMS m/z=461 (m+Na+).

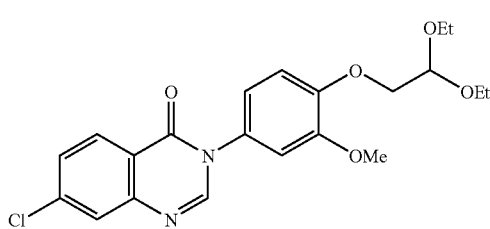

7-chloro-3-[4-(2,2-diethoxyethoxy)-3-methoxyphenyl]-4(3H)-quinazolinone

The intermediate from above (2.52 g, 5.74 mmol) was dissolved in dioxane (40 mL), water (40 mL) and ammonium hydroxide (8 mL). To this solution was added sodium hydrosulfite (Na₂S₂O₄,8 eq, 8.0 g). The reaction mixture was stirred for 20 min. The dioxane was removed by rotary evaporation. The aqueous solution was extracted with ethyl acetate. The organic layer was washed with brine and concentrated to give a white solid. The solid was added to triethylorthoformate (30 mL) and the mixture was heated at 100° C. for 16 h. The reaction mixture was allowed to cool and then partitioned between dilute aqueous sodium bicarbonate solution and ethyl acetate. The organic layer was concentrated on a rotary evaporator to give a residue that was triturated with petroleum ether. The solids were filtered affording pure product (1.90 g, 79%). ¹H NMR (DMSO-D6): δ 1.15 (6H, t, J=7.1 Hz), 3.60 (2H, q, J=12.2 Hz), 3.69 (2H, q, J=12.3 Hz), 3.79 (s, 3H), 4.00 (2H, d, J=5.2 Hz), 4.85 (1H, t, J=5.2 Hz), 7.05 (1H, m), 7.15 (1H, d, J=8.5 Hz), 7.20 (1H, d, J=2.0 Hz), 7.64 (1H, dd), 7.82 (1H, d, J=1.7 Hz), 8.20 (1H, d, J=8.6 Hz), 8.37 (1H, s). LCMS m/z=419 (m+H+).

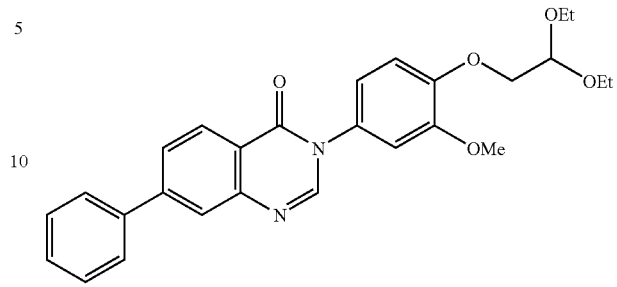

3-[4-(2,2-diethoxyethoxy)-3-methoxyphenyl]-7-phenyl-4(3H)-quinazolinone

The aryl chloride from the preceding step (0.80 g, 1.92 mmol), phenyl boronic acid (0.35 g, 1.5 eq), bis-t-butylbiphenylphosphine (114 mg, 20 mol %), palladium acetate (46 mg, 10 mol %) and potassium fluoride (0.334 g, 1 eq) were added to a dry round bottom flask. To this was added degassed dioxane (20 mL) and di-isopropylethylamine (0.32 mL). The reaction mixture was heated at 70° C. for 3 h. The reaction mixture was diluted with ether, washed with 1N NaOH and with water. The aqueous washes were back extracted twice with ether. The organic portion was dried and concentrated. The product was purified by silica gel column chromatography to give the intermediate (0.36 g, 41%). ¹H NMR (DMSO-D6): δ 1.20 (6H, t), 3.60 (2H, q, J=12.2 Hz), 3.70 (2H, q, J=12.3 Hz), 3.80 (s, 3H), 4.02 (2H, d, J=5.1 Hz), 4.85 (1H, t, J=5.0 Hz), 7.05 (1H, m), 7.04-7.22 (3H, m), 7.45-7.58 (3H, m), 7.83-7.94 (4H, m), 8.27 (d, J=8.4 Hz), 8.36 (1H, s). LCMS m/z=461 (m+H+).

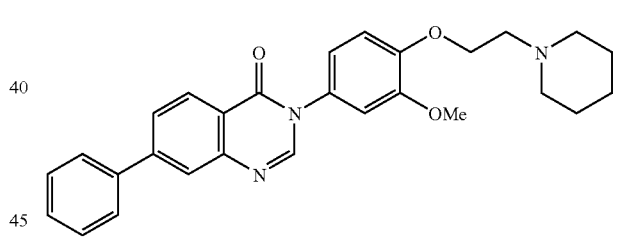

3-{3-methoxy-4-[2-(1-piperidinyl)ethoxy]phenyl}-7-phenyl-4(3H)-quinazolinone

To a solution of the diethyl acetal from the preceding step (30 mg, 0.065 mmol) was added DCM (5 mL) and TFA (1 mL). The solution was stirred for 15 min and the solvents were removed by rotary evaporation. The residue was dissolved in THF (3 mL). To this solution was added piperidine (16 mg, 3 eq), and sodium triacetoxyborohydride (41 mg, 3 eq). The reaction mixture was stirred for 18 h. The solvents were removed and the residue partitioned between ethylacetate and aqueous sodium carbonate solution. The organic layer was dried and concentrated. The product was purified by silica gel column chromatography affording the title compound (30 mg, 76%). ¹H NMR (DMSO-D₆) δ 1.20 (1H, m), 1.63 (1H, m), 1.85 (1H, m), 2.02 (4H, m), 3.20 (2H, m), 3.40 (2H, m),3.79 (1H, m), 3.90 (3H, s), 4.64 (2H, m), 7.01 (2H, m), 7.10 (1H, d, J=7.2 Hz), 7.54 (3H, m), 7.73-7.78 (3H, m), 8.00 (s, 1H), 8.15 (s, 1H), 8.44 (1H, d, J=8.2 Hz). LCMS m/z=456 (m+H+).

Examples H2-H15 were prepared according to the procedures described in Example H1.

EXAMPLE H2

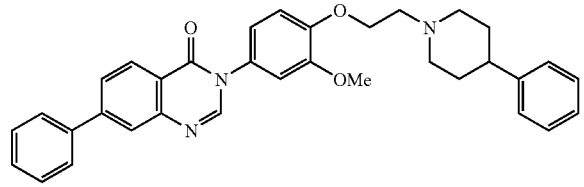

3-{3-methoxy-4-[2-(4-phenyl-1-piperidinyl)ethoxy]phenyl}-7-phenyl-4(3H)-quinazolinone $^1$H NMR (DMSO-D$_6$) δ 2.01 (3H, m), 2.60 (2H, m), 3.02 (2H, m), 3.58 (2H, m), 3.90 (5H, m), 4.72 (2H, m), 6.98 (2H, m), 7.02 (1H, m), 7.28 (5H, m), 7.50 (3H,m), 7.74 (1H, d, J=7.1 Hz), 7.79 (1H, d, J=2.0 Hz), 7.85 (1H, d, J=8.3 Hz), 8.07 (1H,s), 8.30 (1H, m), 8.45 (1H, d, J=8.4 Hz). LCMS m/z=532 (m+H+).

EXAMPLE H3

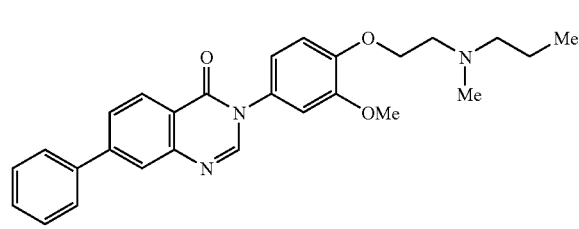

3-(3-methoxy-4-{2-[methyl(propyl)amino]ethoxy}phenyl)-7-phenyl-4(3H)-quinazolinone $^1$H NMR (DMSO-D$_6$) δ 0.85 (3H, t, J=7.2 Hz), 1.51 (2H, m), 2.38 (4H, m), 2.89 (3H, br s), 3.80 (3H, s), 4.17 (2H, br s), 7.15 (3H, m), 7.56 (3H, m), 7.86 (3H, m), 8.36 (3H, m). LCMS m/z=444 (m+H+).

EXAMPLE H4

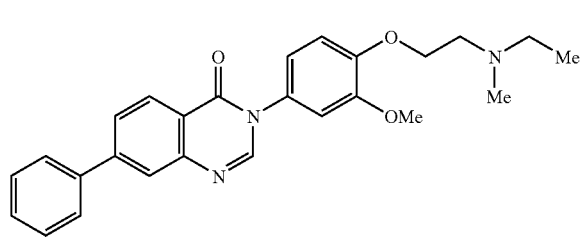

3-(4-{2-[ethyl(methyl)amino]ethoxy}-3-methoxyphenyl)-7-phenyl4(3H)-quinazolinone $^1$H NMR (DMSO-D$_6$) δ 1.08 (3H, t, J=7.1 Hz), 2.20 (3H, br s), 3.32 (2H, m), 3.44 (2H, m), 3.80 (3H, s), 4.21 (2H, brs), 7.16 (3H, m), 7.51 (3H, m), 7.86 (3H, m), 8.01 (1H, s), 8.27 (1H, d, J=8.4 Hz), 8.36 (1H, s). LCMS m/z=430 (m+H+).

EXAMPLE H5

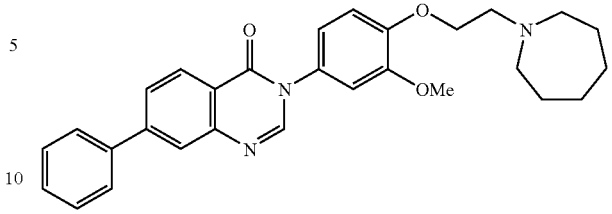

3-{4-[2-(1-azepanyl)ethoxy]-3-methoxyphenyl}-7-phenyl-4(3H)-quinazolinone $^1$H NMR (DMSO-D$_6$) δ 1.22 (4H, m), 1.60 (6H, m), 2.82 (4H, m), 3.09 (2H, m), 3.80 (3H, s), 4.14 (2H, br s), 7.14 (3H, m), 7.56 (3H, m), 7.92 (3H, m), 8.20 (1H, d, J=8.6 Hz), 8.27 (1H, d, J=8.3 Hz), 8.36 (1H, s). LCMS m/z=470 (m+H+).

EXAMPLE H6

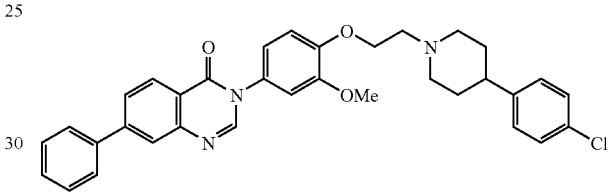

3-(4-{2-[4-(4-chlorophenyl)-1-piperidinyl]ethoxy}-3-methoxyphenyl)-7-phenyl-4(3H)-quinazolinone $^1$H NMR (CDCl$_3$) δ 2.00 (2H, m), 2.32 (2H, m), 2.70 (1H, m), 2.88 (2H, m), 3.44 (2H, m), 3.75 (2H, m), 3.90 (3H, s), 4.52 (2H, br s), 6.92-7.07 (4H, m), 7.29 (2H, m), 7.32 (2H, m), 7.53 (2H, m), 7.73 (2H, m), 8.00 (1H, s), 8.17 (1H, d, J=11.6 Hz), 8.30 (1H, d, J=8.5 Hz), 8.42 (1H, d, J=8.3 Hz). LCMS m/z =566 (m+H+).

EXAMPLE H7

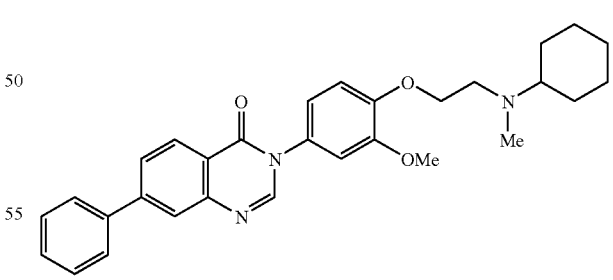

3-(4-{2-[cyclohexyl(methyl)amino]ethoxy}-3-methoxyphenyl)-7-phenyl-4(3)-quinazolinone $^1$H NMR (CDCl$_3$) δ 1.15-2.35 (C$_6$H$_{11}$), 2.90 (3H, s), 3.55 (2H, m), 3.89 (3H, s), 4.61 (2H, br s), 6.99 (2H, m), 7.10 (1H, d, J=8.2 Hz), 7.53 (3H, m), 7.73-7.83 (3H, m), 8.00 (1H, d, J=1.3 Hz), 8.20 (1H, s), 8.42 (1H, d, J=8.4H,z). LCMS m/z=484 (m+H+).

EXAMPLE H8

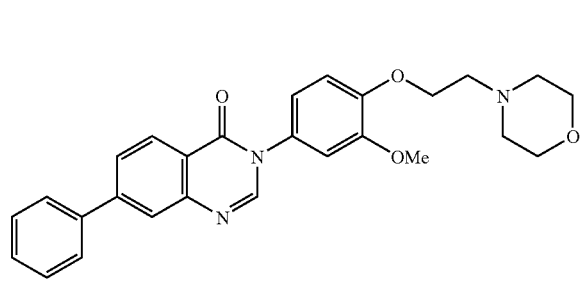

3-{3-methoxy-4-[2-(4-morpholinyl)ethoxy]phenyl}-7-phenyl-4(3H)-quinazolinone $^1$H NMR (CDCl$_3$) δ 3.21 (2H, m), 3.58 (2H, br s), 3.74 (2H, m), 3.90 (3H, s), 4.05 (2H, m), 4.32 (2H, t), 4.71 (2H, br s), 6.99 (2H, m), 7.10 (1H, d, J=8.2 Hz), 7.44-7.56 (3H, m), 7.75 (2H, m), 7.81 (1H, dd, J=8.3 Hz, J'=1.5 Hz), 8.02 (1H, s), 8.19 (1H, s), 8.41 (1H, d, J=8.5 Hz). LCMS m/z=458 (m+H+).

EXAMPLE H9

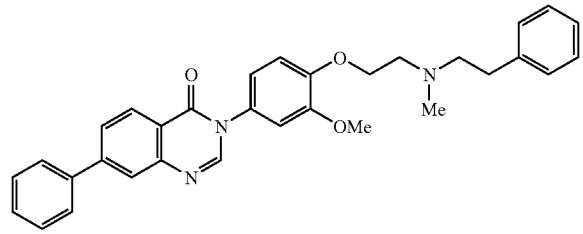

3-(3-methoxy-4-{2-[methyl(2-phenylethyl)amino]ethoxy}phenyl)-7-phenyl-4(3H)-quinazolinone $^1$H NMR (CDCl$_3$) δ 2.99 (3H, s), 3.22 (2H, m), 3.38 (2H, m), 3.51 (2H, t, J=4.7 Hz), 3.82 (3H, s), 4.54 (2H, t, J=4.7 Hz), 6.99 (2H, m), 7.10 (1H, d, J=8.2 Hz), 7.26-7.36 (5H, m), 7.44-7.56 (3H, m), 7.75 (2H, m), 7.82 (1 H, dd, J=8.3 Hz, J'=1.6 Hz), 8.01 (1H, d, J=1.5 Hz), 8.17 (1H, s), 8.42 (1H, d, J=8.2 Hz). LCMS m/z=506 (m+H+).

EXAMPLE H10

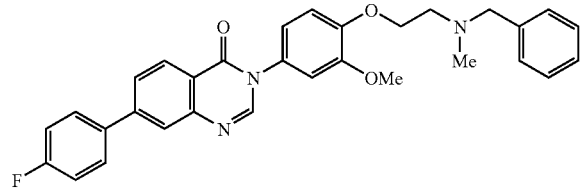

3-(4-{2-[benzyl(methyl)amino]ethoxy}-3-methoxyphenyl)-7-(4-fluorophenyl)-4(3H)-quinazolinone

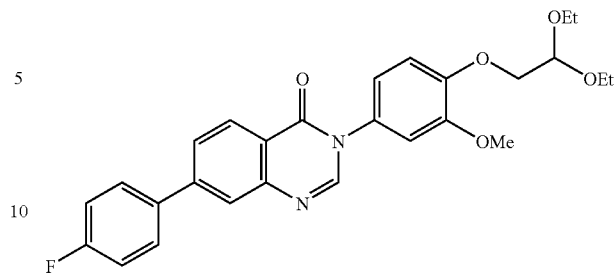

3-[4-(2,2-diethoxyethoxy)-3-methoxyphenyl]-7-(4-fluorophenyl)-4(3H)-quinazolinone $^1$H NMR (DMSO-D6) δ 1.08 (6H, t), 3.59-3.65 (4H, m), 3.80 (3H, s), 4.02 (2H, d), 4.85 (1H, t, J=5.1 Hz), 7.03-7.16 (3H, m), 7.38 (2H, m), 7.92 (3H, m), 8.00 (1H, s), 8.26 (1H, d, J=8.4 Hz), 8.36 (1H, s). LCMS m/z=501 (m+Na+).

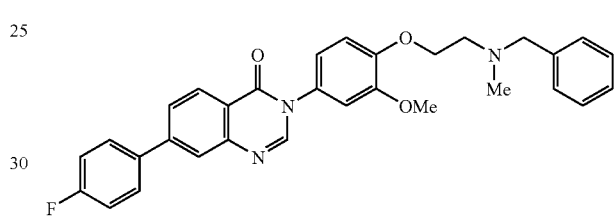

3-(4-{2-[benzyl(methyl)amino]ethoxy}-3-methoxyphenyl)-7-(4-fluorophenyl)-4(3H)-quinazolinone $^1$H NMR (DMSO-D6) δ 2.75 (3H, s), 3.37 (2H, s), 3.91 (3H, s), 4.25 (2H, s), 4.55 (2H, s), 6.96-7.09 (3H, m), 7.20-7.28 (2H, m), 7.44 (3H, m), 7.63-7.77 (5H, m), 7.95 (1H, d, J=1.5 Hz), 8.17 (1H, s), 8.42 (1H, d, J=8.3 Hz). LCMS m/z=510 (m+H+).

EXAMPLE H11

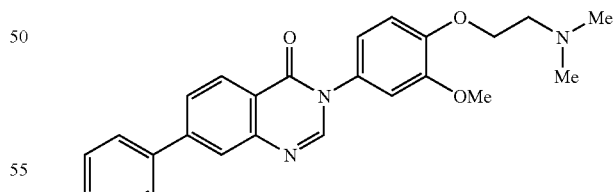

3-{4-[2-(dimethylamino)ethoxy]-3-methoxyphenyl}-7-(4-fluorophenyl)-4(3H)-quinazolinone $^1$H NMR (DMSO-D6) δ 2.51 (6H, s), 3.44 (2H, s), 3.79 (3H, s), 4.35 (2H, br s), 7.04-7.20 (3H, m), 7.38 (2H, m), 7.91-8.01 (4H, m), 8.27 (1H, d, J=8.2 Hz), 8.36 (1H, s). LCMS m/z=434 (m+H+).

EXAMPLE H12

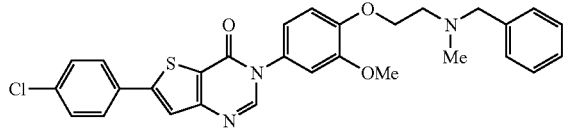

3-(4-{2-[benzyl(methyl)amino]ethoxy}-3-methoxyphenyl)-6-(4-chlorophenyl)thieno[3,2-d]pyrimidin-4(3H)-one

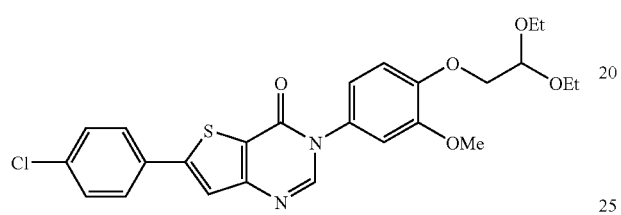

6-(4-chlorophenyl)-3-[4-(2,2-diethoxyethoxy)-3-methoxyphenyl]thieno[3,2-d]pyrimidin-4(3H)-one.

To a solution of methyl 3-amino-5-(4-chlorophenyl)-2-thiophenecarboxylate (2.0 g, 7.47 mmol, Maybridge, Inc) in ethanol (20 mL) was added dimethylformamide dimethyl acetal (2.5 mL, 2.5 eq, Aldrich). The reaction mixture was refluxed in a 90° C. oil bath for 3 h at which point the solvents were removed by rotary evaporation. Coevaporation with toluene removed the excess dimethylformamide dimethyl acetal. To the resulting residue was added ethanol (20 mL) and 4-(2,2-diethoxyethoxy)-3-methoxyaniline (2.3 g, 1.2 eq, Example H1). The reaction mixture was heated to 100° C. for 36 hours. The solvent was removed by rotary evaporation and the product purified by column chromatography followed by recrystallization from hot MeOH yielding the intermediate (0.82 g, 22%). $^1$H NMR (CDCl$_3$) δ 1.22 (6H, t), 3.63-3.83 (4H, m), 3.90 (3H, s), 4.14 (2H, d, J=5.3 Hz), 4.92 (1H, t, J=5.2 Hz), 6.97 (2H), 7.06 (1H, d, J=8.5 Hz), 7.46 (2H, d, J=8.5 Hz), 7.58 (1H, s), 7.68 (2H, d, J=8.4 Hz), 8.24 (1H, br, s). LCMS m/z=501 (m+H+).

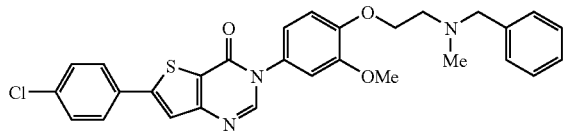

3-(4-{2-[benzyl(methyl)amino]ethoxy}-3-methoxyphenyl)-6-(4-chlorophenyl)thieno[3,2-d]pyrimidin-4(3H)-one.

Reductive amination of the product from the preceding step with N-methyl-N-benzylamine according to the procedure described in Example H1 provided the title compound.
$^1$H NMR (CDCl$_3$) δ 2.89 (2H, m), 3.90 (3H, s), 4.43 (2H, m), 4.68 (2H, m), 7.02 (2H), 7.10 (1H, d, J=8.5 Hz), 7.28 (2H, s), 7.48 (4H, m), 7.48 (1H, s), 7.67 (2H, d, J=8.3 Hz), 7.73 (1H, m), 8.19 (s, 1H). LCMS m/z=532 (m+H+).

Examples H13-H15 were Prepared According to the Procedures Described in Example H12.

EXAMPLE H13

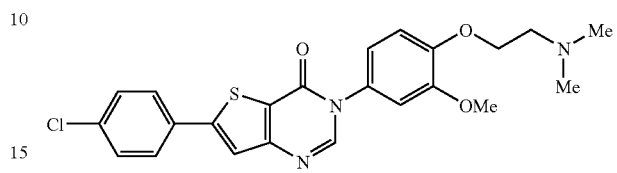

6-(4-chlorophenyl)-3-{4-[2-(dimethylamino)ethoxy]-3-methoxyphenyl}thieno[3,2-d]pyrimidin-4(3H)-one $^1$H NMR (CDCl$_3$) δ 3.03 (6H, s), 3.90 (3H, s), 3.78 (2H, m), 3.91 (3H, s), 4.63 (2H, m), 7.01 (2H, m), 7.11 (1H, d, J=8.3 Hz), 7.48 (2H, d, J=8.6 Hz), 7.61 (1H, s), 7.68 (2H, d, J=8.6 Hz), 8.26 (1H, s). LCMS m/z=456 (m+H+).

EXAMPLE H14

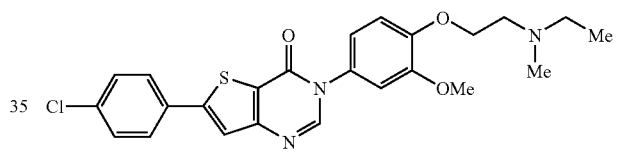

6-(4-chlorophenyl)-3-(4-{2-[ethyl(methyl)amino]ethoxy}-3-methoxyphenyl)thieno[3,2-d]pyrimidin-4(3H)-one $^1$H NMR (CDCl$_3$) δ 1.54 (5H, m), 2.97 (3H, s), 3.51 (2H, m), 3.90 (3H, s), 4.66 (2H, m), 6.98 (2H, m), 7.11 (1H, d, J=8.4 Hz), 7.48 (2H, d, J=8.6 Hz), 7.56 (1H, s), 7.68 (2H, d, J=8.4 Hz), 8.15 (1H, s). LCMS m/z=470 (m+H+).

EXAMPLE H15

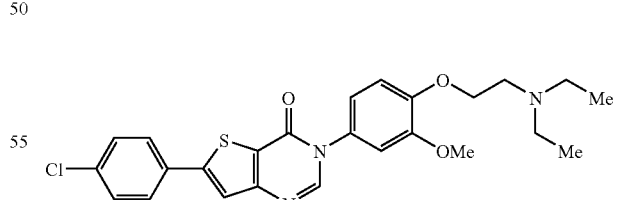

6-(4-chlorophenyl)-3-{4-[2-(diethylamino)ethoxy]-3-methoxyphenyl}thieno[3,2-d]pyrimidin-4(3H)-one $^1$H NMR (CDCl$_3$) δ 1.54 (6H, m), 3.027 (4H, m), 3.61 (2H, m), 3.89 (3H, s), 4.55 (2H, m), 6.99 (2H, m), 7.11 (1H, d, J=8.4 Hz), 7.47 (2H, d, J=8.4 Hz), 7.58 (1H, s), 7.68 (2H, d, J=8.5 Hz), 8.21 (1H, s). LCMS m/z=484 (m+H+).

EXAMPLE H16

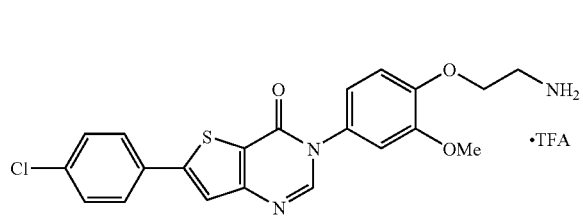

3-[4-(2-aminoethoxy)-3-methoxyphenyl]-6-(4-chlorophenyl)thieno[3,2-d]pyrimidin-4(3H)-one trifluoroacetate salt

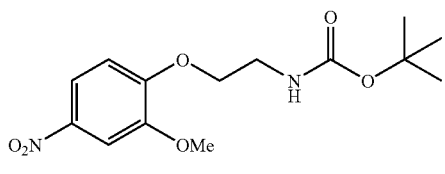

tert-butyl 2-(2-methoxy-4-nitrophenoxy)ethylcarbamate

To a solution of 4-nitroguiacol (5.0 g, 30 mmol), tert-butyl-2-hydroxyethylcarbamate (5.3 g, 33 mmol) and triphenylphosphine (9.8 g, 37.5 mmol) in THF (50 mmol) was added dropwise diisopropylazodicarboxylate (7.4 mL, 37.5 mmol). The reaction mixture was stirred for 1 day. The solvent was removed by rotary evaporation and the residue was dissolved in chloroform and loaded onto a silica gel column. The product was eluted with 50% ethylacetate in petroleum ether giving the product as a white solid. $^1$H NMR (CDCl$_3$) δ 1.46 (9H, s), 3.63 (2H, dd, J=5.4 Hz, J'=10.2 Hz), 3.96 (3H, s), 4.17 (2H, dd, J=5.3 Hz, J'=10.4 Hz), 6.95 (1H, d, J=8.9 Hz), 7.76 (1H, d, J=2.6 Hz), 7.90 (1H, dd, J=9.0 Hz, J'=2.6 Hz). LCMS m/z=335 (m+Na+).

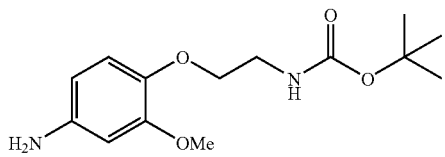

tert-butyl 2-(4-amino-2-methoxyphenoxy)ethylcarbamate

The material from the preceding step was dissolved in ethanol and subjected to reduction with 1 atm hydrogen and catalytic 10% Pd on carbon dust. The mixture was stirred overnight. The catalyst was removed by filtration and the filtrate was concentrated and the product purified by silica gel column chromatography giving the product (5.7 g, 68% yield). $^1$H NMR (CDCl$_3$) δ 1.46 (9H, s), 3.49 (2H, m), 3.83 (3H, s), 4.01 (2H, m), 5.30 (2H, br s), 6.60 (2H, m), 6.80 (1H, d, J=8.4 Hz), LCMS m/z=305 (m+Na+).

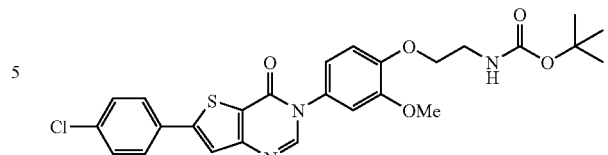

tert-butyl 2-[4-(6(4-chlorophenyl)-4-oxothieno[3,2-d]pyrimidin-3(4H)-yl)-2-methoxyphenoxy]ethylcarbamate $^1$H NMR (CDCl$_3$) δ 1.48 (9H, s), 3.62 (2H, m), 3.92 (3H, s), 4.16 (2H, m), 5.15 (1H, br s), 6.93-7.08 (3H, m), 7.47 (1H, d, J=8.4 Hz), 7.56 (1H, s), 7.68 (1H, d, J=8.6 Hz), 8.16 (1H, s). LCMS m/z=550 (m+Na+). Calcd: C, 59.14; H, 4.96; N, 7.96. Found: C, 58.85; H, 5.03; N, 7.85.

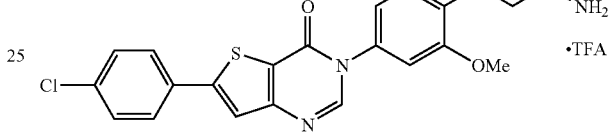

3-[4-(2-aminoethoxy)-3-methoxyphenyl]-6-(4-chlorophenyl)thieno[3,2-d]pyrimidin-4(3H)-one trifluoroacetate salt To the material from the preceding step (100 mg, 0.19 mmol) was added DCM (1 mL) and trifluoroacetic acid (1 mL). The reaction mixture was stirred for 20 min and the solvents removed by rotary evaporation and the residue pumped under a high vacuum. This yielded the title compound as a tan solid (105 mg, 100% yield). $^1$H NMR (CDCl$_3$) δ 3.27 (2H, m), 3.82 (3H, s), 4.24 (2H, m), 7.09-7.29 (3H, m), 7.61 (1H, d, J=8.5 Hz), 7.09-8.03 (3H, m), 8.41 (1H, s). LCMS m/z=428 (m+H+).

EXAMPLE H17

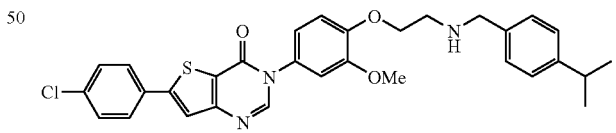

6-(4-chlorophenyl)-3-(4-{2-[(4-isopropylbenzyl)amino]ethoxy}-3-methoxyphenyl)thieno[3,2-d]pyrimidin-4(3H)-one The title compound from Example H16 (30 mg, 0.055 mmol) was dissolved in DMF (1 mL). To this solution was added 4-isopropylbenzaldehyde (10 mg, 1.2 eq) and sodium triacetoxyborohydride (23 mg, 2 eq). The reaction mixture was stirred 18 h and then loaded onto a silica gel column.

The product eluted with 20% ethanol/DCM giving the title compound (12 mg, 40%). $^1$H NMR (CDCl$_3$) δ 1.25 (6H, d), 2.90 (1H, m), 3.22 (2H, m), 3.85 (3H, s), 4.36 (2H, m), 6.91-7.09 (3H, m), 7.25 (3H, m), 7.46 (3H, m), 7.53 (1H, s). 7.67 (2H, m), 8.14 (1H, s). LCMS m/z=560 (m+H+).

EXAMPLE H18

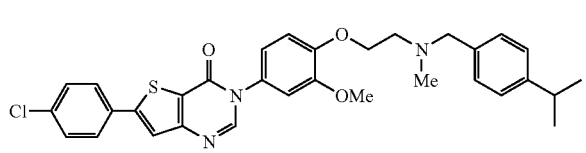

6-(4-chlorophenyl)-3-(4-{2-[(4-isopropylbenzyl)(methyl)amino]ethoxy}-3-methoxyphenyl)thieno[3,2-d]pyrimidin-4(3H)-one The product from Example H17 (12 mg) was dissolved in 37% formaldehyde (1 mL) and 88% formic acid (1 mL). The solution was refluxed for 2 h. The solvents were removed by rotary evaporation and the product was purified by silica gel column chromatography giving the title compound (10 mg, 81%). $^1$H NMR (CDCl$_3$) δ 1.25 (6H, d), 2.40 (3H, s), 2.90 (2H, m), 3.65 (2H, m), 3.90 (3H, s), 4.21 (2H, m), 6.91-7.00 (3H, m), 7.19-7.34 (4H, m), 7.46 (2H, d, J=8.4 Hz). 7.55 (1H, s), 7.68 (2H, d, J=8.6 Hz), 8.15 (1H, s). LCMS m/z=574 (m+H+).

Examples H19-H24 were Prepared According to the Procedures for H17 and H18.

EXAMPLE H19

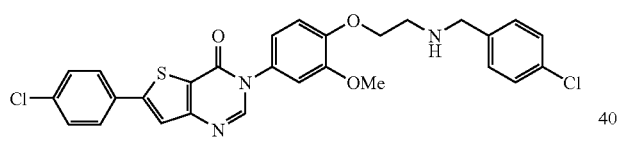

3-(4-{2-[(4-chlorobenzyl)amino]ethoxy}-3-methoxyphenyl)-6-(4-chlorophenyl)thieno[3,2-d]pyrimidin-4(3H)-one $^1$H NMR (CDCl$_3$) δ 3.85 (2H, m), 3.95 (3H, s), 4.36 (2H, m), 4.43 (2H, m), 6.91-7.17 (3H, m), 7.28-7.53 (5H, m), 7.57-7.84 (4H, m), 8.26 (1H, s). LCMS m/z=552 (m+H+).

EXAMPLE H20

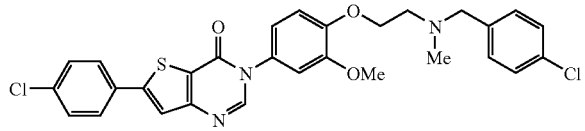

3-(4-{2-[(4-chlorobenzyl)(methyl)amino]ethoxy}-3-methoxyphenyl)-6-(4-chlorophenyl)thieno[3,2-d]pyrimidin-4(3H)-one $^1$H NMR (CDCl$_3$) δ 2.38 (3H, s), 2.92 (2H, t, J=6.1 Hz), 3.64 (2H, s), 3.90 (3H, s), 4.21 (2H, t, J=6.1 Hz), 6.96 (3H, m), 7.32 (4H, m), 7.46 (2H, d, J=8.6 Hz). 7.55 (1 H. s), 7.68 (2H, d, J=8.6 Hz), 8.16 (1H, s). LCMS m/z=566 (m+H+).

EXAMPLE H21

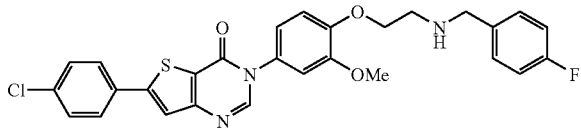

6-(4-chlorophenyl)-3-(4-{2-[(4-fluorobenzyl)amino]ethoxy}-3-methoxyphenyl)thieno[3,2-d]pyrimidin4(3H)-one $^1$H NMR (CDCl$_3$) δ 2.10 (2H, s), 3.28 (2H, m), 3.83 (3H, s), 4.13 (2H, s), 4.30 (2H, m), 6.91-7.12 (5H, m), 7.44-7.53 (5H, m), 7.66 (2H, d, J=8.6 Hz), 8.12 (1H, s). LCMS m/z=558 (m+Na+).

EXAMPLE H22

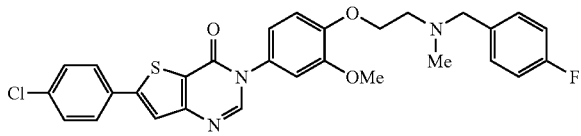

6-(4-chlorophenyl)-3-(4-{2-[(4-fluorobenzyl)(methyl)amino]ethoxy}-3-methoxyphenyl)thieno[3,2-d]pyrimidin-4(3H)-one $^1$H NMR (CDCl$_3$) δ 2.39 (3H, s), 2.95 (2H, t, J=6.1 Hz), 3.67 (2H, s), 3.90 (3H, s), 4.22 (2H, t, J=6.1 Hz), 6.91-7.06 (5H, m), 7.32 (2H, m), 7.46 (2H, d, J=8.6 Hz). 7.55 (1H, s), 7.68 (2H, d, J=8.6 Hz), 8.16 (1H, s). LCMS m/z=550 (m+H+).

EXAMPLE H23

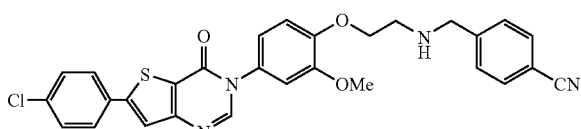

4-[({2-[4-(6-(4-chlorophenyl)-4-oxothieno[3,2-d]pyrimidin-3(4H)-yl)-2-methoxyphenoxy]ethyl}amino)methyl]benzonitrile $^1$H NMR (CDCl$_3$) δ 3.10 (2H, d, J=5.1 Hz), 3.90 (3H, s), 3.98 (2H, s), 4.22 (2H, d. J=5.1 Hz), 6.93-7.05 (3H, m), 7.46-7.56 (5H, m), 7.67 (3H, m), 8.16 (1H, s). LCMS m/z=565 (m+Na+).

EXAMPLE H24

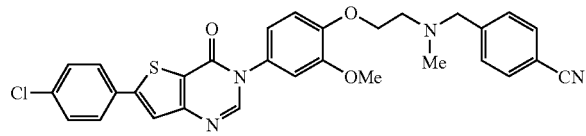

4-{[{2-[4-(6-(4-chlorophenyl)-4-oxothieno[3,2-d]
pyrimidin-3(4H)-yl)-2-methoxyphenoxy]ethyl}(methyl)amino]methyl}benzonitrile $^1$H NMR (CDCl$_3$) δ 2.38 (3H, s), 2.95 (2H, t, J=5.9 Hz), 3.73 (2H, s), 3.90 (3H, s), 4.22 (2H, t, J=6.0 Hz), 6.93-7.01 (3H, m), 7.45-7.56 (5H, m), 7.62-7.71 (4H, m), 8.16 (1H, s). LCMS m/z=579 (m+Na+).

EXAMPLE H25

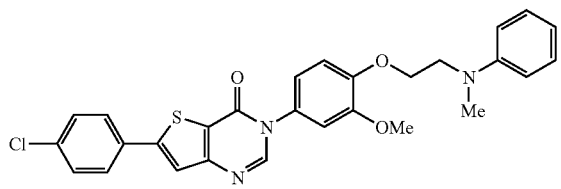

6-(4-chlorophenyl)-3-{3-methoxy-4-[2-(methylanilino)ethoxy]phenyl}thieno[3,2-d]pyrimidin-4(3H)-one To a solution of 6-(4-chlorophenyl)-3-(4-hydroxy-3-methoxyphenyl)thieno[3,2-d]pyrimidin-4(3H)-one (96 mg, 0.25 mmol, the preparation of which may be found in Example K1) in DMF was added 2-(methylanilino)ethyl toluenesulfonate (153 mg, 0.50 mmol) and cesium carbonate (0.24 g, 0.75 mmol) and the mixture was stirred with heating at 75° C. for 12 h. The reaction was allowed to cool and a 10 mL solution of 20% water/ethanol was added. The resulting precipitate was filtered and dried in a vacuum oven to give the title compound (104 mg, 80%). $^1$H NMR (DMSO-D6) δ 3.01 (3H, s), 3.78 (5H, m), 4.18 (2H, t, J=3.7 Hz), 6.63 (1H, t, J=7.3 Hz), 6.78 (2H, d, J=7.2 Hz), 7.02-7.20 (5H, m), 7.60 (2H, d, J=8.6 Hz), 7.96 (3H, m), 8.39 (1H, s). LCMS m/z=518 (m+H+). Calcd. for C$_{28}$H$_{24}$ClN$_3$O$_3$S×1H$_2$O: C, 62.74; H, 4.89; N, 7.84. Found: C, 62.76; H, 4.65; N, 7.82.

EXAMPLE H26

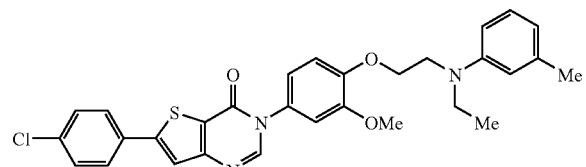

6-(4-chlorophenyl)-3-{4-[2-(ethyl-3-methylanilino)
ethoxy]-3-methoxyphenyl}thieno[3,2-d]pyrimidin-4
(3H)-one To a solution of 6-(4-chlorophenyl)-3-(4-hydroxy-3-methoxyphenyl)thieno[3,2-d]pyrimidin-4(3H)-one (96 mg, 0.25 mmol, the preparation of which can be found in the section detailing the preparation of Example K1) in DMF was added N-(2-chloroethyl)-N-ethyl-3-methylaniline (99 mg, 0.50 mmol) and cesium carbonate (0.24 g, 0.75 mmol) and the mixture was stirred with heating at 75° C. for 12 h. The reaction was allowed to cool and 10 mL solution of 20% water/ethanol was added. The resulting precipitate was filtered and dried in a vacuum oven to give the title compound (58 mg, 42%). $^1$H NMR (DMSO-D6) δ 1.13 (3H, t, J=7.0 Hz), 2.24 (3H, s), 3.45 (2H, q, J=7.0 Hz), 3.70 (2H, d, J=5.8 Hz), 3.79 (3H, s), 4.16 (2H, d, J=5.8 Hz), 6.43 (1H, t, J=7.3 Hz), 6.57 (2H, m), 7.02-7.20 (4H, m), 7.60 (2H, d, J=8.6 Hz), 7.96 (3H, m), 8.39 (1H, s). LCMS m/z=546 (m+H+).

EXAMPLE H27

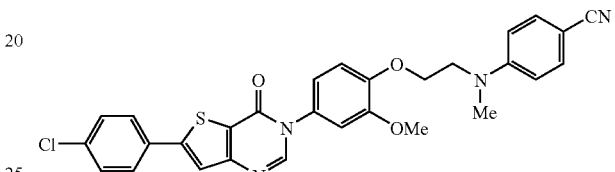

4-[{2-[4-(6-(4-chlorophenyl)-4-oxothieno[3,2-d]
pyrimidin-3(4H)-yl)-2-methoxyphenoxy]ethyl}
(methyl)amino]benzonitrile To a solution of 6-(4-chlorophenyl)-3-(4-hydroxy-3-methoxyphenyl)thieno[3,2-d]pyrimidin4(3H)-one (96 mg, 0.25 mmol, the preparation of which can be found in the section detailing the preparation of Example K1) in DMF was added 2-[4-cyano(methyl)anilino]ethyl p-toluenesulfonate (165 mg, 0.50 mmol) and cesium carbonate (0.24 g, 0.75 mmol) and the mixture was stirred with heating at 75° C. for 12 h. The reaction was allowed to cool and 10 mL solution of 20% water/ethanol was added. The resulting precipitate was filtered and dried in a vacuum oven to give the title compound (133 mg, 98%). $^1$H NMR (DMSO-D6) δ 3.10 (3H, s), 3.76 (3H, s), 3.87 (2H, t, J=3.7 Hz), 4.21 (2H, t, J=3.7 Hz), 6.87 (1H, d, J=7.3 Hz), 7.02-7.20 (3H, m), 7.58 (4H, m), 7.99 (3H, m), 8.38 (1H, s). LCMS m/z=543 (m+H+). Calcd. for C$_{29}$H$_{23}$ClN$_4$O$_3$S×1HCl: C, 60.11; H, 4.17; N; 9.67. Found: C, 59.78; H, 4.18; N, 9.44.

EXAMPLE H28

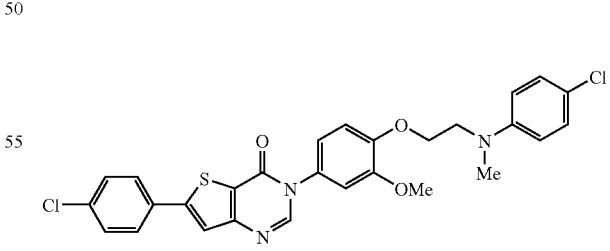

3-(4-{2-[4-chloro(methyl)anilino]ethoxy}-3-methoxyphenyl)-6-(4-chlorophenyl)thieno[3,2-d]pyrimidin-
4(3H)-one To a solution of 6-(4-chlorophenyl)-3-(4-hydroxy-3-methoxyphenyl)thieno[3,2-d]pyrimidin-4(3H)-one (96 mg, 0.25 mmol, the preparation of which can be found in the section detailing the preparation of Example K1) in DMF was added 2-[4-chloro(methyl)anilino]ethyl p-toluenesulfonate (170 mg, 0.50 mmol) and cesium carbonate (0.24 g, 0.75 mmol) and the mixture was stirred with heating at 75° C. for 12 h. The reaction was allowed to cool and 10 mL solution of 20% water/ethanol was added. The resulting precipitate was filtered and dried in a vacuum oven to give the title compound (136 mg, 98%). $^1$H NMR (DMSO-D6) δ 3.00 (3H, s), 3.77 (5H, m), 4.21 (2H, m), 6.81 (2H, d, J=9.0 Hz), 7.02-7.20 (5H, m), 7.58 (2H, d, J=8.6 Hz), 7.95 (3H, m), 8.39 (1H, s). Calcd. for $C_{28}H_{23}Cl_2N_3O_3S×3HCl$: C, 50.81; H, 3.96; N; 6.35. Found: C, 50.91; H, 3.95; N, 6.23.

EXAMPLE H29

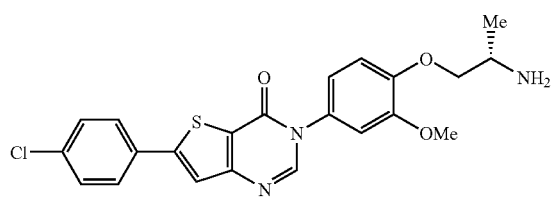

3-(4-{[(2S)-2-aminopropyl]oxy}-3-methoxyphenyl)-6-(4-chlorophenyl)thieno[3,2d]pyrimidin-4(3H)-one

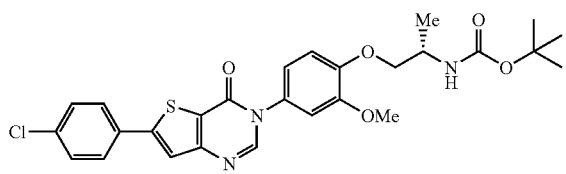

tert-butyl (1S)-2-[4-(6-(4-chlorophenyl)-4-oxothieno[3,2-d]pyrimidin-3(4H)-yl)-2-methoxyphenoxy]-1-methylethylcarbamate To a solution of 6-(4-chlorophenyl)-3-(4-hydroxy-3-methoxyphenyl)thieno[3,2-d]pyrimidin4(3H)-one (0.29 g, 0.75 mmol, the preparation of which can be found in the section detailing the preparation of Example K1) in DMF was added (2S)-2-[(tert-butoxycarbonyl)amino]propyl toluenesulfonate (0.5 g, 1.50 mmol) and cesium carbonate (0.72 g, 2.25 mmol) and the mixture was stirred with heating at 75° C. for 12 h. The reaction was allowed to cool and 25 mL of a solution of 20% water/ethanol was added. The resulting precipitate was filtered and dried in a vacuum oven to give the product (200 mg, 49%). $^1$H NMR (DMSO-D6) δ 1.15 (3H, d, J=6.1 Hz), 1.40 (9H, s), 3.79 (6H, m), 7.22-7.20 (3H, m), 7.59 (2H, d, J=8.4 Hz), 7.95-7.99 (3H, m) 8.40 (1H, s). LCMS m/z=542 (m+H+).

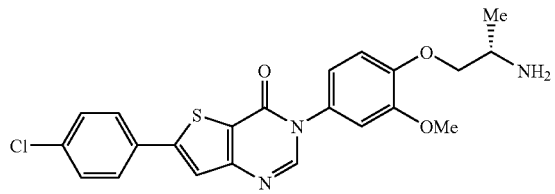

3-(4-{[(2S)-2-aminopropyl]oxy}-3-methoxyphenyl)-6(4-chlorophenyl)thieno[3,2-d]pyrimidin-4(3H)-one To the material from the preceding step (62 mg, 0.11 mmol) was added DCM (4 mL) and trifluoroacetic acid (4 mL) and the mixture was stirred at RT for 20 min. The solvents were removed by rotary evaporation. To the resulting gum was added 1 N NaOH and the solution was extracted with ether 3×. The organic extracts were dried and concentrated to yield the title compound (44 mg, 87%). $^1$H NMR(methanol-D4) δ 1.25 (3H, d, J=6.5 Hz), 3.91 (3H, s), 4.05 (1H, m), 7.05 (1H, m), 7.15 (2H, m), 7.53 (2H, d, J=8.5 Hz), 7.73 (1H, s), 7.84 (2H, d, J=8.5 Hz), 8.370 (1H, s). LCMS m/z=442 (m+H+).

EXAMPLE H30

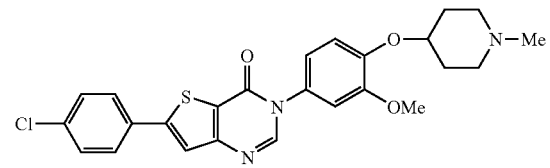

6-(4-chlorophenyl)-3-{3-methoxy-4-[(1-methyl-4-piperidinyl)oxy]phenyl}thieno[3,2d]pyrimidin-4(3H)-one

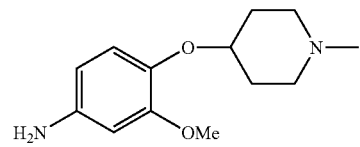

3-methoxy-4-[(1-methyl-4-piperidinyl)oxy]aniline

To a solution of 4-[4-nitro-2-methoxyphenoxy]-1-methylpiperidine (2.17 g, 8.15 mmol, in ethanol (150 mL) was added 10% palladium on cabon (400 mg). The mixture was subjected to 1 atm hydrogen with stirring overnight. Removal of the catalyst by filtration and evaporation of the solvent yielded the product (1.75 g, 91%). $^1$H NMR (CDCl$_3$) δ 1.81-2,04 (4H, m), 2.34 (5H, m), 2.81 (2H, m), 3.56 (2H, br s), 3.80 (3H, s), 4.04 (1H, s), 6.20 (1H, dd, J=2.7 Hz, J'=8.4 Hz), 6.29 (1H,d, J=2.5 Hz), 6.77 (1 H, d, J=8.3 Hz). LCMS m/z=237 (m+H+).

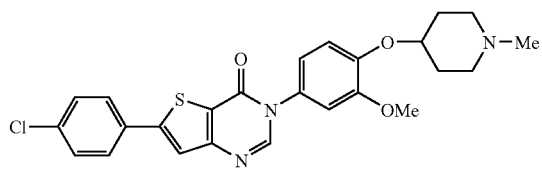

6-(4-chlorophenyl)-3-{3-methoxy-4-[(1-methyl-4-piperidinyl)oxy]phenyl}thieno[3,2-d]pyrimidin-4(3H)-one To a solution of methyl 3-amino-5-(4-chlorophenyl)-2-thiophenecarboxylate (0.27 g, 1.0 mmol, Maybridge, Inc) in ethanol (5 mL) was added dimethylformamide dimethyl acetal (0.33 mL, 2.5 eq, Aldrich). The reaction mixture was refluxed in a 90° C. oil bath for 3 h at which point the solvents were removed by rotary evaporation. Coevaporation with toluene removed the excess dimethylformamide dimethyl acetal. To the resulting residue was added ethanol (5 mL) and the product from the preceding step (3-methoxy-4-[(1-methyl-4-piperidinyl)oxy]aniline, 0.28 g, 1.2 eq). The reaction mixture was heated to 100° C. for 24 hours. Upon cooling to RT a precipitate formed which was filtered and washed with ethanol. The gray powder was dried in a vacuum oven yielding the title compound (0.10 g, 21%). $^1$H NMR (CDCl$_3$) δ 1.68 (2H, m), 1.93 (2H, m), 2.18, 5H, m), 2.64 (2H, m), 3.78 (3H, s), 4.36 (1H, m), 7.04 (1H, dd, J=8.4 Hz, J'=2.3 Hz), 7.20 (2H, m), 7.58 (2H, d, J=8.6 Hz), 7.98 (3H, m), 8.41 (1H, s). LCMS m/z=482 (m+H+). Calcd. for C$_{25}$H$_{24}$Cl$_2$N$_3$O$_3$SCl×0.65 H$_2$O: C, 60.82; H, 5.17; N, 8.51. Found: C, 60.82; H, 5.04; N, 8.41.

EXAMPLE I1

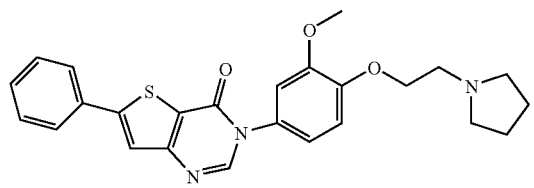

3-[3-Methoxy-4-(2-pyrrolidin-1-ylethoxy)phenyl]-6-phenylthieno[3,2-d]pyrimidin-4(3H)-one

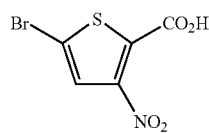

5-Bromo-3-nitrothiophene-2-carboxylic acid

5Bromo-3-nitrothiophene-2-carbaldehyde (0.5953 g, 2.5012 mmol, prepared according to Sone, C; Matsuki, Y Bull Chem Soc Japan, 1963, 36(5), 618-20.) was dissolved in acetone (5 mL) and Jones Reagent (1.5 mL) was added. The reaction was stirred at RT for 1 h. The reaction was diluted with water (30 mL) and extracted with EtOAc (3×30 mL). The combined organics were washed With water (4×100 mL), dried over MgSO$_4$ filtered and concentrated to give 0.4993 g (1.9892 mmol, 80%) of the product as a light yellow solid.

1H NMR (CDCl$_3$) δ 7.58 (s, 1H). LRMS M−H 250.

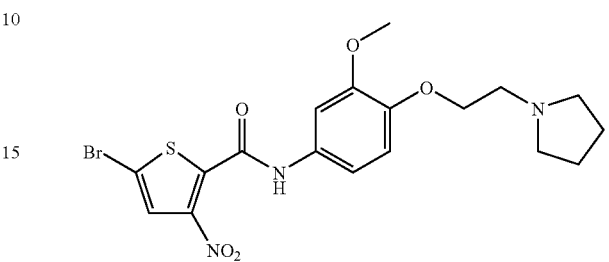

5-Bromo-N-[3-methoxy-4-(pyrrolidin-1ylethoxy)phenyl]-3-nitrothiophene-carboxamide 5-Bromo-3-nitrothiophene-2-carboxylic acid (0.4993 g, 1.9892 mmol) and 3-methoxy-4-(2-pyrrolidin-1-eylethoxy)aniline (0.4695 g, 1.9892 mmol) were dissolved in CH$_2$Cl$_2$ (10 mL). HOBT (0.2960 g, 2.1881 mmol) and Hunig's base (0.866 mL, 4.9730 mmol) were added. The reaction was stirred at RT for 10 min and then EDC (0.4576 g, 2.3870 mmol) was added. The reaction was stirred at RT for 72 h. The reaction was washed with water (2×30 mL), dried over MgSO$_4$, filtered and concentrated. The crude material was purified on a chromatatron (95:5 CH$_2$Cl$_2$:MeOH, with 0.1% NEt$_3$) to give 0.2926 g (0.6239 mmol, 31%) of the product as a dark red gum. 1H NMR (CDCl$_3$) δ 10.58 (s, 1H), 7.70 (s, 1H), 7.42 (s, 1H), 7.06 (dd, 1H J=2.4 Hz, 8.6 Hz), 6.88 (d, 1H, J=8.6 Hz), 4.16 (t, 2H, J=6.2 Hz), 3.90 (s, 3H), 3.00 (t, 2H, J=6.2 Hz), 2.8-2.6 (bs, 4H), 1.9-1.7 (bs, 4H).

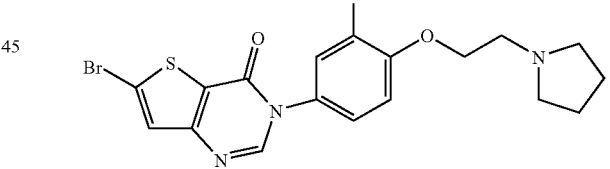

6-Bromo-3-[3-methoxy-4-(2-pyrrolidin-1-ylethoxy)phenyl]thieno[3,2-d]pyrimidin-4(3H)-one 5-Bromo-N-[3-methoxy-4-(pyrrolidin-1ylethoxy)phenyl]-3-nitrothiophene-carboxamide (0.2926 g, 0.6239 mmol) was dissolved in ethanol (10 mL). Tin chloride monohydrate (0.7038 g, 3.1195 mmol) was added and the reaction was heated to reflux. Stirred for 30 min, cooled to RT and concentrated. Ethyl acetate (20 mL) and a saturated solution of Rochelle's salts (20 mL) were added and the mixture was stirred for 2 h. Organics were removed and dried over MgSO$_4$, filtered and concentrated. The residue was taken up in formic acid (5 mL), stirred at reflux for 1 h, and then concentrated to give 0.1182 g (0.2633 mmol, 42%) of the product. 1H NMR (CDCl$_3$) δ 8.03 (s, 1H), 7.38 (s, 1H), 7.01 d, 1H J=8.4 Hz), 6.92-6.88 (m, 2H)), 4.41 (t, 2H, J=5.0 Hz), 3.85 (s, 3H), 3.44 (t, 2H, J=5.0 Hz), 3.28-3.2 (bs, 4H), 2.01-1.9 (bs, 4H).

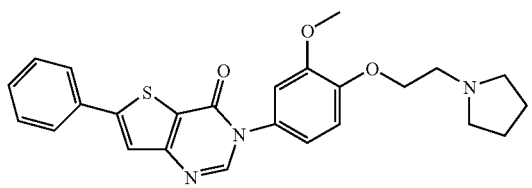

3-[3-Methoxy-4-(2-pyrrolidin-1-ylethoxy)phenyl]-6-phenylthieno[3,2-d]pyrimidin-4(3H)-one 6-Bromo-3-[3-methoxy-4-(2-pyrrolidin-1-ylethoxy)phenyl]thieno[3,2-d]pyrimidin4(3H)-one (0.0386 g, 0.086 mmol) and phenyl boronic acid (0.011 g, 0.091 mmol) were dissolved in a THF (3 mL) and EtOH (1 mL) mixture. Nitrogen was bubbled through the reaction for 5 min. Pd(dppf)$_2$Cl$_2$ and 1M Na$_2$CO$_3$ (1 mL) were added. The reaction was heated to 75° C. and stirred for 30 min. The reaction was portioned between water (20 mL) and EtOAc (20 mL). The organics were removed, dried over MgSO$_4$, filtered and concentrated. The crude product was purified by chromatatron (98:2 CH$_2$Cl$_2$:MeOH) to give 0.005 g (0.011 mmol, 13%) of the product as a light brown solid. $^1$H NMR (CDCl$_3$) δ 8.13 (s, 1H), 7.73 (d, 2H, J=7.1 Hz), 7.56 (s, 1H), 7.5-7.4 (m, 3H), 7.02 (d, 1H J=8.2 Hz), 6.96-6.92 (m, 2H)), 4.26 (t, 2H, J=6.0 Hz), 3.88 (s, 3H), 3.06 (t, 2H, J=6.1 Hz), 2.8-2.6 (bs, 4H), 1.9-1.7 (bs, 4H).

Examples I2-I4 were Prepared According to the Procedures Described in Example I1.

EXAMPLE I2

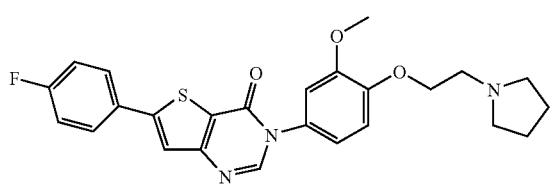

6-(4-Fluorophenyl)-3-[3-methoxy-4-(2-pyrrolidin-1-ylethoxy)phenyl]thieno[3,2-d]pyrimidin-4(3H)-one $^1$H NMR (D6-DMSO) δ 8.37 (s, 1H), 7.93 (t, 2H, J=4.5 Hz), 7.90 (s, 1H), 7.34 (t, 2H, J=8.6 Hz), 7.19 (s, 1H), 7.12 (d, 1H J=8.6 Hz), 7.03 (d, 1H, J=8.4 Hz), 4.26 (bs, 2H), 3.88 (s, 3H), 3.06 (bs, 2H ), 2.8-2.7 (bs, 4H), 1.9-1.7 (bs, 4H). LCMS M=H 467

EXAMPLE I3

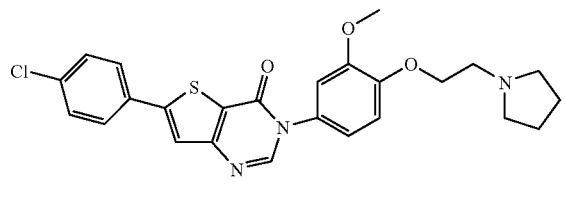

6-(4-Chlorophenyl)-3-[3-methoxy-4(2-pyrrolidin-1-ylethoxy)phenyl]thieno[3,2-d]pyrimidin-4(3H)-one $^1$H NMR (CDCl$_3$) δ 8.13 (s, 1H), 7.65 (d, 2H, J=8.6 Hz), 7.53 (s, 1H), 7.44 (d, 2H, J=8.6 Hz), 7.01 (d, 1H, J=8.8 Hz), 6.94-6.90 (m, 2H), 4.22 (t, 2H, J=6.4 Hz), 3.88 (s, 3H), 3.01 (t, 6.2 Hz), 2.8-2.7 (bs, 4H), 1.9-1.7 (bs, 4H).
LCMS M+H 482

The title compound of Example I3 was also prepared as follows: Methyl 5-(4-chlorophenyl)-3-{[(E)-(dimethylamino)methylidene]amino}-2-thiophenecarboxylate (12.06 g, 0.03735 mol, the preparation of which is found in Example J13) was stirred in absolute ethanol (60 mL) and 3-methoxy-4-(2-pyrrolidin-1-ylethoxy)aniline (8.82 g, 0.03735 mol) was added. The mixture was heated at reflux temperature for 72 h and then cooled to 4° C. and kept at this temperature for 16 h. The resultant precipitate was collected on a fritted glass funnel and the precipitate was then dried in a vacuum oven overnight at 50° C. to provide 9.57 g of a gray solid. This solid was dissolved in dichloromethane (80 mL) and to the resultant mixture was added maleic acid (2.88 g, 24.8 mmol) in methanol (9 mL). The mixture was stirred for 5 min at room temperature and then diethyl ether (7 mL) was added. The mixture was stirred for 10 min at room temperature. The resultant precipitate was collected on fritted glass, washed with ether, and dried at 50° C. overnight in a vacuum oven to produce 8.18 g of the title compound as its maleate salt, mp 214-215° C. $^1$H NMR (400 MHz, CDCl$_3$) δ 8.14 (s, 1H), 7.65 (d, J=8.6 Hz, 2H), 7.53 (s, 1H), 7.44 (d, J=8.6 Hz, 2H), 6.92-7.04 (m, 3H), 6.27 (s, 2H), 4.45 (t, J=4.6 Hz, 2H), 3.89-4.00 (m, 2H), 3.87 (s, 3H), 3.59 (t, J=4.6 Hz, 2H), 3.00-3.14 (m, 2H), 2.10-2.23 (m, 4H).

EXAMPLE I4

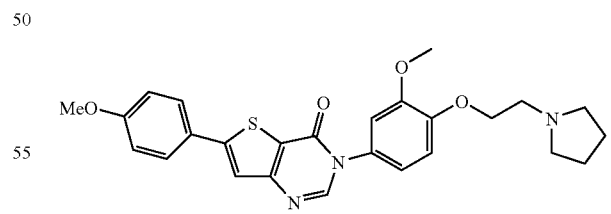

6-(4-Methoxyphenyl)-3-[3-methoxy-4-(2-pyrrolidin-1-ylethoxy)phenyl]thieno[3,2-d]pyrimidin-4(3H)-one $^1$H NMR (CDCl$_3$) δ 8.11 (s, 1H), 7.66 (d, 2H, J=8.8 Hz), 7.44 (s, 1H), 7.01-6.90 (m, 5H), 4.21 (t, 2H, J=6.2 Hz), 3.88 (s, 3H), 3.86 (s, 3H), 2.98 (t, 6.2 Hz), 2.8-2.7 (bs, 4H), 1.9-1.7 (bs, 4H). LCMS M+H 478

EXAMPLE I5

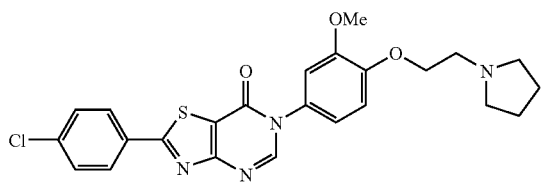

2-(4-Chlorophenyl)-6-[3-methoxy-4-(2-pyrrolidin-1ylethoxy)phenyl][1,3]thiazolo[4,5-d]pyrimidin-7(6H)-one

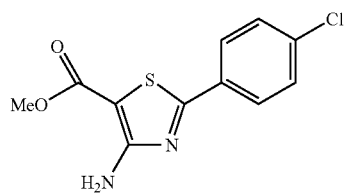

Methyl 4-amino-2-(4-chlorophenyl)-1,3-thiazole-5-carboxylate

Methyl 4-chlorobenzenecarbodithioate (0.690, 3.4158 mmol) and cyanamide (0.1436 g, 3.1458 mmol) were taken up in dry methanol (10 mL). Potassium methoxide (0.2396 g, 3.4158 mmol) was added. The reaction was stirred at RT for 3 h. The reaction mixture was concentrated to dryness to give a red solid. The residue was taken up in DMF (10 mL) and methyl iodide (0.727 g, 5.123 mmol) were added. The reaction was stirred for 2 hours, then diluted with EtOAc (50 mL). The organics were washed with water (3×100 mL), dried over MgSO$_4$, filtered and concentrated. The residue was taken up in dry methanol (10 mL) and thioglycolate methyl ester (0.739 g, 9.96 mmol) was added, followed by triethylamine (1.3 mL). The reaction was stirred overnight at RT. The precipitate was collected to give 0.16 g (0.5970 mmol, 17%) of product. $^1$H NMR (CDCl$_3$) δ 7.85 (d, 2H, J=8.4 Hz), 7.40 (d, 2H, J=8.6 Hz), 5.89 (bs, 2H), 3.85 (s, 3H).

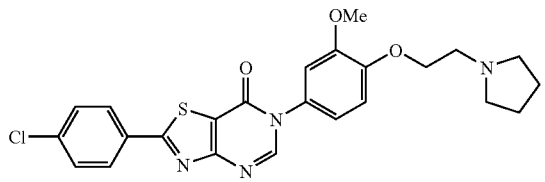

2-(4-Chlorophenyl)-6-[3-methoxy-4-(2-pyrrolidin-1ylethoxy)phenyl][1,3]thiazolo[4,5-d]pyrimidin-7(6H)-one Methyl 4-amino-2-(4-chlorophenyl)-1,3-thiazole-5-carboxylate(0.4589 g, 1.7123 mmol) was dissolved in dimethylformaide dimethyl acetal (5 mL) and heated to 100° C. The reaction was stirred for 3 h and then concentrated to dryness. 3-Methoxy-4-(2-pyrrolidin-1-ylethoxy)aniline (0.404 g, 1.7123 mmol) in anhydrous ethanol (2 mL) was added to the residue. The reaction was heated to 100° C. and stirred for 18 h. The precipitate was collected and purified by chromatatron (3:1 Hex:EtOAc to 9:1 CH$_2$Cl$_2$:MeOH) to give 0.0978 g (0.2029 mmol, 12%) of the product as a cream colored solid. The title compound was dissolved in CH$_2$Cl$_2$ (4 mL) and methanol (0.5 mL). Maleic acid (0.025 g, 0.2130 mmol) was added and the reaction stirred at RT for 4 h. The reaction was concentrated and fresh CH$_2$Cl$_2$ (3 mL) was added. The solids were then collected to give 0.066 g of the maleate salt.

$^1$H NMR (CDCl$_3$) (free base) δ 8.28 (s, 1H), 8.08 (d, 2H, J=8.5 Hz), 7.49 (d, 2H, J=8.6 Hz), 7.03, (d, 1H, J=9.2 Hz), 6.93 (bs, 2H), 4.27 (bs, 2H), 3.88 (s, 3H), 3.05 (bs, 2H), 2.74 (bs, 4H), 1.86 (bs, 4H). $^1$H NMR (D$_6$-DMSO) (maelate salt) δ 9.67 (bs, 1H), 8.55 (s, 1H), 8.16 (d, 2H, J=8.5 Hz), 7.66 (d, 2H, J=8.4 Hz), 7.28, (s, 1H), 7.20 (d, 1H, J=8.6 Hz) 7.10 (d, 2H, J=8.4 Hz), 6.00 (s, 2H), 4.33 (bs, 2H), 3.78 (s, 3H), 3.60 (bs, 2H), 3.20 (bs, 4H), 2.0-1.90 (bs, 4H). LRMS M+H 469

EXAMPLE I6

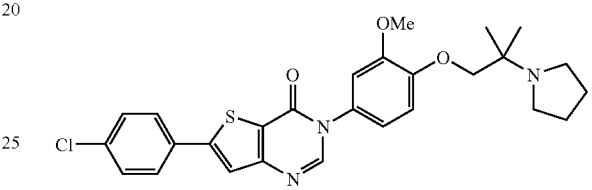

6-(4-Chlorophenyl)-3-[3-methoxy-4-(2-methyl-2-pyrrolidin-1-ylpropoxy)phenyl]thieno[3,2-d]pyrimidin-4(3H)-one

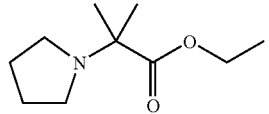

Ethyl 2-methyl-2-pyrrolidin-1-ylpropanoate

Ethyl 2-bromo-2-methylpropanoate (0.6800 g, 3.4861 mmol) was taken up in pyrrolidine (4 mL) and heated to 70° C. The reaction was stirred for 18 h and then concentrated. The residue was taken up in EtOAc (100 mL) and washed with water (1×100 mL), dried over MgSO$_4$, filtered and concentrated to afford 0.4754 g (2.5697 mmol, 74%) of the product. 1H NMR (CDCl$_3$) δ 4.16 (q, 2H, J=7.1 Hz), 2.76 (bs, 4H), 1.76 (bs, 4H), 1.36 (s, 6H), 1.27 (t, 2H, J=7.1 Hz).

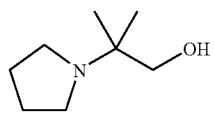

2-Methyl-2-pyrrolidin-1-ylpropan-1-ol

Ethyl 2-methyl-2-pyrrolidin-1-ylpropanoate (0.6162 g, 3.3308 mmol) was taken up in dry THF (5 mL). A 1M solution of LAH in THF (3.7 mL, 3.6639 mmol) was added drop wise. The reaction was warmed to 50° C. and stirred for 18 h. Cooleed to 0° C. in an ice bath and methanol (5 mL) was added slowly. The reaction was diluted with water (50 mL) and extracted with Et$_2$O (2×50 mL). The organics were concentrated by blowing a slow stream of N$_2$ over the flask to give 0.3578 g (2.0682 mmol, 62%) of the product as a light brown oil. $^1$H NMR (CDCl$_3$) δ 3.22 (s, 2H), 2.61 (bs, 4H), 1.79 (bs, 4H), 1.01 (s, 6H).

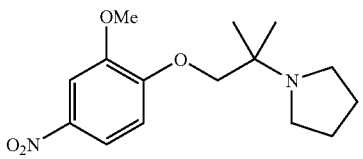

1-[2-(2-Methoxy-4-nitrophenoxy)-1,1-dimethylethyl]pyrrolidine

2-Methyl-2-pyrrolidin-1-ylpropan-1-ol (0.3776 g, 2.0682 mmol) was taken up in anhydrous DMF (5 mL). Sodium hydride (0.083 g of a 60% dispersion, 2.0682 mmol) was added. The reaction was stirred at RT until gas evolution was complete. 1-Chloro-2-methoxy-4-nitrobenzene (0.3578 g, 2.0682 mmol) was added. The reaction was heated to 80° C. and stirred for 72 h. Cooled to RT and diluted with EtOAc, (50 mL) and washed with water (3×50 mL). Organics were dried over MgSO$_4$, filtered and concentrated. Crude product was purified by chromatatron (100% CH$_2$Cl$_2$ to 95:5 CH$_2$Cl$_2$:MeOH) to give 0.075 g (0.2551 mmol, 12%) of the product. $^1$H NMR (CDCl$_3$) δ 7.81 (d, 1H, J=8.8 Hz), 7.73 (s, 1H), 7.15 (d, 1H, J=8.8 Hz), 3.88 (s, 3H), 2.76 (s, 2H), 2.68 (bs, 4H), 1.75 (bs, 4H), 1.38 (s, 6H).

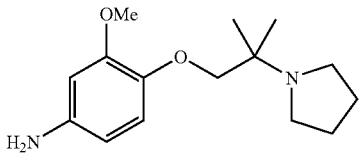

3-Methoxy-4-(2-methyl-2-pyrrolidin-1-ylpropoxy)aniline

1-[2-(2-Methoxy-4-nitrophenoxy)-1,1-dimethylethyl]pyrrolidine (0.075 g, 0.2551 mmol) was dissolved in EtOAc (10 mL). 10% Pd/C (0.007 g) was added and the reaction hydrogenated under 1 atm of H$_2$. The reaction was stirred for 18 h, filtered through celite and the celite washed with EtOAc (3×30 mL). The combined organics were concentrated to afford 0.063 g (0.2386 mmol, 93%) of the product. $^1$H NMR (CDCl$_3$) δ 6.80 (d, 1H, J=8.4 Hz), 6.22 (s, 1H), 6.18 (d, 1H, J=8.3 Hz), 3.78 (s, 3H), 3.50 (bs, 2H), 2.68 (bs, 6H), 1.78 (bs, 4H), 1.22 (s, 6H).

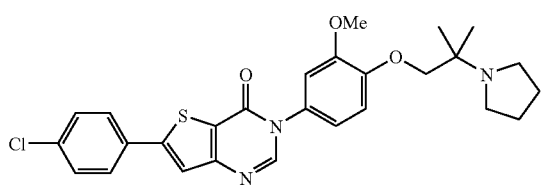

6-(4-Chlorophenyl)-3-[3-methoxy-4-(2-methyl-2-pyrrolidin-1-ylpropoxy)phenyl]thieno[3,2-d]pyrimidin-4(3H)-one Methyl 3-amino-5-(4-chlorophenyl)thiophene-2-carboxylate (0.639 g, 0.2390 mmol) was taken up in DMF-DMA (3 mL) and heated to 110° C. The reaction was stirred for 3 h and then concentrated. 3-Methoxy-4-(2-methyl-2-pyrrolidin-1-ylpropoxy)aniline (0.0631 g, 0.2390 mmol) in absolute ethanol (3 mL) was added to the residue and the mixture was then concentrated. Fresh absolute ethanol (1 mL) was added and the reaction heated to reflux. The reaction was stirred for 18 h and then cooled to RT and the precipitate was collected to give 0.010 g (0.020 mmol, 8%) of the product as a white solid. $^1$H NMR (CDCl$_3$) δ 8.15 (s, 1H), 7.65 (d, 2H, J=8.3 Hz), 7.53 (s, 1H), 7.44 (d, 2H, J=8.5 Hz), 7.18 (d, 1H, J=8.3 Hz), 6.96 (s, 1H), 6.88 (d, 1H, J=8.3 Hz), 3.83 (s, 3H), 2.77 (s, 2H), 2.72 (bs, 4H), 1.78 (bs, 4H), 1.36 (s, 6H).

LRMS M+H 511

EXAMPLE I7

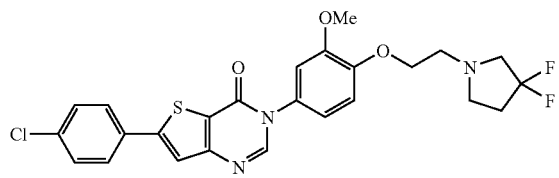

6-(4-Chlorophenyl)-3-{4-[2-(3,3-difluoropyrrolidin-1-yl)ethoxy]-3-methoxyphenyl}thieno[3,2-d]pyrimidin-4(3H)-one

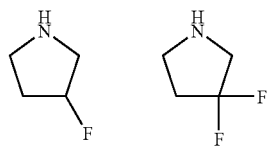

3-fluoropyrrolidine and 3,3-difluoropyrrolidine 3-fluoropyrrolidine and 3,3-difluoropyrrolidine were prepared following procedures described in the literature.

Giardina, G.: Dondio, G.; Grugni, M., *Synlett*, 1995, (1), 55-57

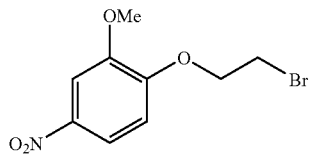

1-(2-Bromoethoxy)-2-methoxy-4-nitrobenzene

4-Nitroguaiacol (1.0171 g, 6.0134 mmol) was dissolved in anhydrous DMF (20 mL). Cesium carbonate (3.9207 g, 12.0268 mmol) and 1,2-dibromoethane (2.07 mL, 24.0534 mmol) were added. The reaction was heated to 80° C. and stirred for 18 h. The mix was then cooled to RT and diluted with EtOAc (100 mL), washed with water (3×100 mL), and the organics dried over MgSO$_4$, filtered and concentrated. The residue was filtered through a 3" plug of basic alumina (100% CH$_2$Cl$_2$) to give 0.7075 g (2.5634 mmol, 42%) of the product as a white solid. $^1$H NMR (CDCl$_3$) δ 7.90 (d, 1H, J=8.8 Hz), 7.78 (s, 1H), 6.92 (d, 1H, J=8.8 Hz), 4.42 (t, 2H, J=6.4 Hz), 3.96 (s, 3H), 3.70 (t, 2H, J=6.5 Hz).

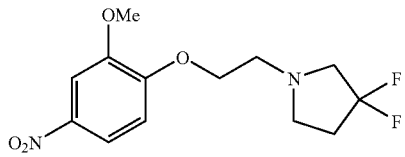

3,3-Difluoro-1-[2-(2-methoxy-4-nitrophenoxy)ethyl] pyrrolidine 3,3-Difluoropyrrolidine (0.4589 g, 2.0859 mmol) and 1-(2-bromoethoxy)-2-methoxy-4-nitrobenzene (0.5757 g, 2.0859 mmol) were combined in DMF (5 mL). Triethylamine (0.6332 g, 6.2577 mmol) was added. The reaction was heated to 80° C. and stirred for 18 h. The reaction was cooled to RT and diluted with EtOAc (50 mL). The organics were washed with water (3×100 mL), dried over MgSO$_4$, filtered and concentrated. The residue was purified by chromatatron (1:1 Hex:EtOAc) to give 0.173 g (0.5728 mmol, 27%) of the product as a light yellow oil. $^1$H NMR (CDCl$_3$) δ 7.90 (d, 1H, 9 Hz), 7.75 (s, 1H), 6.89 (d, 1H, J=9 Hz), 4.21 (t, 2H, J=5.6 Hz), 3.94 (s, 3H), 3.07 (t, 2H, J=13.3 Hz), 2.99 (t, 2H, J=5.7 Hz), 2.89 (t, 2H, J=7.1 Hz), 2.28 (m, 2H).

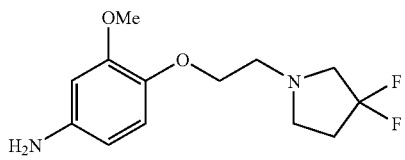

4-[2-(3,3-Difluoropyrrolidin-1-yl)ethoxy]-3-methoxyaniline 3,3-Difluoro-1-[2-(2-methoxy-4-nitrophenoxy)ethyl]pyrrolidine (0.173 g, 0.5728 mmol) was dissolved in EtOAc (5 mL). 10% Pd/C (0.017 g) was added. The reaction was stirred under 1 atm of H$_2$. for 18 h. The mix was then filtered through celite and the celite washed with EtOAc (3×10 mL). The organics were concentrated to give 0.1389 g (0.5107 mmol, 89%) of the product as a red oil. $^1$H NMR (CDCl$_3$) δ 6.73 (d, 1H, J=8.4 Hz), 6.29 (s, 1H), 6.19 (d, 1H, J=8.4 Hz), 4.02 (t, 2H, J=5.8 Hz), 3.80 (s, 3H0, 3.04 (t, 2H, J=13.4 Hz), 2.87 (m, 4H), 2.27 (m, 2H).

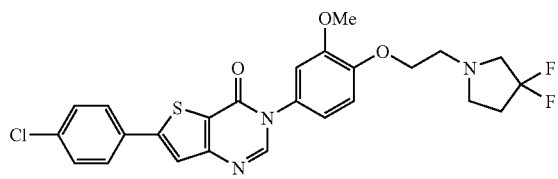

6-(4-Chlorophenyl)-3-{4-[2-(3,3-difluoropyrrolidin-1-yl)ethoxy]-3-methoxyphenyl}thieno[3,2-d]pyrimidin-4(3H)-one Methyl 3-amino-5-(4-chlorophenyl)thiophene-2-carboxylate (0.1367 g, 0.5107 mmol) was taken up in dimethylformamdide dimethyl acetal (3 mL) and heated to 110° C. The reaction was stirred for 3 h and then concentrated. 4-[2-(3,3-Difluoropyrrolidin-1-yl)ethoxy]-3-methoxyaniline (0.1389 g, 0.5107 mmol) in absolute ethanol (3 mL) was added to the residue and concentrated. Fresh absolute ethanol (1 mL) was added and the reaction heated to reflux. The reaction was stirred for 18 h and then cooled to RT and the precipitate was collected to give 0.058 g (0.1120 mmol, 22%) of the product as a white solid. $^1$H NMR (D$_6$-DMSO) δ 8.38 (s, 1H), 7.96 (s, 1H, 7.91 (d, 2H, J=8.4 Hz), 7.56 (d, 2H, J=8.4 Hz), 7.18 (s, 1H), 7.11 (d, 1H, J=8.5 Hz), 7.04 (d, 1H, J=8.6 Hz), 4.12 (t, 2H, J=5.5 Hz), 3.77 (s, 3H), 3.00 (t, 2H, J=13.6 Hz), 2.85 (t, 2H, J=5.5 Hz), 2.81 (t, 2H, J=7.0 Hz), 2.22 (m, 2H). LRMS M+H

EXAMPLE I8

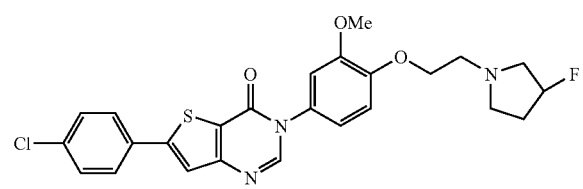

6-(4-chlorophenyl)-3-{4-[2-(3-fluoropyrrolidin-1-yl) ethoxy]-3-methoxyphenyl}thieno[3,2-d]pyrimidin-4 (3H)-one

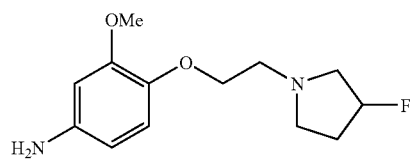

3-Fluoro-1-[2-(2-methoxy-4-nitrophenoxy)ethyl] pyrrolidine 1-(2-Bromoethoxy)-2-methoxy-4-nitrobenzene (0.2346 g, 0.8499 mmol) and 3-fluoropyrrolidine (0.3187 g, 2.5496 mmol) were combined in DMF (5 mL). Triethylamine (0.43 g, 4.2495 mmol) was added. The reaction was heated to 80° C. and stirred for 18 h. The reaction was cooled to RT and diluted with EtOAc (50 mL). The organics were washed with water (3×100 mL), dried over MgSO$_4$, filtered and concentrated. The residue was purified by chromatatron (98:2 CH$_2$Cl$_2$:MeOH). The product was subjected to hydrogenation using 10% Pd/C under 1 atm of H$_2$. The reaction was stirred for 18 h and was then filtered through celite and the celite washed with EtOAc (2×10 mL). The organics were concentrated to give 0.0442 g (0.1740 mmol, 20%) of the product. $^1$H NMR (CDCl$_3$) δ 6.75 (d, 1H, J=8.4 Hz), 6.28 (s, 1H), 6.19 (d, 1H, J=8.3 Hz), 5.26-5.13 (m, 1H), 4.10 (t, 2H, J=5.7 Hz), 3.80 (s, 3H), 3.10-2.78 (m, 6H), 2.27-2.05 (m, 2H).

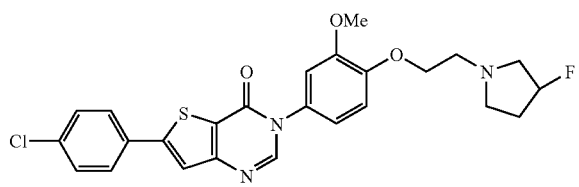

6-(4-chlorophenyl)-3-{4-[2-(3-fluoropyrrolidin-1-yl)ethoxy]-3-methoxyphenyl}thieno[3,2-d]pyrimidin-4(3H)-one 3-Fluoro-1-[2-(2-methoxy-4-nitrophenoxy)ethyl]pyrrolidine (0.0442 g, 0.1740 mmol) and methyl 5-(4-chlorophenyl)-3-{[(1E)-(dimethylamino)methylidene]amino}thiophene-2-carboxylate (0.056 g, 0.1740 mmol) were charged to a flask. Phenol (1 g) was added and the reaction heated to 200° C. The reaction was stirred for 45 min until all starting material was gone. The mix was then cooled to RT, diluted with $CH_2Cl_2$ (30 mL) and washed with 1N NaOH (2×30 mL), water (1×30 mL), brine (1×30 mL), dried over $MgSO_4$, filtered, and concentrated. The residue was purified on a chromatatron (98:2 $CH_2Cl_2$:MeOH) to give 0.010 g (0.020 mmol, 11%) of the product as a tan solid. $^1$H NMR ($CDCl_3$) δ 8.13 (s, 1H), 7.65 (d, 2H, J=8.3 Hz), 7.52 (s, 1H), 7.43 (d, 2H, J=8.4 Hz), 7.00 (d, 1H, J=8.4 Hz), 6.93 (m, 2H), 5.29-5.13 (m,1H), 4.23 (t, 2H, J=5.7 Hz), 3.88 (s, 3H), 3.12-2.93 (m, 5H), 2.68 (bs, 1H), 2.25-2.06 (m, 2H). LRMS M+H 500

EXAMPLE J1

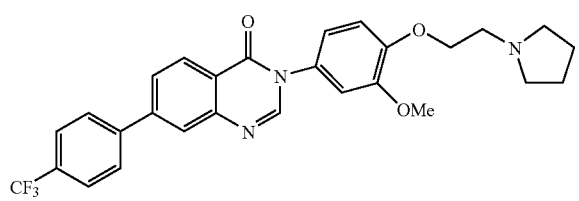

3-{3-methoxy-4-[2-(1-pyrrolidinyl)ethoxy]phenyl}-7-[4-(trifluoromethyl)phenyl]-4(3H)-quinazolinone

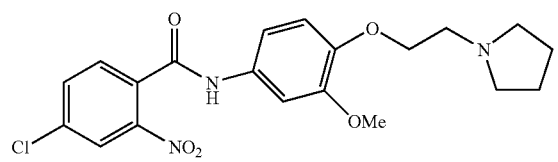

4-chloro-N{3-methoxy-4-[2(1-pyrrolidinyl)ethoxy]phenyl}-2-nitrobenzamide

To a solution of 3-methoxy-4-[2-(1-pyrrolidinyl)ethoxy]aniline (43 mmol, 10.0 g) in DCM was added triethylamine (52 mmol, 5.2 g) and 4-chloro-2-nitrobenzoyl chloride (9.5 g, 43 mmol). The solution was stirred overnight. The reaction mixture was extracted with 2N HCl. The resulting acidic aqueous solution was made basic by adding 2N NaOH. The combined basic aqueous solution was extracted with DCM. The organic phase was washed with brine, dried and concentrated giving the title compound (11.5 g, 69%). $^1$H NMR (DMSO-D6): δ 1.66 (4H, m), 2.49 (4H, m), 2.75 (2H, t, J=6.0 Hz), 3.72 (3H, s), 4.00 (2H, t, J=6.0 Hz), 6.94 (1H, d, J=8.6 Hz), 7.14 (1H, d, J=8.6 Hz), 7.79 (1H, d, J=8.1 Hz), 7.94 (1H, d, J=8.1 Hz), 8.23 (1H, s), 10.55 (1H, s). LCMS m/z=420 (m+H$^+$).

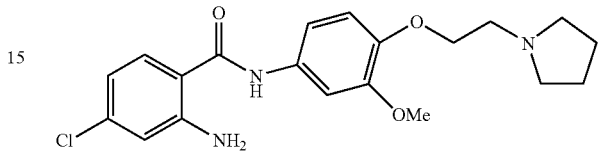

2-amino-4-chloro-N-{3-methoxy-4-[2-(1-pyrrolidinyl)ethoxy]phenyl}benzamide

To a solution of 4-chloro-N-{3-methoxy-4-[2-(1-pyrrolidinyl)ethoxy]phenyl}-2-nitrobenzamide (11.9 mmol, 5.0 g) in ethanol was added tin(II) chloride dihydrate (35.8 mmol, 8.1 g). The resulting mixture was heated to reflux for 4 h and then concentrated by rotary evaporation. The residue was dissolved in ethyl acetate and was washed with potassium sodium tartrate tetrahydrate solution repeatedly. The crude product was first extracted with 2N HCl, then made basic by adding NaOH with ice cooling. The combined basic aqueous solution was extracted with DCM. The organic extraction was washed with brine, dried and concentrated giving the product (4.5 g, 97%). $^1$H NMR (DMSO-D6): δ 1.67 (4H, m), 2.48 (4H, m), 2.81 (2H, t, J=5.8 Hz), 3.75 (3H, s), 4.10 (2H, t, J=5.8 Hz), 7.02 (1H, d, J=6.2 Hz), 7.10 (1H, d, J=8.6 Hz), 7.16 (1H, s), 7.62 (1H, d, J=8.6 Hz), 7.80 (1H, s), 8.17 (1H, d, 8.6 Hz), 8.35 (1H, s). LCMS m/z=390 (m+H$^+$).

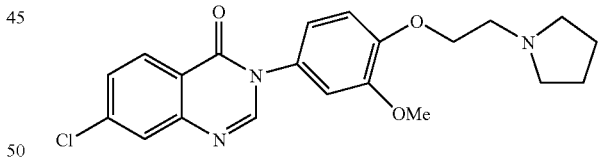

7-chloro-3-{3-methoxy-4-[2-(1-pyrrolidinyl)ethoxy]phenyl}-4(3H)-quinazolinone

2-Amino-4-chloro-N-{3-methoxy-4-[2-(1-pyrrolidinyl)ethoxy]phenyl}benzamide (11.6 mmol, 4.5 g) was dissolved in 90 mL 88% formic acid and was heated to reflux for 3 h. The solvents were removed by rotary evaporation and the residue was purified by silica gel column chromatography affording the lo product (4.2 g, 91%). $^1$H NMR (DMSO-D6): δ 1.82 (4H, m), 2.65 (4H, m), 2.88 (2H, t, J=6.2 Hz), 3.88 (3H, s), 4.20 (2H, t, J=6.4 Hz), 6.89-6.91 (2H, overlapping), 7.01 (1H, d, J=10.1 Hz), 7.49 (1H, d, J=8.6 Hz), 7.76 (1H, s), 8.12 (1H, s), 8.29 (1H, d, 8.7 Hz). LCMS m/z=400 (m+H$^+$).

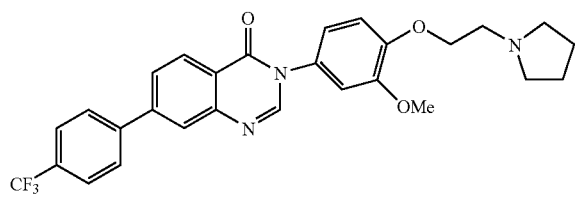

3-{3-methoxy-4-[2-(1-pyrrolidinyl)ethoxy]phenyl}-7-[4-(trifluoromethyl)phenyl]-4(3H)-quinazolinone The aryl chloride from the preceding step (150 mg, 0.38 mmol), trifluoromethylphenyl boronic acid (130 mg, 1.5 eq), bis-t-butylbiphenylphosphine (24 mg, 20 mol %), palladium acetate (9 mg, 10 mol %) and potassium fluoride (65 mg, 3 eq) were added to a dry round bottom flask. To this was added anhydrous THF (2.0 mL). The reaction mixture was heated at 70° C. for 3 h. The reaction mixture was filtered. The filtrate was diluted with ethyl acetate and was washed with 1N NaOH and with water. The aqueous washes were back extracted twice with ethyl acetate. The organic portion was dried and concentrated. The residue was purified by silica gel column chromatography eluting with 10% acetone in DCM with 1% triethylamine to give the title compound (0.36 g, 61%). $^1$H NMR (CDCl$_3$): δ 1.98 (4H, m), 3.02 (4H, m), 3.24 (2H, m), 3.89 (3H, s), 4.38 (2H, t, J=5.5 Hz), 6.93-6.97 (2H, overlapping), 7.05 (1H, d, J=9.5 Hz), 7.76-7.83 (5H, overlapping), 7.99 (1H, s), 8.16 (1H, s), 8.44 (1H, d, 8.3 Hz). LCMS m/z=510(m+H$^+$).

Examples J2-J12 were Prepared According to the Procedures Described in Example J1.

EXAMPLE J2

7-(4-fluoro-3-methylphenyl)-3-{3-methoxy-4-[2-(1-pyrrolidinyl)ethoxy]phenyl}-4(3H)-quinazolinone $^1$H NMR (CDCl$_3$): δ 2.05 (4H, m), 2.37 (3H, s), 3.30 (4H, m), 3.46 (2H, m), 3.88 (3H, s), 4.42 (2H, m), 6.93-6.97 (2H, overlapping), 7.04 (1H, d, J=8.4 Hz), 7.13 (1H, d, J=8.9 Hz), 7.48-7.54 (2H, overlapping), 7.73 (1H, d, J=8.3 Hz), 7.91 (1H, s), 8.14 (1H, s), 8.38 (1H, d, 8.5), 8.45 (1H, bs). LCMS m/z=474 (m+H$^+$).

EXAMPLE J3

3-{3-methoxy-4-[2-(1-pyrrolidinyl)ethoxy]phenyl}-7-(4-methylphenyl)-4(3H)-quinazolinone $^1$H NMR (CDCl$_3$): δ 1.99 (4H, m), 2.17 (3H, s), 3.14 (4H, m), 3.34 (2H, t, J=5.3 Hz), 3.88 (3H, s), 4.38 (2H, t, J=5.3 Hz), 6.93-6.97 (2H, overlapping), 7.03 (1H, d, J=8.4 Hz), 7.32 (1H, d, J=8.1 Hz), 7.63 (1H, d, J=8.1 Hz), 7.78 (1H, d, J=8.2 Hz), 7.96 (1H, s), 8.13 (1H, s), 8.39 (1H, d, 8.3 Hz), 8.48 (1H, s). LCMS m/z=455 (m+H$^+$).

EXAMPLE J4

7-(4-methoxyphenyl)-3-{3-methoxy-4-[2-(1-pyrrolidinyl)ethoxy]phenyl}-4(3H)-quinazolinone $^1$H NMR (CDCl$_3$): δ 1.85 (4H, m), 2.72 (4H, m), 3.04 (2H, t, J=6.1 Hz), 3.88 (3H, s), 3.89 (3H, s), 4.25 (2H, t, J=6.2 Hz), 6.94-7.05 (5H, overlapping), 7.67 (2H, d, J=8.4 Hz), 7.75 (1H, d, J=8.3 Hz), 7.93 (1H, s), 8.13 (1H, s), 8.37 (1H, d, 8.2 Hz). LCMS m/z=472 (m+H$^+$).

EXAMPLE J5

7-(4-chlorophenyl)-3-{3-methoxy-4-[2-(1-pyrrolidinyl)ethoxy]phenyl}-4(3H)-quinazolinone $^1$H NMR (CDCl$_3$): δ 1.97 (4H, m), 3.03 (4H, m), 3.27 (2H, t, J=5.6 Hz), 3.88 (3H, s), 4.34 (2H, t, J=5.6 Hz), 6.95-6.96 (2H, m, overlapping), 7.04 (1H, d, J=8.4 Hz), 7.48 (2H, d, J=8.4 Hz), 7.65 (2H, d, J=8.2 Hz), 7.74 (1H, d, J=8.2 Hz), 7.94 (1H, s), 8.14 (1H, s), 8.41 (1H, d, J=8.3 Hz), 8.50 (1H, s). LCMS m/z=476 (m+H$^+$).

EXAMPLE J6

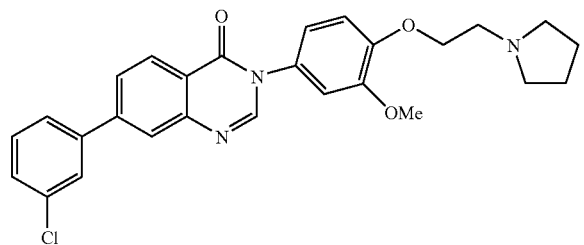

7-(3-chlorophenyl)-3-{3-methoxy-4-[2-(1-pyrrolidinyl)ethoxy]phenyl}-4(3H)-quinazolinone $^1$H NMR (CD$_3$OD): (maleic acid salt) δ 2.14 (4H, bs), 3.47-3.54 (4H, bs), 3.70 (2H, t, J=5.3 Hz), 3.92 (3H, s), 4.40 (2H, t, J=4.8 Hz), 6.24 (2H, s, maleic acid), 7.08 (1H, d, J=84 Hz), 7.22-7.25 (2H, m, overlapping), 7.45-7.54 (2H, m, overlapping), 7.71 (1H, d, J=7.6 Hz), 7.78 (1H, s), 7.88 (1H, d, J=8.3 Hz), 8.28 (1H, s), 8.33-8.37 (2H, m, overlapping). LCMS m/z=476 (m+H$^+$).

EXAMPLE J7

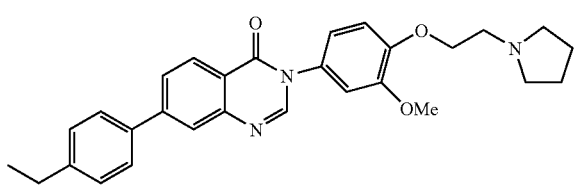

7-(4-ethylphenyl)-3-{3-methoxy-4-[2-(1-pyrrolidinyl)ethoxy]phenyl}-4(3H)-quinazolinone $^1$H NMR (CDCl$_3$) δ 1.29 (3H, t, J=7.6 Hz), 1.82 (4H, m), 2.62 (4H, m), 2.73 (2H, q, J=7.6 Hz), 2.99 (2H, t, J=3.6 Hz), 3.87 (3H, s), 4.22 (2H, t, J=3.6 Hz), 6.91-7.02 (3H, m, overlapping), 7.34 (2H, d, J=8.1 Hz), 7.65 (2H, d, J=8.1 Hz), 7.78 (1H, d, J=8.3), 7.96 (1H, s), 8.12 (1H, d, J=8.8 Hz), 8.38 (1H, d, J=8.3 Hz). LCMS m/z=470 (m+H$^+$).

EXAMPLE J8

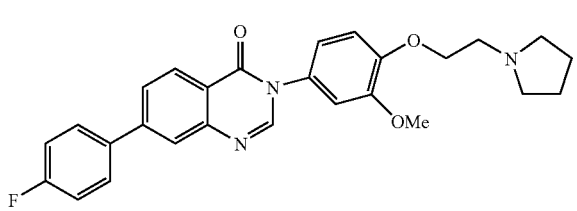

7-(4-fluorophenyl)-3-{3-methoxy-4-[2-(1-pyrrolidinyl)ethoxy]phenyl}-4(3H)-quinazolinone $^1$H NMR (CDCl$_3$) δ 1.83 (4H, bs), 2.66 (4H, bs), 2.99 (2H, d, J=6.4 Hz), 3.89 (3H, s), 4.22 (2H, t, J=6.4 Hz), 6.92-6.95 (2H, m, overlapping), 7.20 (1H, t, J=8.1 Hz), 7.67-7.71 (3H, m, overlapping), 7.92 (1H, s), 8.15 (1H, s), 8.40 (1H, d, J=8.3 Hz). LCMS m/z=460 (m+H$^+$).

EXAMPLE J9

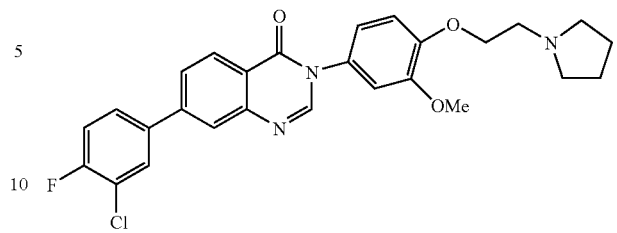

7-(3-chloro-4-fluorophenyl)-3-{3-methoxy-4-[2-(1-pyrrolidinyl)ethoxy]phenyl}-4(3H)-quinazolinone $^1$H NMR (CDCl$_3$): (maleic acid salt) δ 2.05 (4H, bs), 3.18 (4H, bs), 3.34 (2H, bs), 3.89 (3H, s), 4.46 (2H, bs), 5.58 (2H, s, maleic acid), 6.93-6.97 (2H, m, overlapping), 7.07 (1H, d, J=8.5 Hz), 7.28 (1H, overlapping with CDCl$_3$), 7.58 (1H, m), 7.69 (1H, d, J=8.4 Hz), 7.75 (1H, d, J=6.8 Hz), 7.9 (1H, s), 8.14 (1H, s), 8.41 (1H, d, J=8.3 Hz). LCMS m/z=494 (m+H$^+$).

EXAMPLE J10

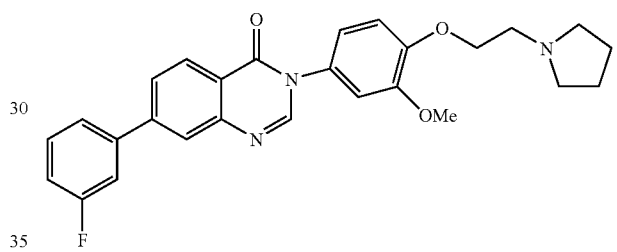

7-(3-fluorophenyl)-3-{3-methoxy-4-[2-(1-pyrrolidinyl)ethoxy]phenyl}-4(3H)-quinazolinone $^1$H NMR (CDCl$_3$) δ 1.94 (4H, bs), 2.94 (4H, bs), 3.19 (2H, bs), 3.88 (3H, s), 4.35 (2H, t, J=5.7 Hz), 6.92-7.05 (2H, m, overlapping), 7.11 (1H, m), 7.39-7.50 (4H, m, overlapping), 7.74 (1H, d, J=8.3 Hz), 7.95 (1H, s), 8.14 (1H, s), 8.41 (1H, d, J=8.5 Hz). LCMS m/z=460 (m+H$^+$).

EXAMPLE J11

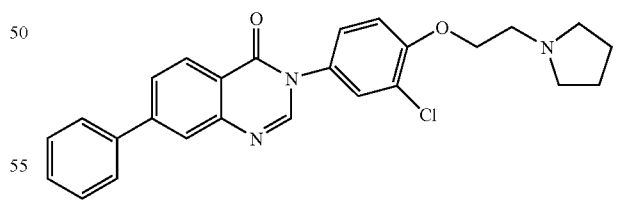

3-{3-chloro-4-[2-(1-pyrrolidinyl)ethoxy]phenyl}-7-phenyl-4(3H)-quinazolinone $^1$H NMR (CDCl$_3$) δ 1.84 (4H, bs), 2.73 (4H, bs), 3.04 (2H, t, J=5.8 Hz), 4.27 (2H, t, J=5.8 Hz), 7.08 (1H, d, J=8.8 Hz), 7.29 (1H, d, J=8.6), 7.44-7.53 (3H, m, overlapping), 7.72 (2H, d, J=7.2 Hz), 7.80 (1H, d, J=8.3 Hz), 7.98 (1H, s), 8.10 (1H, s), 8.40 (1H, d, J=8.2 Hz). LCMS m/z=446 (m+H$^+$).

EXAMPLE J12

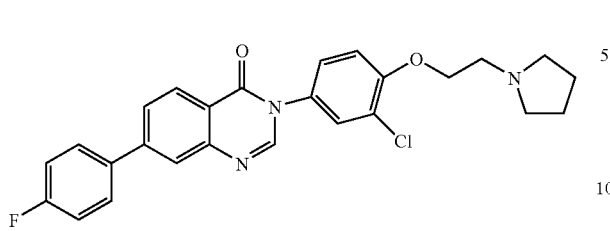

3-{3-chloro-4-[24(1-pyrrolidinyl)ethoxy]phenyl}-7-(4-fluorophenyl)-4(3H)-quinazolinone $^1$H NMR (CDCl$_3$) δ 1.84 (4H, bs), 2.75 (4H, bs), 3.05 (3H, t, J=5.5 Hz), 4.28 (3H, t, J=5.5 Hz), 7.07 (1H, d, J=8.8 Hz), 7.17-7.29 (3H, m, overlapping), 7.47 (1H, s), 7.66-7.73 (3H, m, overlapping), 7.91 (1H, s), 8.09 (1H, s), 8.38 (1H, d, J=8.3 Hz). LCMS m/z=464 (m+H$^+$).

EXAMPLE J13

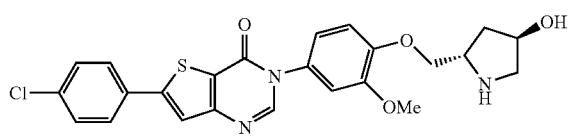

6-(4-chlorophenyl)-3-(4-{[(2S,4R)-4-hydroxypyrrolidinyl]methoxy}-3-methoxyphenyl)thieno[3,2-d]pyrimidin-4(3H)-one

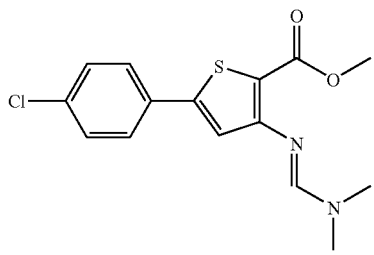

Methyl 5-(4-chlorophenyl)-3-{[(E)-(dimethylamino)methylidene]amino}-2-thiophenecarboxylate A mixture of methyl 3-amino-5-(4-chlorophenyl)-2-thiophenecarboxylate (37.3 mmol, 10.0 g) and N,N-dimethylformamide dimethyl acetal (74.7 mmol, 8.9 g) in ethanol (350 mL) was heated at reflux for 3 hours. The solvent was removed by rotary evaporation. To the residue 15 mL of toluene was added and the solvent was removed by rotary evaporation. This was repeated three times. To the resulting sticky residue, 20 mL hexanes was added followed by the gradual addition of ethyl acetate at 0° C. until it solidified. The resulting solid was collected by filtration giving the product (11.9 g, 98.9%). $^1$H NMR (CDCl$_3$): δ 3.08 (6H, d, J=6.5 Hz), 3.81 (3H, s), 6.98 (1 H. s), 7.35 (2H, d, J=8.6 Hz), 7.53 (2H, d, J=8.5 Hz), 7.69 (1H, s). LCMS m/z=323 (m+H$^+$).

6-(4-chlorophenyl)-3-(4-{[(2S,4R)-4-hydroxypyrrolidinyl]methoxy}-3-methoxyphenyl)thieno[3,2-d]pyrimidin-4(3H)-one Methyl 5-(4-chlorophenyl)-3-{[(E)-(dimethylamino)methylidene]amino}-2-thiophenecarboxylate (857 mg, 2.66 mmol) was mixed with tert-butyl (2S,4R)-2-[(4-amino-2-methoxyphenoxy)methyl]4-hydroxypyrrolidine-1-carboxylate (900 mg) in phenol (1.0 g) at 120° C. for 15 min. Workup and purification of the reaction mixture provided 650 mg of tert-butyl (2S,4R)-2-({4-[6-(4-chlorophenyl)-4-oxothieno[3,2-d]pyrimidin-3(4H)-yl]-2-methoxyphenoxy}methyl)-4-hydroxypyrrolidine-1-carboxylate. A portion of this material (105 mg, 0.179 mmol) was dissolved in a 1:1 mixture of dichloromethane and trifluoroacetic acid. The mixture was stirred at room temperature for 10 min and was then concentrated under reduced pressure. The residue was dissolved in dichloromethane and washed with a saturated solution of NaHCO$_3$, brine, dried (Na$_2$SO$_4$) and concentrated to provide the title compound.

$^1$H NMR (CDCl$_3$): δ 1.80 (1H, m), 2.01 (1H, m), 2.98 (1H, d, J=11.9 Hz), 3.15 (1H, dd, J=11.9, 4.3 Hz), 3.87 (3H, s), 3.88-4.00 (3H, m, overlapping), 4.50 (1H, m), 6.89-6.94 (2H, m, overlapping), 6.99 (1H, d, J=8.4 Hz), 7.44 (2H, d, J=8.4 Hz), 7.51 (1H, s), 7.63 (2H, d, J=8.6 Hz), 8.12 (1H, s). LCMS m/z=484 (m+H$^+$).

EXAMPLE J14

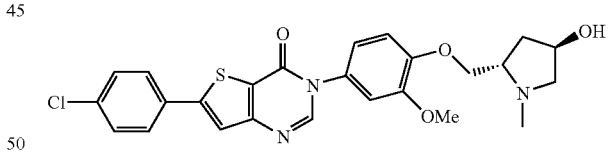

6-(4-chlorophenyl)-3-(4-{[(2S,4R)-4-hydroxy-1-methylpyrrolidinyl]methoxy}-3-methoxyphenyl)thieno[3,2-d]pyrimidin-4(3H)-one The title compound was obtained through treatment of the title compound from Example J13 with the procedures described in Example H18.

$^1$H NMR (CDCl$_3$): δ 2.03-2.10 (1H, m), 2.40-2.43 (1H, m), 2.53 (3H, s), 3.02-3.18 (2H, m), 3.41-3.48 (1H, m), 3.98-4.05 (2H, m, overlapping), 4.49 (1H, m), 6.90-6.98 (3H, m, overlapping), 7.44 (2H, d, J=8.6 Hz), 7.53 (1H, s), 7.65 (2H, d, J-8.6 Hz), 9.73 (1H, s). LCMS m/z=498 (m+H$^+$).

EXAMPLE J15

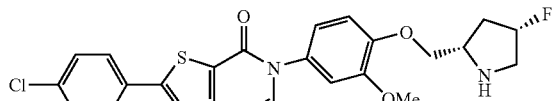

6-(4-chlorophenyl)-3-(4-{[(2S,4S)-4-fluoropyrrolidinyl]methoxy}-3-methoxyphenyl)thieno[3,2-d]pyrimidin-4(3H)-one

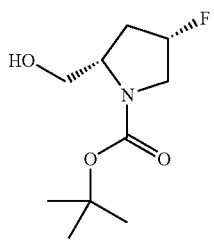

tert-butyl (2S,4S)-4-fluoro-2-(hydroxymethyl)-1-pyrrolidinecarboxylate

To a THF (20 mL) solution of 1-tert-butyl 2-methyl (2S,4S)-4-fluoro-1,2-pyrrolidinedicarboxylate (950 mg, 3.9 mmol) at 0° C., 5.8 mL 2M LiBH$_4$ (11.6 mmol, 3 eq) was added slowly. The resulting mixture was left stirring overnight while allowing the temperature to warm up to room temperature.

The reaction was quenched with 50% acetic acid with ice bath. The mixture was diluted with ethyl acetate. To this was added 50 mL silica gel and the mixture was stirred for 10 minutes. This was filtered and the filtrate was concentrated to give the intermediate (780 mg, 93%). $^1$H NMR (CDCl$_3$) δ 1.48 (9H, s), 1.98-2.29 (2H, m, overlapping), 4.48-8.17 (5H, m, overlapping), 5.15 (1H, d, J=43 Hz).

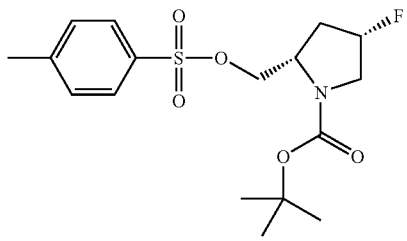

tert-butyl (2S,4S)-4-fluoro-2-({[(4-methylphenyl)sulfonyl]oxy}methyl)-1-pyrrolidinecarboxylate Reaction of the product from the previous step with p-toluene sulfonyl chloride under standard conditions provided the product.

$^1$H NMR (CDCl$_3$): δ 1.42 (9H, s), 2.04 (1H, m), 2.34 (1H, m), 2.45 (3H, s), 3.58 (2H, m, overlapping), 3.85 (1H, m), 4.11-4.31 (2H, m, overlapping), 5.19 (1H, d, J=52.8 Hz), 7.35 (2H, m), 7.79 (2H, d, J=8.4 Hz).

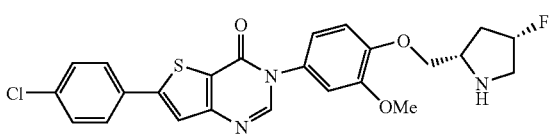

6-(4-chlorophenyl)-3-(4-({[2S,4S)-4-fluoropyrrolidinyl]methoxy}-3-methoxyphenyl)thieno[3,2-d]pyrimidin-4(3H)-one Alkylation of 6-(4-chlorophenyl)-3-(4-hydroxy-3-methoxyphenyl)thieno[3,2-d]pyrimidin-4(3H)-one (the preparation of which may be found in Example K1) (the preparation of which may be found in Example K1) with the product from the previous step was followed by removal of the BOC group with a 1:1 mixture of dichloromethane and trifluoroacetic acid to provide the title compound.

$^1$H NMR (CDCl$_3$): δ 1.98 (1H, m), 2.25 (1H, m), 3.00-3.12 (1H, ddd, J=34.9, 13.0, 4.0), 3.34-3.43 (1H, m), 3.87 (3H, s), 4.09 (2H, m), 5.18-5.34 (1H, d, J=54.4 Hz), 6.88-6.95 (2H, m, overlapping), 7.03 (1 H. d, J=8.5 Hz), 7.44 (2H, d, J=8.5 Hz), 7.51 (1H, s), 7.64 (2H, d, J=8.4 Hz), 8.13 (1H, s). LCMS m/z=486 (m+H$^+$).

EXAMPLE J16

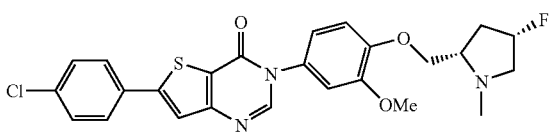

6-(4-chlorophenyl)-3-(4-{[(2S,4S)-4-fluoro-1-methylpyrrolidinyl]methoxy}-3-methoxyphenyl)thieno[3,2-d]pyrimidin-4(3H)-one The title compound was obtained through treatment of the title compound from Example J15 with the procedures described in Example H18.

$^1$H NMR (CD$_3$OD): (maleic acid salt) δ 2.26 (1H, m), 2.88 (1H, m), 3.25 (3H, s), 3.40-3.52 (1H, dd, J=39.6, 13.0 Hz), 3.90 (3H, s), 3.98 (1H, m), 4.08 (1H, m), 4.27 (1H, t, J=9.9 Hz), 4.54 (1H, dd, J=11.0,3.5 Hz), 5.45 (1H, d, J=14.7 Hz), 6.24 (2H, s, maleic acid), 7.07 (1H, d, J=8.6 Hz), 7.18-7.22 (2H, m, overlapping), 7.51 (2H, d, J=8.4 Hz), 7.72 (1H, s), 7.82 (2H, d, J=8.6 Hz), 8.34 (1H, s). LCMS m/z=500 (m+H$^+$).

EXAMPLE J17

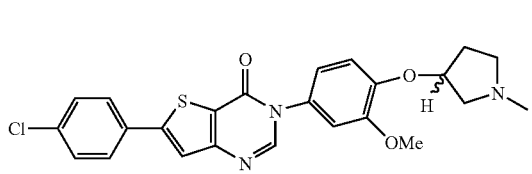

6-(4-chlorophenyl)-3-{3-methoxy-4-[(1-methyl-3-pyrrolidinyl)oxy]phenyl}thieno[3,2-d]pyrimidin-4(3H)-one The title compound was obtained using procedures analogous to those described in Example H30.

$^1$H NMR (CDCl$_3$) δ 2.06 (1H, m), 2.34 (1H, m), 2.40 (3H, s), 2.53 (1H, m), 2.78 (2H, m) 2.93 (1H, m), 3.86 (3H, s), 4.88 (1H, m), 6.89-6.93 (2H, m, overlapping), 7.43 (2H, d, J=8.6 Hz), 7.51 (1H, s), 7.64 (2H, d, J=8.6 Hz), 8.13 (1H, s). LCMS m/z=468 (m+H$^+$).

EXAMPLE J18

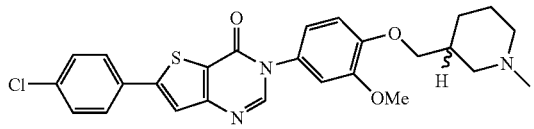

6-(4-chlorophenyl)-3-{3-methoxy-4-[(1-methyl-3-piperidinyl)methoxy]phenyl}thieno[3,2-d]pyrimidin-4(3H)-one A solution containing 6-(4-chlorophenyl)-3-(4-hydroxy-3-methoxyphenyl)thieno[3,2-d]pyrimidin-4(3H)-one (77 mg, 0.20 mmol, the preparation of which may be found in Example K1) and 3-(chloromethyl)-1-methylpiperidine (74 mg) was mixed with Cs$_2$CO$_3$ (261 mg, 0.80 mmol) and the resultant mixture was heated at 85° C. for 3 hours. The mixture was then cooled to room temperature, diluted with dichlormethane, washed with a saturated solution of NaHCO$_3$ and brine, dried (MgSO$_4$), and concentrated under reduced pressure. The resultant residue was purified by column chromatography to provide the title compound.

$^1$H NMR (CDCl$_3$) δ 1.15 (1H, m), 1.69-2.03 (5H, m), 2.23-2.27 (1H, m), 2.31 (3H, s), 2.78 (1H, m), 2.99 (1H, m), 3.87 (3H, s), 3.94 (2H, m), 6.86-6.98 (3H, m, overlapping), 7.43 (2H, d, J=8.3 Hz), 7.52 (1H, s), 7.65 (2H, d, J=8.6 Hz), 8.12 (1H, s). LCMS m/z=496 (m+H$^+$).

EXAMPLE J19

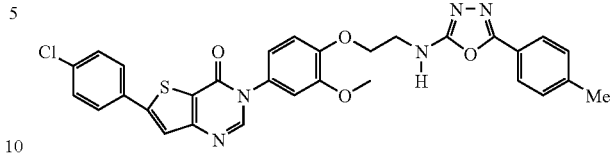

6-(4-chlorophenyl)-3-[3-methoxy-4-(2-{[5-(4-methylphenyl)-1,3,4-oxadiazol-2-yl]amino}ethoxy)phenyl]thieno[3,2-d]pyrimidin-4(3H)-one

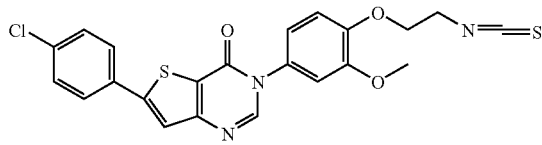

6-(4-chlorophenyl)-3-[4-(2-isothiocyanatoethoxy)-3-methoxyphenyl]thieno[3,2-d]pyrimidin-4(3H)-one The primary amine product from Example H16 (0.82 mmol, 350 mg) was reacted with dipyridylithionocarbonate (0.82 mmol, 190 mg) in DCM (10 mL) overnight. The solvent was removed by rotary evaporation. The residue was purified by flash chromatography eluting from straight DCM to 10% acetone in DCM giving the title compound (385 mg, 100%). $^1$H NMR (CDCl$_3$) δ 3.91 (3H, s), 3.95 (2H, t, J=5.5 Hz), 4.28 (2H, t, J=5.5 Hz), 6.95 (1H, dd, J=8.4 Hz, 2,4 Hz), 7.00 (1H, d, J=2.4 Hz), 7.06 (1H, d, J=8.4 Hz), 7.45 (2H, dd, J=6.6 Hz, 1.9 Hz), 7.54 (1H, s), 7.66 (2H, dd, J=6.6 Hz, 1.8 Hz), 8.14 (1H, s).

LCMS m/z=470 (m+H$^+$).

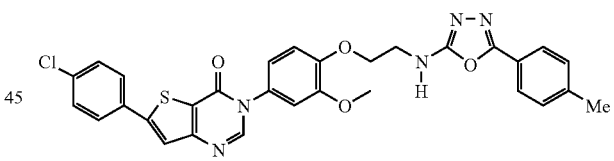

6-(4-chlorophenyl)-3-[3-methoxy-4-(2-{[5-(4-methylphenyl)-1,3,4-oxadiazol-2-yl]amino}ethoxy)phenyl]thieno[3,2-d]pyrimidin-4(3H)-one The product from the preceding step (0.18 mmol, 85 mg) was reacted with 4-methylbenzohydrazide (0.20 mmol, 30 mg) in 2 mL DMSO with 4 eq. EDC overnight. The reaction mixture was diluted with DCM and washed with water, saturated sodium bicarbonate solution. After drying over sodium sulfate, the solvent was removed by rotary evaporation. The final product was purified by recrystalization giving the title compound (86 mg, 82%). $^1$H NMR (CDCl$_3$) δ 2.39 (3H, s), 3.88(5H, m, overlapping), 4.31 (2H, t, J=4.9 Hz), 6.93 (1H, dd, J=8.4 Hz, 2.4 Hz), 6.98 (1H, d, J=2.4 Hz), 7.05 (1H, d, J=8.4 Hz), 7.25 (2H, m, overlapping with CDCL3), 7.44(2H, d, J=8.6 Hz), 7.53 (1H, s), 7.65 (2H, d, J=8.7 Hz), 7.79 (2H, d, J=8.3 Hz), 8.12 (1H, s). LCMS m/z=586 (m+H$^+$).

EXAMPLE K1

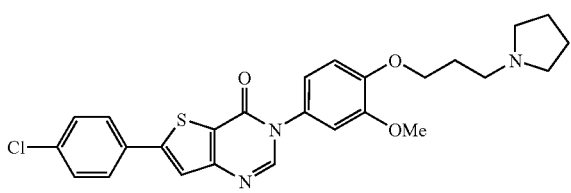

6-(4-Chlorophenyl)-3-[3-methoxy-4-(3-pyrrolidin-1-ylpropoxy)phenyl]thieno[3,2-d]pyrimidin-4(3H)-one

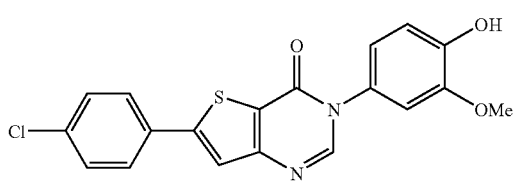

6-(4-Chlorophenyl)-3-(4-hydroxy-3-methoxyphenyl)thieno[3,2-d]pyrimidin-4(3H)-one A dioxane (20 mL) solution of 2-methoxy-4-nitrophenol (6.76 g, 0.04 mol) with Pd(OH)$_2$/C (0.1 g) was agitated on a Parr shaker apparatus under 45 PSI hydrogen pressure for 2 hours. The reaction mixture was removed to a nitrogen atmosphere, filtered through celite and added as a dioxane solution (30 mL) to methyl 5-(4-chlorophenyl)-3-{[(1Z)-(dimethylamino) methylidene]amino}thiophene-2-carboxylate (5.4 g, 0.02 mol, the preparation of which is found in Example J 13). This solution was concentrated and refluxed overnight as a 40 mL absolute ethanol solution. When the reaction mixture was at room temperature the precipitated solid was filtered, and triturated with ethanol and then diethyl ether to give a white solid (2.7 g, 0.007 mol, 35%). LCMS m/z 385 (MH+). $^1$H NMR (300 MHz, DMSO-d$_6$) δ 9.40 (s, 1H), 8.40 (s, 1H), 7.97 (s, 1H), 7.95 (d, 2H), 7.60 (d, 2H), 7.18 (s, 1H), 6.90 (m, 2H), 3.80 (s, 3H) ppm.

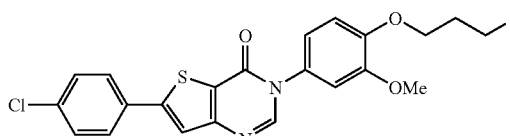

3-[4-(3-Bromopropoxy)-3-methoxyphenyl]-6-(4-chlorophenyl)thien[3,2-d]pyrimidin-4(3H)-one A mixture of cesium carbonate (1.7 g, 0.0052 mol), 6-(4-chlorophenyl)3-(4-hydroxy-3-methoxyphenyl)thieno[3,2-d]pyrimidin4(3H)-one (0.5 g, 0.0013 mol), 1,3-dibromopropane (2.01 g, 0.010 mol) and DMF (30 mL) was warmed with intermittent mixing to 75° C. overnight. The mix was then cooled to RT and diluted with a mixture of ether and water. The precipitated solid was filtered and then triturated with ether to give a white powder (0.60 g, 92%). LCMS m/z 506 (MH+). $^1$H NMR (300 MHz, DMSO-d$_6$) δ 8.40 (s, 1H), 8.00 (s, 1H), 7.95 (d, 2H), 7.60 (d, 2H), 7.22 (s, 1H), 7.18 (d, 1H), 7.05 (d, 1H), 4.18 (t, 2H), 3.80 (s, 3H), 3.70 (t, 2H), 2.30 (m, 2H) ppm.

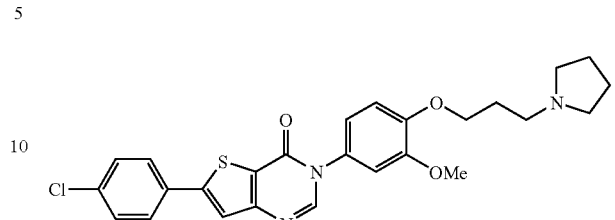

6-(4-Chlorophenyl)-3-[3-methoxy-4-(3-pyrrolidin-1-ylpropoxy)phenyl]thieno[3,2-d]pyrimidin-4(3H)-one.

A DMF (0.25 mL) solution of the intermediate from the preceding step (0.050 g, 0.0001 mol) and pyrrolidine was agitated at RT overnight, diluted with ether/water, filtered to give a yellow solid (0.026 g, 53%). LCMS m/z 496 (MH+).

Examples K2-K12 were prepared according to the procedures detailed for Example K1.

EXAMPLE K2

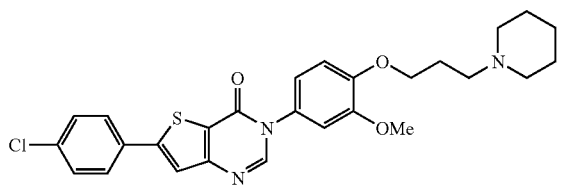

6-(4-Chlorophenyl)-3-[3-methoxy-4-(3-piperidin-1-ylpropoxy)phenyl]thieno[3,2-d]pyrimidin-4(3H)-one.

LCMS m/z 510 (MH+).

EXAMPLE K3

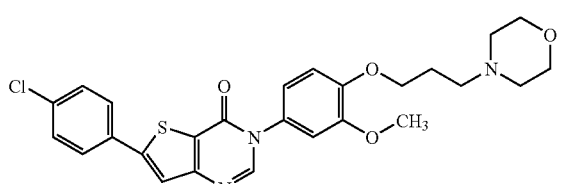

6-(4-Chlorophenyl)-3-[3-methoxy-4-(3-morpholin-4-ylpropoxy)phenyl]thieno[3,2-d]pyrimidin-4(3H)-one LCMS m/z 512 (MH+). $^1$H NMR (300 MHz, DMSO-d$_6$) δ 8.40 (s, 1H), 8.00 (s, 1H), 7.95 (d, 2H), 7.60 (d, 2H), 7.22 (s, 1H), 7.10 (d, 1H), 7.02 (d, 1H), 4.05 (t, 2H), 3.80 (s, 3H), 3.60 (m, 4H), 2.45 (t, 2H), 2.40 (m, 4H), 1.90 (m, 2H) ppm.

EXAMPLE K4

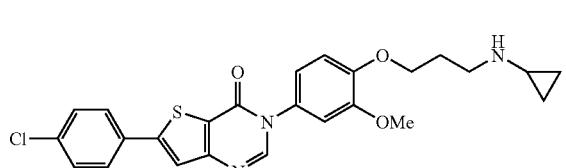

6-(4-Chlorophenyl)-3-{4-[3-(cyclopropylamino)propoxy]-3-methoxy-phenyl}thieno[3,2-d]pyrimidin-4(3H)-one LCMS m/z 482 (MH+). $^1$H NMR (300 MHz, DMSO-$d_6$) δ 8.40 (s, 1H), 8.00 (s, 1H), 7.95 (d, 2H), 7.60 (d, 2H), 7.20 (s, 1H), 7.10 (d, 1H), 7.02 (d, 1H), 4.10 (t, 2H), 3.80 (s, 3H), 2.78 (t, 2H), 2.25 (br, 1H), 2.09 (t, 1H), 1.90 (m, 2H), 0.40 (m, 2H), 0.20 (m, 2H) ppm.

EXAMPLE K5

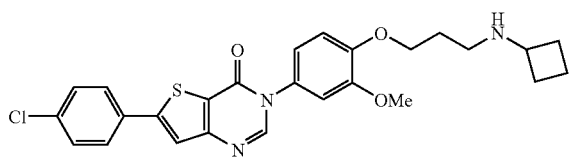

6-(4-Chlorophenyl)-3-{4-[3-(cyclobutylamino)propoxy]-3-methoxy-phenyl}thieno[3,2-d]pyrimidin-4(3H)-one LCMS m/z 496 (MH+). $^1$H NMR (300 MHz, DMSO-$d_6$) δ 8.40 (s, 1H), 8.00 (s, 1H), 7.95 (d, 2H), 7.60 (d, 2H), 7.20 (s, 1H), 7.10 (d, 1H), 7.02 (d, 1H), 4.10 (t, 2H), 3.80 (s, 3H), 3.30 (m, 1H), 3.20 (t, 1H), 2.60 (t, 2H), 2.10 (m, 2H), 1.83 (m, 2H), 1.61 (m, 4H) ppm.

EXAMPLE K6

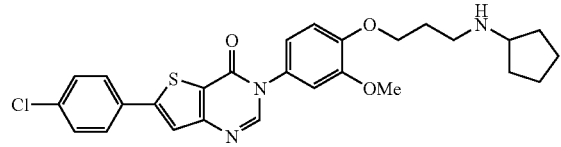

6-(4-Chlorophenyl)-3-{4-[3-(cyclopentylamino)propoxy]-3-methoxy-phenyl}thieno[3,2-d]pyrimidin-4(3H)-one LCMS m/z 510 (MH+). $^1$H NMR (300 MHz, DMSO-$d_6$) δ 8.40 (s, 1H), 8.00 (s, 1H), 7.95 (d, 2H), 7.60 (d, 2H), 7.20 (s, 1H), 7.10 (d, 1H), 7.02 (d, 1H), 4.10 (t, 2H), 3.80 (s, 3H), 3.30 (m, 1H), 3.00 (t, 1H), 2.61 (t, 2H), 1.90 (t, 2H), 1.70 (m, 2H), 1.61 (m, 2H), 1.45 (m, 2H), 1.30 (m, 2H) ppm.

EXAMPLE K7

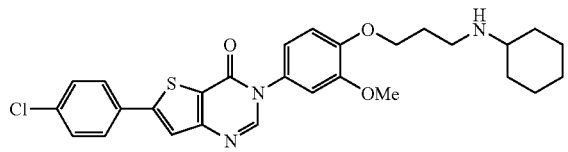

6-(4-Chlorophenyl)-3-{4-[3-(cyclohexylamino)propoxy]-3-methoxy-phenyl}thieno[3,2-d]pyrimidin-4(3H)-one LCMS m/z 524 (MH+). $^1$H NMR (300 MHz, DMSO-$d_6$) δ 8.40 (s, 1H), 8.00 (s, 1H), 7.95 (d, 2H), 7.60 (d, 2H), 7.20 (s, 1H), 7.10 (d, 1H), 7.02 (d, 1H), 4.10 (t, 2H), 3.80 (s, 3H), 3.30 (m, 1H), 3.00 (t, 1H), 2.61 (t, 2H), 1.90 (t, 2H), 1.70 (m, 2H), 1.61 (m, 2H), 1.45 (m, 2H), 1.30 (m, 2H) ppm.

EXAMPLE K8

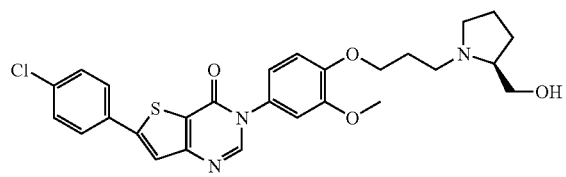

6-(4-Chlorophenyl)-3-(4-{3-[(2S)-2-(hydroxymethyl)pyrrolidin-1-yl]propoxy}-3-methoxyphenyl)thieno[3,2-d]pyrimidin-4(3H)-one LCMS m/z 526 (MH+).

EXAMPLE K9

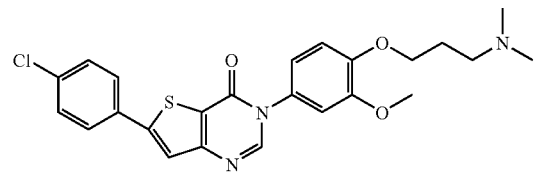

6-(4-Chlorophenyl)-3-{4-[3-(dimethylamino)propoxy]-3-methoxy-phenyl}thieno[3,2-d]pyrimidin-4(3H)-one LCMS m/z 470 (MH+).

EXAMPLE K10

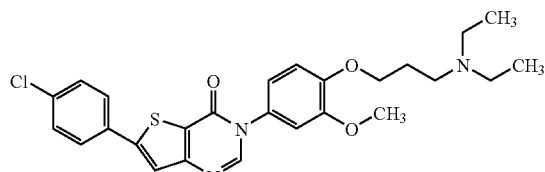

6-(4-Chlorophenyl)-3-{4-[3-(diethylamino)propoxy]-3-methoxyphenyl}thieno[3,2-d]pyrimidin-4(3H)-one LCMS m/z 498 (MH+).

EXAMPLE K11

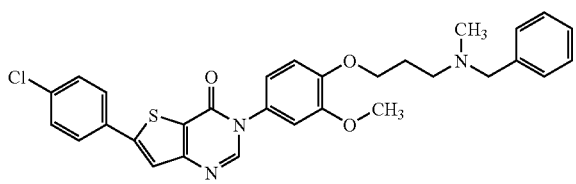

3-(4-{3-[benzyl(methyl)amino]propoxy}-3-methoxyphenyl)-6-(4-chlorophenyl)thieno[3,2-d]pyrimidin-4(3H)-one LCMS m/z 546 (MH+).

EXAMPLE K12

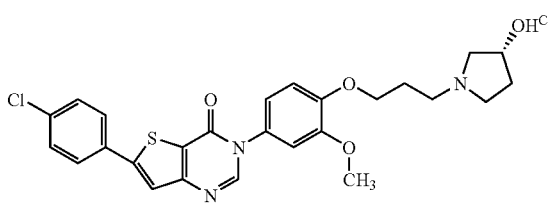

6-(4-Chlorophenyl)-3-(4-{3-[(3R)-3-hydroxypyrrolidin-1-yl]propoxy}-3-methoxyphenyl)thieno[3,2-d]pyrimidin-4(3H)-one LCMS m/z 512 (MH+). $^1$H NMR (300 MHz, DMSO-$d_6$) δ 8.40 (s, 1H), 8.00 (s, 1H), 7.95 (d, 2H), 7.60 (d, 2H), 7.20 (s, 1H), 7.10 (d, 1H), 7.02 (d, 1H), 4.63 (d, 1H), 4.18 (m, 1H), 4.09 (t, 2H), 3.80 (s, 3H), 3.75 (m, 2H), 3.30-3.50 (m, 2H), 2.78 (t, 2H), 2.22-2.70 (m, 2H), 1.90 (m, 2H) ppm.

EXAMPLE K13

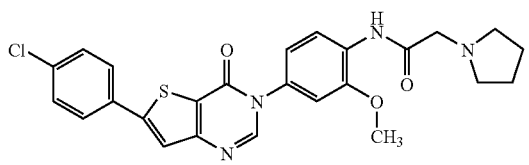

N-{4-[6-(4-chlorophenyl)-4-oxothieno[3,2-d]pyrimidin-3(4H)-yl]-2-methoxyphenyl}2-pyrrolidin-1-ylacetamide

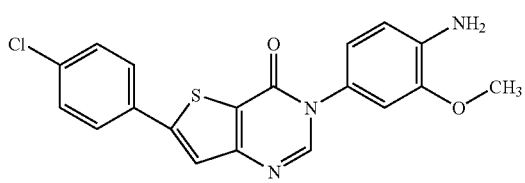

3-(4-Amino-3-methoxyphenyl)-6-(4-chlorophenyl)thieno[3,2-d]pyrimidin-4(3H)-one

The product was prepared according to the manner of 6-(4-chlorophenyl)-3-(4-hydroxy-3-methoxyphenyl)thieno[3,2-d]pyrimidin4(3H)-one (the preparation of which may be found in Example K1), using 2-methoxybenzene-1,4-diamine to give the product as a yellow powder (0.19 g, 50%). LCMS m/z 384 (MH+). $^1$H NMR (300 MHz, DMSO-$d_6$) δ 8.40 (s, 1H), 8.00 (s, 1H), 7.95 (d, 2H), 7.60 (d, 2H), 7.00 (s, 1H), 6.80 (d, 1H), 6.75 (d, 1H), 5.05 (s, 2H), 3.80 (s, 3H), ppm.

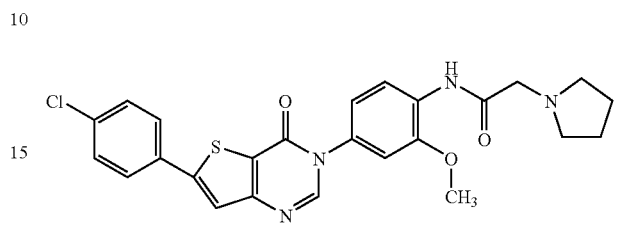

N-{4-[6-(4-chlorophenyl)-4-oxothieno[3,2-d]pyrimidin-3(4H)-yl]-2-methoxyphenyl}-2-pyrrolidin-1-ylacetamide The material from the preceding step was reacted with chloroacetyl chloride followed by reaction with pyrrolidine to provide the title compound as a golden powder (0.028 g, 44%). LCMS m/z 495 (MH+). $^1$H NMR (300 MHz, DMSO-$d_6$) δ 9.65 (s, 1H), 8.42 (s, 1H), 8.35 (d, 1H), 8.00 (s, 1H), 7.95 (d, 2H), 7.60 (d, 2H), 7.35 (s, 1H), 7.10 (d, 1H), 3.90 (s, 3H), 3.42 (m, 2H), 2.60 (m, 4H), 1.80 (m, 4H) ppm.

EXAMPLE K14

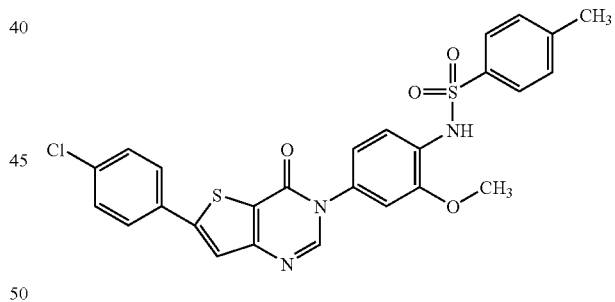

N-{4-[6-(4-chlorophenyl)-4-oxothieno[3,2-d]pyrimidin-3(4H)-yl]-2-methoxyphenyl}-4-methylbenzenesulfonamide A pyridine (1 mL) solution of 3-(4-Amino-3-methoxyphenyl)-6-(4-chloro-phenyl)thieno[3,2-d]pyrimidin-4(3H)-one (0.050 g, 0.0013 mol, the preparation of which is found in Example K13) and p-toluenesulfonyl chloride and was agitated overnight at RT, then diluted with water and filtered to give a white powder (0.056 g 81%). LCMS m/z 538 (MH+). $^1$H NMR (300 MHz, DMSO-$d_6$) δ 9.72 (s, 1H), 8.40 (s, 1H), 8.00 (s, 1H), 7.95 (d, 2H), 7.70 (d, 2H), 7.60 (d, 2H), 7.38 (d, 2H), 7.35 (d, 1H), 7.20 (s, 1H), 7.05 (d, 1H), 3.62 (s, 3H), 2.41 (s, 3H) ppm.

EXAMPLE K15

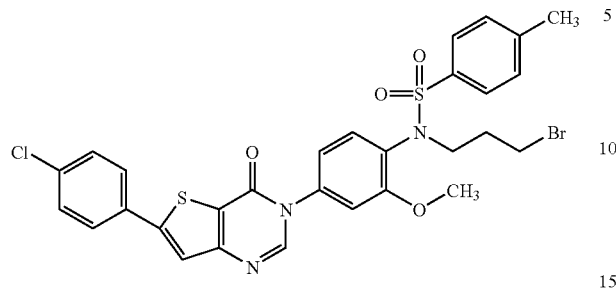

N-(3-bromopropyl)-N-{4-[6-(4-chlorophenyl)-4-oxothieno[3,2-d]pyrimidin-3(4H)-yl]-2-methoxyphenyl}-4-methylbenzenesulfonamide A mixture of cesium carbonate (2.9 g, 0.0088 mol), N-{4-[6-(4-chloro-phenyl)4-oxothieno[3,2-d]pyrimidin-3(4H)-yl]-2-methoxyphenyl}-4-methylbenzenesulfonamide (1.2 g, 0.0022 mol, the title compound from Example K14), 1,3dibromopropane (3.6 g, 0.018 mol) and DMF (30 mL) was warmed with intermittent mixing to 75° C. overnight and then when at RT, diluted with a mixture of ether and water. The precipitated solid was filtered and then triturated with ether to give a white powder (1.2 g, 83%). LCMS m/z 659 (MH+). $^1$H NMR (300 MHz, DMSO-$d_6$) δ 8.50 (s, 1H), 8.00 (s, 1H), 7.95 (d, 2H), 7.60 (d, 4H), 7.40 (d, 2H), 7.32 (s, 1H), 7.30 (d, 1H), 7.18 (d, 1H), 3.62 (t, 2H), 3.58 (t, 2H), 3.50 (s, 3H), 2.41 (s, 3H), 1.95 (t, 2H) ppm.

EXAMPLE K16

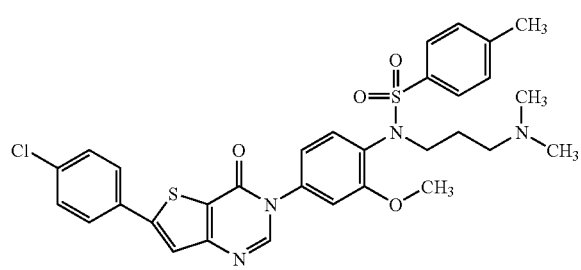

N-{4-[6-(4-Chlorophenyl)-4-oxothieno[3,2-d]pyrimidin-3(4H)-yl]-2-methoxyphenyl}-N-[3-(dimethylamino)propyl]-4-methylbenzene-sulfonamide The title compound was prepared by reaction of N-(3-bromopropyl)-N{4-[6-(4-chlorophenyl)4-oxothieno[3,2-d]pyrimidin-3(4H)-yl]-2-methoxyphenyl}4-methylbenzenesulfonamide (the title compound from Example K15) and dimethylamine. LCMS m/z 623 (MH+).

Examples K17-K19 were prepared through procedures analogous to those found in the preparation of Example K16.

EXAMPLE K17

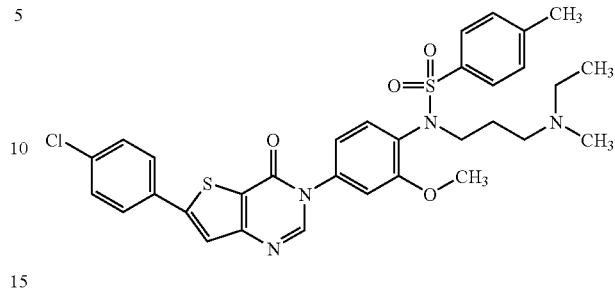

N-{4-[6-(4-chlorophenyl)-4-oxothieno[3,2-d]pyrimidin-3(4H)-yl]-2-methoxyphenyl}-N-[3-(diethylamino)propyl]-4-methylbenzene-sulfonamide LCMS m/z 651 (MH+).

EXAMPLE K18

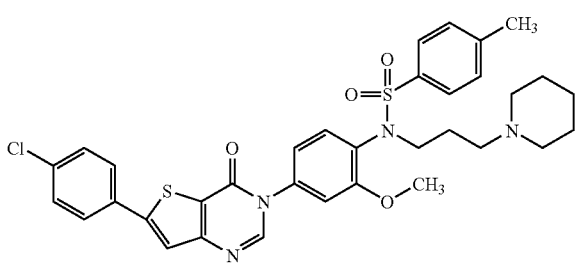

N-{4-[6-(4-chlorophenyl)-4-oxothieno[3,2-d]pyrimidin-3(4H)-yl]-2-methoxyphenyl}-4-methyl-N-(3-piperidin-1-ylpropyl)benzene-sulfonamide LCMS m/z 663 (MH+).

EXAMPLE K19

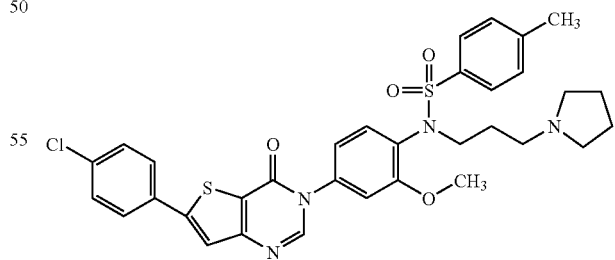

N-{4-[6-(4-chlorophenyl)-4-oxothieno[3,2-d]pyrimidin-3(4H)-yl]-2-methoxyphenyl}4-methyl-N-(3-pyrrolidin-1-ylpropyl)benzene-sulfonamide LCMS m/z 649 (MH+).

EXAMPLE K20

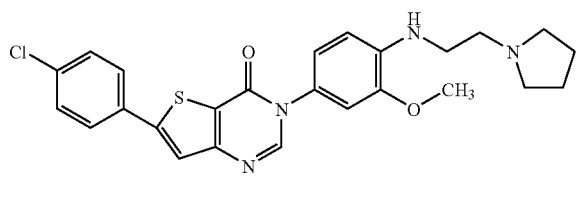

6-(4-chlorophenyl)-3-{3-methoxy-4-[(2-pyrrolidin-1-ylethyl)amino]phenyl}thieno[3,2-d]pyrimidin-4(3H)-one

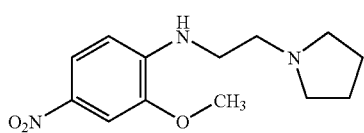

2-methoxy-4-nitro-N-(2-pyrrolidin-1-ylethyl)aniline

A neat mixture of 1-chloro-2-methoxy-4-nitrobenzene (2.0 g, 10.7 mmol) and 2-pyrrolidin-1-ylethanamine (2.5 g, 22 mmol) was heated to 75° C. overnight, then chromatographed on silica gel with ethanol (100%) to give a yellow solid (0.67 g, 24%).

LCMS m/z 266 (MH+). $^1$H NMR (300 MHz, DMSO-d$_6$) δ 7.63 (d, 1H), 7.56 (s, 1H), 6.67 (d, 1H), 6.45 (br, 1H), 3.90 (s, 3H), 3.38 (m, 2H), 2.77 (m, 2H), 2.63 (m, 2H), 2.50 (m, 2H), 1.73 (m, 4H) ppm.

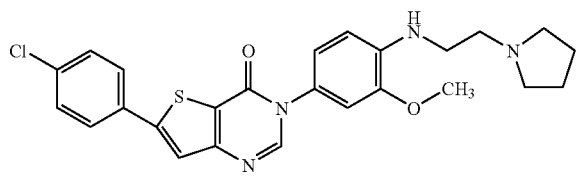

6-(4-chlorophenyl)-3-{3-methoxy-4-[(2-pyrrolidin-1-ylethyl)amino]phenyl}thieno[3,2-d]pyrimidin-4(3H)-one The title compound was prepared from the product of the previous step by procedures analogous to those found in Example H30.

LCMS m/z 481 (MH+).

$^1$H NMR (300 MHz, DMSO-d$_6$) δ 8.40 (s, 1H), 8.00 (s, 1H), 7.95 (d, 2H), 7.60 (d, 2H), 7.00 (s, 1H), 6.95 (d, 1H), 6.60 (d, 1H), 5.10 (t, 1H), 3.80 (s, 3H), 3.20 (m, 2H), 2.69 (m, 2H), 2.50 (m, 4H), 1.70 (m, 4H) ppm.

Examples K21-K23 were prepared through reactions of the title compound of Example K20 with an appropriate acylating reagent.

EXAMPLE K21

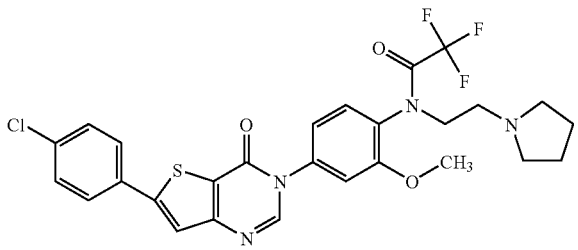

N-{4-[6-(4-chlorophenyl)-4-oxothieno[3,2-d]pyrimidin-3(4H)-yl]-2-methoxyphenyl}-2,2,2-trifluoro-N-(2-pyrrolidin-1-ylethyl)acetamide LCMS m/z 577 (MH+). $^1$H NMR (300 MHz, DMSO-d$_6$) δ 8.40 (s, 1H), 8.00 (s, 1H), 7.95 (d, 2H), 7.60 (d, 2H), 7.00 (s, 1H), 6.95 (d, 1H), 6.60 (d, 1H), 5.10 (t, 1H), 3.80 (s, 3H), 3.20 (m, 2H), 2.69 (m, 2H), 2.50 (m, 4H), 1.70 (m, 4H) ppm.

EXAMPLE K22

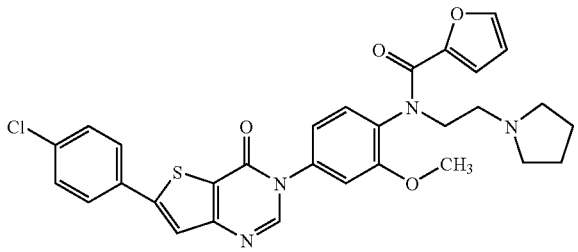

N-{4-[6-(4-chlorophenyl)-4-oxothieno[3,2-d]pyrimidin-3(4H)-yl]-2-methoxyphenyl}-N-(2-pyrrolidin-1-ylethyl)-2-furamide LCMS m/z 575 (MH+). $^1$H NMR (300 MHz, DMSO-d$_6$) δ 8.50 (s, 1H), 8.05 (s, 1H), 7.95 (d, 2H), 7.90 (s, 1H), 7.60 (d, 2H), 7.42 (s, 1H), 7.22 (d, 1H), 7.20 (s, 1H), 6.60 (m, 2H), 4.10 (m, 2H), 3.63 (m, 2H), 3.70 (s, 3H), 2.80 (m, 4H), 1.80 (m, 4H) ppm.

EXAMPLE K23

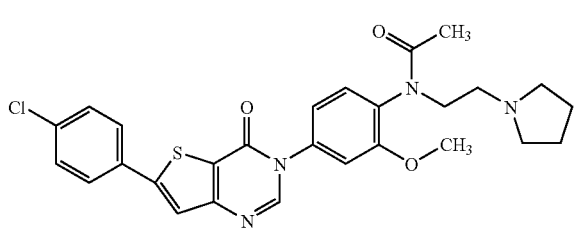

N-{4-[6-(4-chlorophenyl)-4-oxothieno[3,2-d]pyrimidin-3(4H)-yl]-2-methoxyphenyl}-N-(2-pyrrolidin-1-ylethyl)acetamide LCMS m/z 523 (MH+). $^1$H NMR (300 MHz, DMSO-d$_6$) δ 8.50 (s, 1H), 8.05 (s, 1H), 7.95 (d, 2H), 7.60 (d, 2H), 7.50

(s, 1H), 7.42 (d, 1H), 7.22 (d, 1H), 3.90 (t, 2H), 3.80 (s, 3H), 3.38-3.50 (m, 2H), 2.40 (m, 4H), 1.75 (s, 3H), 1.65 (m, 4H) ppm.

EXAMPLE K24

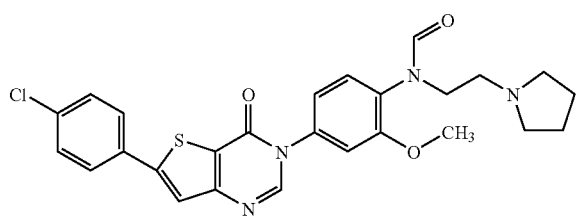

4-[6-(4-Chlorophenyl)-4-oxothieno[3,2-d]pyrimidin-3(4H)-yl]-2-methoxyphenyl(2-pyrrolidin-1-ylethyl)formamide A solution of 6-(4-Chlorophenyl)3-{3-methoxy-4-[(2-pyrrolidin-1-ylethyl)amino]phenyl}thieno[3,2-d]pyrimidin-4(3H)-one (0.050 g, 0.1 mmol) in formic acid (88%, 2 mL) was heated to reflux, concentrated, and then diluted with aqueous sodium hydroxide (0.1N, 2 mL) to precipitate the product as a white solid (0.051 g, 100%). LCMS m/z 509 (MH+). $^1$H NMR (300 MHz, DMSO-$d_6$) δ 8.50 (s, 1H), 8.10 (s, 1H), 8.00 (s, 1H), 7.95 (d, 2H), 7.60 (d, 2H), 7.43 (d, 1H), 7.42 (s, 1H), 7.20 (d, 1H), 3.82 (s, 3H), 3.78 (t, 2H), 3.30-3.50 (m, 2H), 2.40 (m, 4H), 1.70 (m, 4H) ppm.

EXAMPLE K25

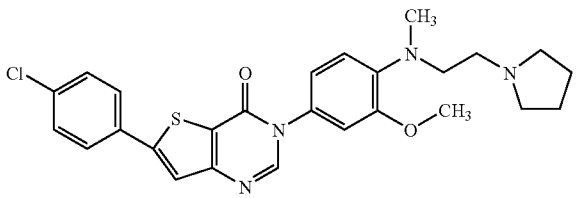

6-(4-Chlorophenyl)-3-{3-methoxy-4-[methyl(2-pyrrolidin-1-ylethyl)-amino]phenyl}thieno[3,2-d]pyrimidin-4(3H)-one The title compound was obtained through treatment of the title compound from Example K20 with the procedures described in Example H18.

LCMS m/z 495 (MH+). $^1$H NMR (300 MHz, DMSO-$d_6$) δ 8.40 (s, 1H), 8.00 (s, 1H), 7.95 (d, 2H), 7.60 (d, 2H), 7.20 (s, 1H), 7.05 (m, 2H), 3.80 (s, 3H), 3.40-3.50 (m, 4H), 3.30 (m, 4H), 2.80 (s, 3H), 1.70 (m, 4H) ppm.

EXAMPLE K26

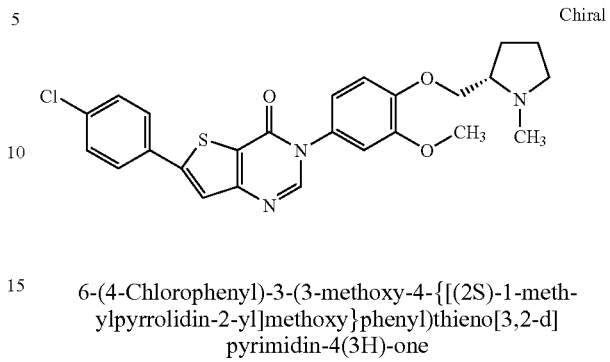

6-(4-Chlorophenyl)-3-(3-methoxy-4-{[(2S)-1-methylpyrrolidin-2-yl]methoxy}phenyl)thieno[3,2-d]pyrimidin-4(3H)-one

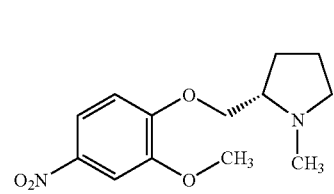

(2S)-2-[(2-methoxy-4-nitrophenoxy)methyl]-1-methylpyrrolidine

A mixture of [(2S)-1-methylpyrrolidin-2-yl]methanol (11.5 g, 0.10 mol), DMF (150 mL) and NaH (4.0 g, 60% in mineral oil, 0.1 mol) was agitated for 30 minutes under an atmosphere of nitrogen. A DMF (100 mL) solution of 1-chloro-2-methoxy-4-nitrobenzene (18.7 g, 0.10 mol) was added and the mixture agitated overnight at RT. The mixture was concentrated, diluted with ethyl acetate, extracted three times with water, dried, filtered, then concentrated to give the product as a tan oil (16.78 g, 63%). LCMS m/z 267 (MH+). $^1$H NMR (300 MHz, DMSO-$d_6$) δ 7.88 (d, 1H), 7.73 (s, 1H), 7.19 (d, 1H), 4.06 (m, 2H), 3.88 (s, 3H), 2.80 (m, 1H), 2.60 (m, 1H), 2.36 (s, 3H), 2.20 (m, 1H). 1.90 (m, 1H), 1.67 (m, 3H) ppm.

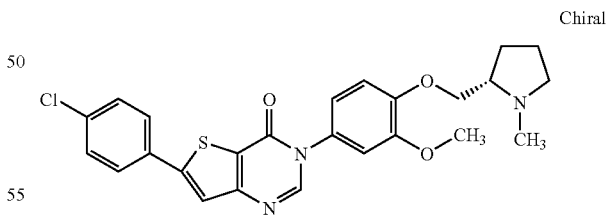

6-(4-Chlorophenyl)-3-(3-methoxy-4-{[(2S)-1-methylpyrrolidin-2-yl]methoxy}phenyl)thieno[3,2-d]pyrimidin-4(3H)-one The title compound was prepared from the product of the previous step by employing procedures analogous to those found in Example H30.

LCMS m/z 482 (MH+). $^1$H NMR (300 MHz, DMSO-$d_6$) δ 8.40 (s, 1H), 8.00 (s, 1H), 7.95 (d, 2H), 7.60 (d, 2H), 7.20

(s, 1H), 7.10 (d, 1H), 7.02 (d, 1H), 3.8-4.10 (m, 2H), 3.80 (s, 3H), 2.95 (t, 1H), 2.60 (m, 1H), 2.40 (s, 3H), 2.20 (q, 1H), 1.95 (m, 1H), 1.50-1.80 (m, 3H) ppm.

EXAMPLE K27

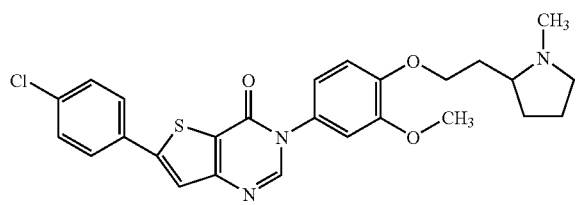

6-(4-Chlorophenyl)-3-{3-methoxy-4-[2-(1-methylpyrrolidin-2-yl)ethoxy]phenyl}thieno[3,2-d]pyrimidin-4(3H)-one

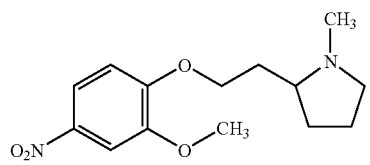

2-[2-(2-methoxy-4-nitrophenoxy)ethyl]-1-methylpyrrolidine

This intermediate was prepared using procedures analogous to those found in Example K26.

LCMS m/z 281 (MH+) ¹H NMR (300 MHz, DMSO-$d_6$) δ 7.88 (d, 1H), 7.75 (s, 1H), 7.19 (d, 1H), 4.18 (t, 2H), 3.88 (s, 3H), 2.90 (m, 1H), 2.20 (s, 3H), 2.10 (m, 2H), 1.60 (m, 2H), 1.90 (m, 1H), 1.67 (m, 3H) ppm.

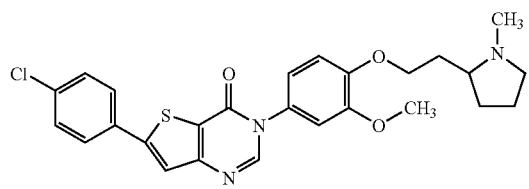

6-(4-Chlorophenyl)-3-{3-methoxy-4-[2-(1-methylpyrrolidin-2-yl)ethoxy]phenyl}thieno[3,2-d]pyrimidin-4(3H)-one The title compound was obtained using procedures analogous to those described in Example K26.

LCMS m/z 496 (MH+). ¹H NMR (300 MHz, DMSO-$d_6$) δ 8.40 (s, 1H), 8.00 (s, 1H), 7.95 (d, 2H), 7.60 (d, 2H), 7.20 (s, 1H), 7.00-7.20 (m, 2H), 4.10 d(t, 2H), 3.80 (s, 3H), 3.00 (m, 3H), 2.20 (s, 3H), 2.10 (m, 1H), 1.97 (m, 1H), 1.70 (m, 4H) ppm.

EXAMPLE K28

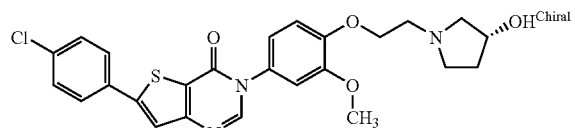

6-(4-Chlorophenyl)-3-(4-{2-[(3R)-3-hydroxypyrrolidin-1-yl]ethoxy}-3-methoxyphenyl)thieno[3,2-d]pyrimidin-4(3H)-one

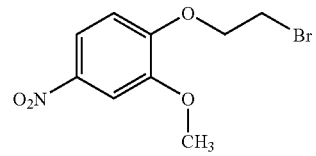

1-(2-bromoethoxy)-2-methoxy-4-nitrobenzene

A mixture of potassium carbonate (27.6 g, 0.2 mol), 2-methoxy-4-nitrophenol (16.9 g, 0.1 mol), 1,2-dibromoethane (94 g, 0.50 mol) and acetonitrile was refluxed for 2 days, concentrated, extracted in ethyl acetate with water three times, dried, filtered, concentrated to a white powder, triturated with ether, filtered, then concentrated to give a pale yellow powder (15.8 g, 58%). ¹H NMR (300 MHz, DMSO-$d_6$) δ 7.90 (d, 1H), 7.80 (s, 1H), 7.20 (d, 1H), 4.55 (t, 2H), 3.80 (s, 3H), 3.75 (t, 2H) ppm.

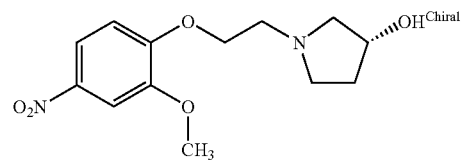

(3R)-1-[2-(2-methoxy-4-nitrophenoxy)ethyl]pyrrolidin-3-ol

A mixture of the product from the preceding step (5.52 g, 0.02 mol), (3R)-pyrrolidin-3-ol (3.48 g, 0.04 mol) and dioxane was mixed at RT overnight, diluted with aqueous NaOH (20 mL, 1N), extracted in ethyl acetate three times with water, dried, filtered and concentrated to a golden viscous oil (3.08 g, 0.011 mol). LCMS m/z 283 (MH+). ¹H NMR (300 MHz, DMSO-$d_6$) δ 7.90 (d, 1H), 7.80 (s, 1H), 7.20 (d, 1H), 4.70 (d, 1H), 4.50 (t, 1H), 4.20 (t, 2H), 3.89 (m, 2H), 3.81 (s, 3H), 2.80 (m, 2H), 2.6 (q, 1H), 2.40 (m, 1H), 1.97 (m, 1H), 1.50 (m, 1H) ppm.

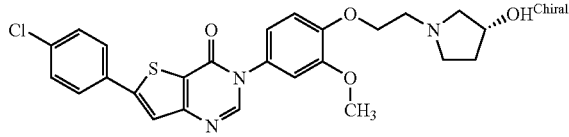

6-(4-Chlorophenyl)-3-(4-{2-[(3R)-3-hydroxypyrrolidin-1-yl]ethoxy}-3-methoxyphenyl)thieno[3,2-d]pyrimidin-4(3H)-one The title compound was obtained from the product of the previous step by employing procedures analogous to those found in Example H30.

LCMS m/z 498 (MH+). $^1$H NMR (300 MHz, DMSO-$d_6$) δ 8.40 (s, 1H), 8.00 (s, 1H), 7.95 (d, 2H), 7.60 (d, 2H), 7.20 (s, 1H), 7.11 (d, 1H), 7.04 (d, 1H), 4.70 (d, 1H), 4.20 (br, 1H), 4.10 (t, 2H), 3.80 (s, 3H), 2.82 (m, 2H), 2.70 (m, 1H), 2.40 (m, 1H), 2.00 (m, 1H), 1.58 (m, 3H) ppm.

EXAMPLE K29

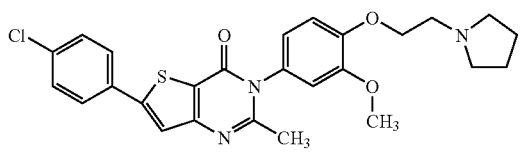

6-(4-Chlorophenyl)-3-[3-methoxy-4-(2-pyrrolidin-1-ylethoxy)phenyl]-2-methylthieno[3,2-d]pyrimidin-4(3H)-one

3-Amino-5-(4-chlorophenyl)-N-[3-methoxy-4-(2-pyrrolidin-1-ylethoxy) phenyl]thiophene-2-carboxamide Aqueous NaOH (4 mL, 1N) was added to a DMSO solution of 6-(4-chlorophenyl)-3-[3-methoxy-4-(2-pyrrolidin-1-ylethoxy)phenyl] thieno[3,2-d]pyrimidin-4(3H)-one (0.50 g, 0.001 mol) at 170° C. After 5 minutes a gummy precipitate was triturated with water and solidified to a tan solid (0.30 g, 60%).

LCMS m/z 472 (MH+). $^1$H NMR (300 MHz, DMSO-$d_6$) δ 9.20 (s, 1H), 7.65 (d, 2H), 7.55 (d, 2H), 7.35 (s, 1H), 7.20 (d, 1H), 7.04 (s, 1H), 6.90 (d, 1H), 6.63 (br s, 2H), 4.00 (t, 2H), 3.75 (s, 3H), 2.75 (t, 2H), 2.55 (m, 4H), 1.65 (m, 4H) ppm.

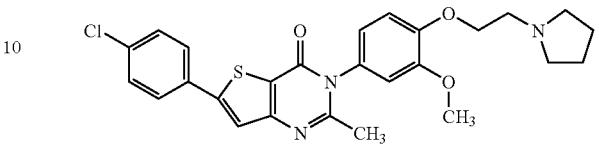

6-(4-Chlorophenyl)-3-[3-methoxy-4-(2-pyrrolidin-1-ylethoxy)phenyl]-2-methylthieno[3,2-d]pyrimidin-4(3H)-one A mixture of 3-amino-5-(4-chlorophenyl)-N-[3-methoxy-4-(2-pyrrolidin-1-ylethoxy) phenyl]thiophene-2-carboxamide and glacial acetic acid was refluxed overnight, concentrated to an amber viscous oil, triturated with water then filtered to give the title compound as its acetic acid salt as a tan solid (0.032 g, 64%). LCMS m/z 496 (MH+). $^1$H NMR (300 MHz, DMSO-$d_6$) δ 8.35 (br, 1H), 8.00 (s, 1H), 7.95 (d, 2H), 7.55 (d, 2H), 7.20 (s, 1H), 7.10 (d, 1H), 6.95 (d, 1H), 4.20 (m, 2H), 3.75 (s, 3H), 2.75 (m, 2H), 2.55 (m, 4H), 2.20 (s, 3H), 2.00 (s, 3H), 1.65 (m, 4H) ppm.

EXAMPLE K30

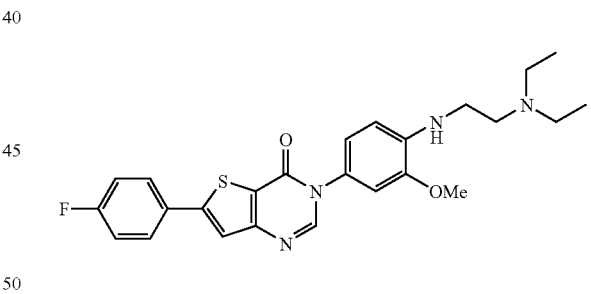

3-(4-{[2-(diethylamino)ethyl]amino})3-methoxyphenyl)-6-(4-fluorophenyl)thieno[3,2-d]pyrimidin-4(3H)-one The title compound was obtained by employing procedures analogous to those described in Example K20.

LCMS m/z=467 (m+H+).

$^1$H NMR (DMSO-D6): δ 8.38 (s, 1H); 7.98 (d, 2H); 7.90 (s, 1H)); 7.38 (d, 2H), 7.00 (s, 1H), 6.95 (d, 1H); 6.62 (d, 1H); 5.20 (t, 1H); 3.80 (s, 3H); 3.25-3.55 (m, 4H); 3.28 (m, 2H); 3.62 (t, 2H); 1.00 (t, 6H).

EXAMPLE K31

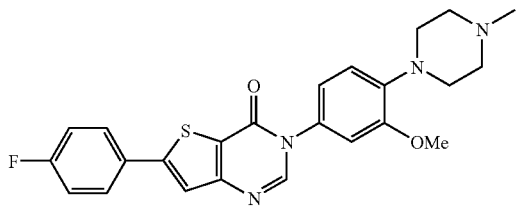

6-(4-Fluorophenyl)-3-[3-methoxy-4-(4-methylpiper-azin-1-yl)phenyl]thieno[3,2-d]pyrimidin-4(3H)-one The title compound was obtained by employing procedures analogous to those described in Example K20.
LCMS m/z=451 (m+H+).
¹H NMR (DMSO-D6): δ 8.40 (s, 1H); 7.98 (d, 2H); 7.90 (s, 1H)); 7.38 (d, 2H), 7.18 (s, 1H), 7.05 (m, 2H); 3.80 (s, 3H); 3.25-3.55 (m, 4H; 3.01 (m, 4H); 2.20 (s, 3H).

EXAMPLE K32

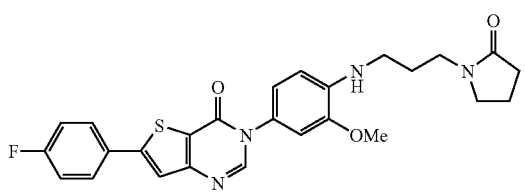

6-(4-Fluorophenyl)-3-(3-methoxy-4-{[3-(2-oxopyr-rolidin-1-yl)propyl]amino}phenyl) thieno[3,2-d]pyrimidin-4(3H)-one The title compound was obtained by employing procedures analogous to those described in Example K20.
LCMS m/z=493 (m+H+).
¹H NMR (DMSO-D6): δ 8.40 (s, 1H); 7.98 (d, 2H); 7.90 (s, 1H)); 7.38 (d, 2H), 7.00 (s, 1H), 6.90 (d, 1H); 6.60 (d, 1H); 5.28 (t, 1H); 3.80 (s, 3H); 3.25-3.55 (m, 4H); 3.12 (q, 2H); 2.20 (t, 2H); 1.95 (qnt, 2H); 1.77 (m, 2H).

EXAMPLE K33

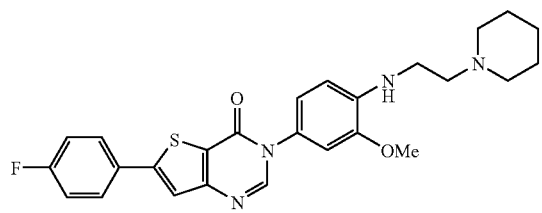

6-(4-Fluorophenyl)-3-{3-methoxy-4-[(2-piperidin-1-ylethyl)amino]phenyl}thieno[3,2-dipyrimidin-4(3H)-one The title compound was obtained by employing procedures analogous to those described in Example K20.
LCMS m/z=479 (m+H+).
¹H NMR (DMSO-D6): δ 8.40 (s, 1H); 7.98 (d, 2H); 7.90 (s, 1H)); 7.38 (d, 2H), 7.00 (s, 1H), 6.95 (d, 1H); 6.62 (d, 1H); 5.20 (t, 1H); 3.80 (s, 3H); 3.25-3.50 (m, 2H); 3.20 (m, 2H); 2.40 (t, 4H); 1.37-1.60 (m, 6H).

EXAMPLE K34

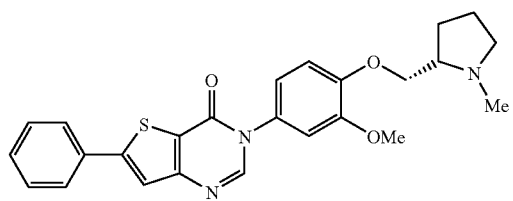

3-(3-Methoxy-4-{[(2R)-1-methylpyrrolidin-2-yl]methoxy}phenyl)-6-phenylthieno [3,2-d]pyrimidin-4(3H)-one The title compound was prepared by employing procedures analogous to those described in Example K26.
LCMS m/z=448 (m+H+).
¹H NMR (DMSO-D6): δ 8.40 (s, 1H); 7.98 (s, 1H); 7.92 (d, 1H)); 7.50 (d, 1H); 7.40-7.60 (m, 3H); 7.20 (s, 1H); 7.10 (d, 1H); 7.05 (d, 1H); 4.02 (m, 1H); 3.90 (m, 1H); 3.80 (s, 3H); 3.00 (m, 1H); 2.60 (m, 1H); 2.40 (s, 3H); 2.20 (q, 1H); 2.00 (m, 1H); 1.65 (m, 2H); 1.60 (m, 1H).

EXAMPLE K35

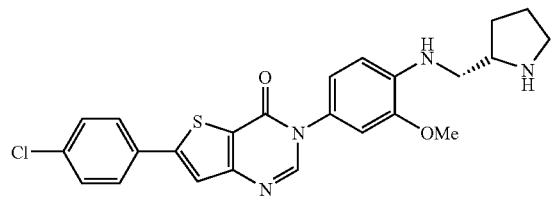

6-(4-Chlorophenyl)-3-(3-methoxy-4-{[(2R)-pyrroli-din-2-ylmethyl]amino}phenyl)thieno[3,2-d]pyrimi-din-4(3H)-one LCMS m/z=467 (m+H+).
¹H NMR (DMSO-D6): δ 8.40 (s, 1H); 7.98 (s, 1H); 7.95 (d, 2H)); 7.60 (d, 2H), 7.08 (s, 1H); 6.98 (d, 1H); 6.78 (d, 1H); 5.60 (m, 1H); 3.83 (s, 3H); 3.10-3.50 (m, 6H); 1.98 (m, 4H).

EXAMPLE K36

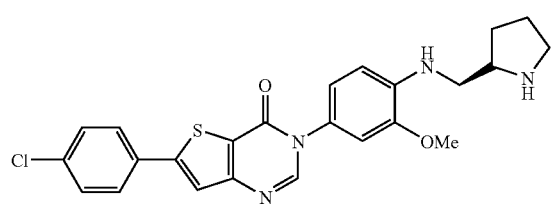

6-(4-Chlorophenyl)-3-(3-methoxy-4-{[(2S)-pyrroli-din-2-ylmethyl]amino}phenyl)thieno[3,2-d]pyrimi-din-4(3H)-one LCMS m/z=467 (m+H+).

¹H NMR (DMSO-D6): δ 8.40 (s, 1H); 7.98 (s, 1H); 7.95 (d, 2H)); 7.60 (d, 2H), 7.08 (s, 1H), 6.98 (d, 1H); 6.78 (d, 1H); 5.60 (m, ₁H); 3.83 (s, 3H); 3.10-3.50 (m, 6H); 1.98 (m, 4H).

EXAMPLE K37

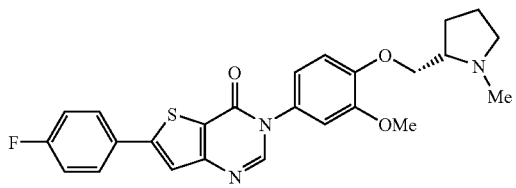

6-(4-Fluorophenyl)-3-(3-methoxy-4-{[(2R)-1-methylpyrrolidin-2-yl]methoxy}phenyl)thieno[3,2-d]pyrimidin-4(3H)-one The title compound was prepared by employing procedures analogous to those described in Example K26.
LCMS m/z=466 (m+H+).
¹H NMR (DMSO-D6) δ 8.40 (s, 1H), 8.00 (d of d, 1H), 7.95 (s, 1H), 7.40 (d of d, 2H), 7.20 (s, 1H), 7.10 (d, 1H), 7.02 (d, 1H), 3.8-4.10 (m, 2H), 3.80 (s, 3H), 2.98 (t, 1H), 2.62 (m,1H), 2.40 (s, 3H), 2.20 (q, 1H), 2.00 (m, 1H), 1.50-1.80 (m, 3H) ppm.

EXAMPLE L1

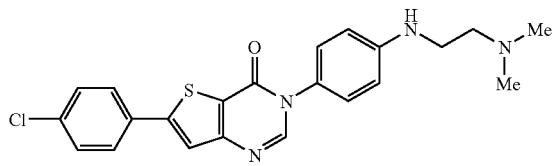

6-(4-chlorophenyl)-3-(4-{[2-(dimethylamino)ethyl]amino}phenyl)thieno[3,2-d]pyrimidin-4(3)-one The title compound was prepared by employing procedures analogous to those described in Example K20.
¹H NMR (DMSO-D$_6$) δ 8.35 (s, 1H), 7.93 (m, 3H), 7.58 (d, 2H, J=8.6 Hz), 7.20 (d, 2H, J=8.7 Hz), 6.70 (d, 2H, J=8.7 Hz), 5.81 (t, 1H, J=5.4 Hz), 3.16 (q, 2H), 2.46 (q, 2H), 2.20 (s, 6H). LCMS m/z=425 (m+H+). Calcd. C, 62.18; H, 4.98; N, 13.18. Found: C, 62.02; H, 4.97; N, 13.06.

EXAMPLE L2

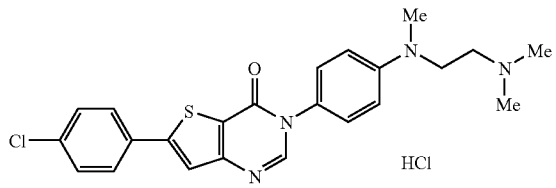

6-(4-chlorophenyl)-3-{4-[[2-(dimethylamino)ethyl](methyl)amino]phenyl}thieno[3,2-d]pyrimidin-4(3H)-one hydrochloride.

The title compound from Example L1 (0.12 g) was dissolved in 88% formic acid (1 mL) and 37% formaldehyde (2 mL). The reaction mixture was refluxed 2 h. The mixture was concentrated on the rotovap to give a white paste. The paste was dissolved in methanol and 1 eq of HCl in dioxane was added. The hydrochloride salt was triturated with ether and filtered to give the product as a solid (0.11 g). ¹H NMR (DMSO-D$_6$) δ 8.37 (s, 1H), 7.99 (m, 3H), 7.58 (d, 2H, J=8.6 Hz), 7.45 (d, 2H, J=8.5 Hz), 6.80 (d, 2H, J=9.0 Hz), 4.93 (s, 2H), 3.98 (m, 2H), 3.81 (m, 2H), 3.28 (s, 6H). LCMS m/z=437 (m+H+).

Examples L3-L5 were prepared by employing procedures analogous to those described in Example K20.

EXAMPLE L3

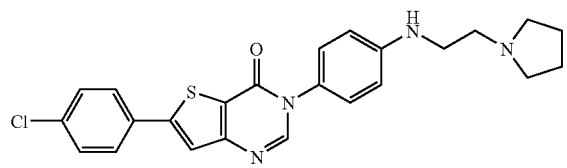

6-(4-chlorophenyl)-3-(4-{[2-(1-pyrrolidinyl)ethyl]amino}phenyl)thieno[3,2-d]pyrimidin-4(3H)-one ¹H NMR (DMSO-D$_6$) δ 8.34 (s, 1H), 7.95 (m, 3H), 7.59 (d, 2H, J=8.6 Hz), 7.20 (d, 2H, J=8.7 Hz), 6.68 (d, 2H, J=8.8 Hz), 5.90 (t, 1H, J=5.4 Hz), 3.19 (q, 2H), 2.63 (q, 2H), 2.51 (s, 4H), 1.71 (s, 4H). LCMS m/z=451 (m+H+). Calcd. C, 63.98; H, 5.14; N, 12.42. Found: C, 63.87; H, 5.18; N, 12.37.

EXAMPLE L4

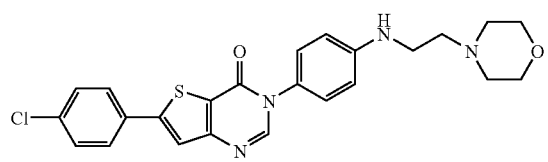

6-(4-chlorophenyl)-3-(4-{[2-(4-morpholinyl)ethyl]amino}phenyl)thieno[3,2-d]pyrimidin-4(3H)-one ¹H NMR (DMSO-D$_6$) δ 8.34 (s, 1H), 7.95 (m, 3H), 7.59 (d, 2H, J=8.6 Hz), 7.20 (d, 2H, J=8.7 Hz), 6.68 (d, 2H, J=8.8 Hz), 5.87 (t, 1H, J=5.4 Hz), 3.60 (m, 4H), 3.19 (q, 2H), 2.52 (m, 2H), 2.50 (m, 4H). LCMS m/z=467 (m+H+). Calcd. C, 61.73; H, 4.96; N, 12.00. Found: C, 61.80; H, 4.96; N, 11.93.

EXAMPLE L5

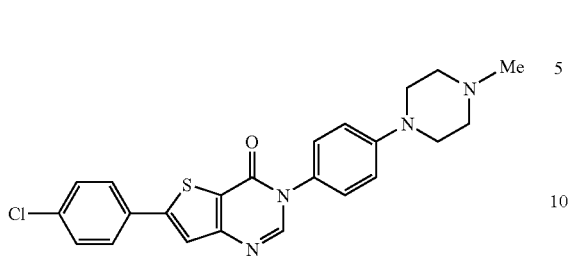

6-(4-chlorophenyl)-3-[4-(4-methyl-1-piperazinyl)phenyl]thieno[3,2-d]pyrimidin-4(3H)-one $^1$H NMR (DMSO-D$_6$) δ 8.38 (s, 1H), 7.98 (m, 3H), 7.60 (d, 2H, J=8.5 Hz), 7.35 (d, 2H, J=8.7 Hz), 7.09 (d, 2H, J=9.0 Hz), 3.22 (m, 4H), 2.50(m, 4H, 2.24 (s, 3H). LCMS m/z=437 (m+H+). Calcd. (0.1 H$_2$O) C, 62.96; H, 4.87; N, 12.77. Found: C, 62.75; H, 4.82; N, 12.55.

EXAMPLE M1

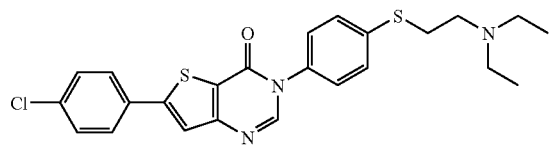

6-(4-chlorophenyl)-3-(4-{[2-(diethylamino)ethyl]sulfanyl}phenyl)thieno[3,2-d]pyrimidin-(3H)-one

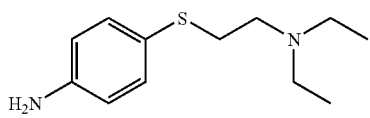

4-{[2-(diethylamino)ethyl]sulfanyl}aniline

To a solution of 4-aminothiophenol (23.0 mmol, 2.88 g) in DMF (23 mL) was added 2-(diethylamino)ethyl chloride hydrochloride (11.5 mmol, 1.98 g) and cesium carbonate (34.5 mmol, 11.2 g). The resulting mixture was heated to 60° C. for 3 hours. The solvent was removed by rotary evaporation. The residue was partitioned between dichloromethane and water. The organic layer was washed with brine, dried over sodium sulfate and concentrated. The residue was purified by flash chromatography eluting with 5% methanol in dichloromethane with 1% triethylamine, giving the title compound (1.26 g, 49%). $^1$H NMR (CDCl$_3$): δ 0.98 (6H, t, J=7.0 Hz), 2.51 (4H, q, J=7.1 Hz), 2.65 (2H, t, J=8.1 Hz), 2.85 (2H, t, J=8.3 Hz), 6.61 (2H, d, J=8.6 Hz), 7.25 (2H, d, J=8.6 Hz). LCMS m/z=225 (m+H+).

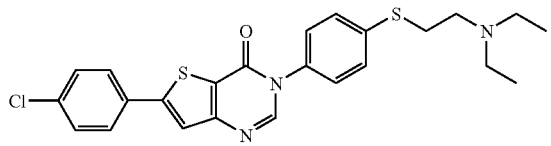

6-(4-chlorophenyl)-3-(4-{[2-(diethylamino)ethyl]sulfanyl}phenyl)thieno[3,2-d]pyrimidin-4(3H)-one The mixture of 4-{[2-(diethylamino)ethyl]sulfanyl}aniline (1.0 mmol, 271 mg), amidine (methyl 5-(4-chlorophenyl)-3-{[(dimethylamino)methylidene]amino]2-thiophenecarboxylate, 1.0 mmol, 322 mg, the preparation of which may be found in the Example J13) and phenol (350 mg) was heated to 190° C. for 20 minutes. The mixture was cooled to room temperature and then washed with methanol. The crude solid product was collected by filtration and then was dissolved in minimum amount of dichlomethane. Adding methanol slowly and let sitting overnight, the title compound was precipitated out as white solid (180 mg, 39%). $^1$H NMR (CDCl$_3$): δ 1.05 (6H, t, J=7.2 Hz), 2.61 (4H, q, J=7.1 Hz), 2.78 (2H, t, J=7.6 Hz), 3.10 (2H, t, J=7.6 Hz), 7.34 (2H, d, J=8.6 Hz), 7.45 (4H, m, overlapping), 7.53 (1H, s), 7.65 (2H, d, J=8.5 Hz), 8.12 (1H, s). LCMS m/z=470 (m+H$^+$).

EXAMPLE M2

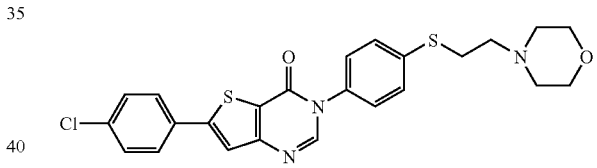

6-(4-chlorophenyl)-3-(4-{[2-(4-morpholinyl)ethyl]sulfanyl}phenyl)thieno[3,2-d]pyrimidin-4(3H)-one Example M2 was prepared according to the procedures described in Example M1.

$^1$H NMR (CDCl$_3$): δ 2.50 (4H, t, J=4.5 Hz), 2.68 (2H, m), 3.12 (2H, m), 3.72 (2H, t, J=4.6 Hz), 7.34 (2H, d, J=8.7 Hz), 7.44 (4H, m, overlapping), 7.52 (1H, s), 7.64 (2H, d, J=8.56 Hz), 8.10 (1H, s). LCMS m/z=484 (m+H$^+$).

EXAMPLE N1

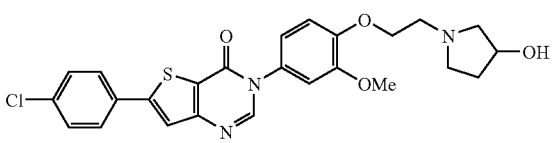

6-(4-chlorophenyl)-3-{4-[2-(3-hydroxypyrrolidin-1-yl)ethoxy]-3-methoxyphenyl}thieno[3,2-d]pyrimidin-4(3H)-one

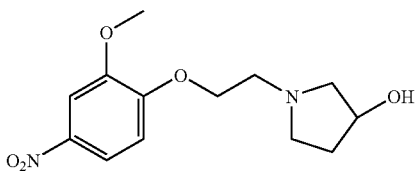

1-[2-(2-methoxy-4-nitrophenoxy)ethyl]pyrrolidin-3-ol 1-(2-Bromoethoxy)2-methoxy-4-nitrobenzene (0.756 g, 2.7395 mmol) 3-pyrrolidinol (0.477 g, 5.479 mmol) and triethylamine (0.554 g, 5.479 mmol) were combined in DMF (10 mL) and heated to 80° C. The reaction was stirred for 2 h. Cooled to RT and diluted with EtOAc (100 mL) and washed with water (2×100 mL). The organics were dried over MgSO$_4$, filtered and concentrated to afford 0.3967 g (1.407 mmol, 51%) of the desired product as a dark brown oil. $^1$H NMR (CDCl$_3$) δ 7.90 (d, 1H, J=9.0 Hz), 7.75 (s, 1H), 6.93 (d, 1H, J=9.0 Hz), 4.38 (m, 1H), 4.24 (t, 2H, J=6.2 Hz), 3.95 (s, 3H), 3.2-3.0 (m, 4H), 3.0-2.90 (m, 1H), 2.8-2.70 (m, 1H), 2.60-2.50 (m, 1H), 2.30-2.20 (m, 1H), 1.85-1.75 (m, 1H).

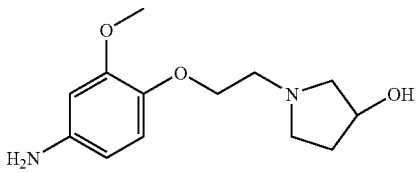

1-[2-(4-amino-2-methoxyphenoxy)ethyl]pyrrolidin-3-ol

1-[2-(2-methoxy-4-nitrophenoxy)ethyl]pyrrolidin-3-ol (0.169 g, 0.583 mmol) was taken up in EtOAc (5 mL) and 10% Pd/C (0.016 g) was added. The hydrogen gas was bubbled through the reaction and the reaction then placed under a hydrogen blanket. Stirred over night. Filtered through celite and concentrated to give 0.118 g (0.470 mmol, 81%) of the desired product. $^1$H NMR (CDCl$_3$) δ 6.74 (d, 1H, J=8.5 Hz), 6.28 (s, 1H), 6.19 (d, 1H, J=8.5 hz), 4.34 (m, 1H), 4.05 (t, 2H, J=6.2 Hz), 3.79 (s, 3H), 3.03-2.83 (m, 5H), 2.63-2.59 (m, 1H), 2.42-2.38 (m, 1H), 2.23-2.14 (m, 1H), 1.75 (m, 1H).

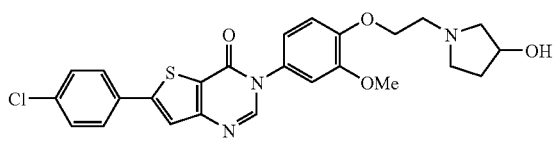

6-(4-chlorophenyl)-3-{4-[2-(3-hydroxypyrrolidin-1-yl)ethoxy]-3-methoxyphenyl}thieno[3,2-d]pyrimidin-4(3H)-one Methyl 3-amino-5-(4-chlorophenyl)thiophene-2-carboxylate (0.126 g, 0.470 mmol) was dissolved in a mixture of DMF (1 mL) and N,N-dimethylformamide dimethylacetal (1 mL) and stirred at 110° C. for 2 h. The mixture was then concentrated to dryness. 1-[2-(4-amino-2-methoxyphenoxy)ethyl]pyrrolidin-3-ol (0.118 g, 0.470 mmol, descibed in the preceding step) in anhydrous ethanol (2 mL) was added and the reaction heated to reflux in an oil bath. The mixture was stirred for 18 h and was then cooled to RT and the precipitate collected and washed with cold ethanol (2×5 mL) to give 0.039 g (0.078 mmol, 17%) of the title compound as an off-white solid.
$^1$H NMR (CDCl$_3$) δ 8.14 (s, 2H), 7.66 (d, 2H, J=8.4 Hz), 7.53 (s, 1H), 7.45 (d, 2H, J=8.4 Hz), 7.02 (d, 1H, 8.3 Hz), 6.93 (m, 2H), 4.39 (m, 1H), 4.24 (t, 2H, J=6.0 Hz), 3.95 (s, 3H), 3.2-3.0 (m, 4H), 3.0-2.90 (m, 1H), 2.8-2.70 (m, 1H), 2.60-2.50 (m, 1H), 2.30-2.20 (m, 1H), 1.85-1.75 (m, 1H). LCMS M+H 498

EXAMPLE N2

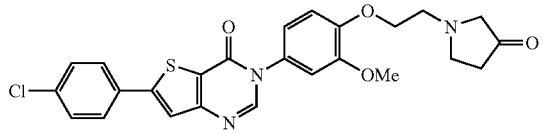

6-(4-chlorophenyl)-3-{3-methoxy-4-[2-(3-oxopyrrolidin-1-yl)ethoxy]phenyl}thieno[3,2-d]pyrimidin-4(3H)-one Oxalyl chloride (0.042 g, 0.33 mmol) was charged to a flask with methylene chloride (2 mL). The reaction was cooled to −78° C. DMSO (0.052 g, 0.67 mmol) was added and the reaction was stirred for 10 min. 6-(4-chlorophenyl)-3-4-[2-(3-hydroxypyrrolidin-1-yl)ethoxy]-3-methoxyphenyl}thieno[3,2-d]pyrimidin-4(3H)-one (0.064 g, 0.13 mmol) in methylene chloride (2 mL) was added to the reaction and stirred for 1 h at -78° C. Triethylamine (0.13 g, 1.29 mmol) was added and the reaction warmed to room temperature. The mix was diluted with methylene chloride (10 mL) and washed with water (2×50 mL). The organics were dried over MgSO$_4$, filtered and concentrated. The resultant residue was purified on a chromatatron (90:10 CH$_2$Cl$_2$:MeOH) to give 0.019 g (0.038 mmol, 30%) of the desired product as a light yellow solid.
$^1$H NMR (CDCl$_3$) δ 8.14 (s, 2H), 7.65 (d, 2H, J=8.5 Hz), 7.53 (s, 1H), 7.44 (d, 2H, J=8.4 Hz), 7.02 (d, 1H, 8.4 Hz), 6.93 (m, 2H), 4.22 (t, 2H, J=6.5 Hz), 3.88 (s, 3H), 3.15 (s, 2H), 3.09-3.05 (m, 4H), 2.43 (t, 2H, J=7.0 Hz).LCMS M+H 497.

EXAMPLE O1

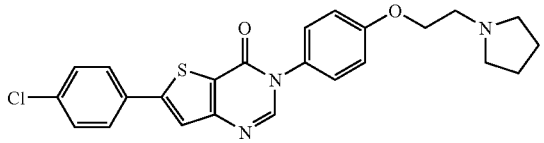

6-(4-chlorophenyl)-3-[4-(2-pyrrolidin-1-ylethoxy)phenyl]thieno[3,2-d]pyrimidin-4(3H)-one A solution of 1-(2-hydroxyethyl)pyrrolidine in THF was added dropwise to a slurry of NaH in THF under N$_2$ at 25°

C. over a 5 min period. The mixture was stirred at 25° C. for 30 min, during which time it turned to a dark amber solution. A solution of 4-nitrofluorobenzene in THF was added dropwise and the resultant mixture was stirred at 25° C. for 48 h. The dark brown solution was carefully quenched by the addition of saturated aqueous NaHCO$_3$ and was diluted with EtOAc. The aqueous layer was extracted with EtOAc (3×) and the combined organic extracts were washed with saturated aqueous NaHCO$_3$, brine (2×) and were dried over MgSO$_4$ and concentrated in vacuo to give a pale amber oil that was used without further purification. A solution of 1-[2-(4-nitrophenoxy)ethyl]pyrrolidine in EtOH under N$_2$ was treated with 10% Pd/C and placed under an atmosphere of H$_2$ via Parr apparatus. The mixture was agitated for 3 h at ~45 psi of hydrogen and was then purged with N$_2$, and filtered through a plug of Celite (EtOAc/EtOH wash) under N$_2$ to give a dark brown oil. Purification of the oil by flash chromatography (12 g pre-packed silica gel ISCO column, 0-15% CH$_3$OH/CH$_2$Cl$_2$) afforded 4-(2-pyrrolidin-1-ylethoxy)aniline as a brown oil. A solution of Methyl 5-(4-chlorophenyl)-3-{[(E)-(dimethylamino)methylidene]amino}2-thiophenecarboxylate (Example J13) and aniline in EtOH under N$_2$ was stirred and heated at reflux for 48 h. The mixture was filtered and the white solid was washed with EtOH and dried in vacuo. Purification by reverse phase chromatography (Gilson, 10-95% acetonitrile/water) and concentration via lyophilization afforded the desired product as a TFA salt. $^1$H NMR (DMSO$_{d6}$) δ 9.80 (br s, 1H), 8.37 (s, 1H), 7.96 (s, 1H), 7.91 (d, J=8.8 Hz, 2H), 7.56 (d, J=8.8 Hz, 2H), 7.50 (d, J=9 Hz, 2H), 7.16 (d, J=9 Hz, 2H), 4.36 (m, 2H), 3.61 (m, 4H), 3.14 (m, 2H), 2.03 (m, 2H), 1.88 (m, 2H). LCMS m/z=452 (M+H).

Examples O2-O6 were prepared through procedures analogous to those described in Example O1.

EXAMPLE O2

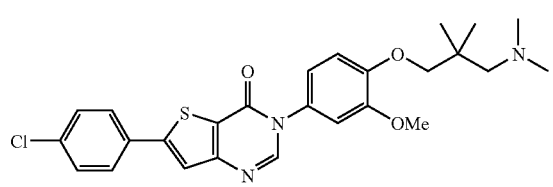

6-(4-Chlorophenyl)-3-{4-[3-(dimethylamino)-2,2-dimethylpropoxy]-3-methoxyphenyl}thieno[3,2-d]pyrimidin-4(3H)-one $^1$H NMR (300 MHz, DMSO-d$_6$) δ 8.39 (s, 1H), 7.97 (s, 1H), 7.92 (d, J=8.7 Hz, 2H), 7.57 (d, J=8.7 Hz, 2H), 7.17 (d, J=2.4 Hz, 1H), 7.09 (d, J=8.6 Hz, 1H), 7.03 (dd, J=8.6, 2.4 Hz, 1H), 3.77 (s, 3H), 3.73 (s, 2H), 2.25 (m, 2H), 2.20 (m, 4H), 0.95 (s, 6H). LCMS m/z 499 (M+H$^+$).

EXAMPLE O3

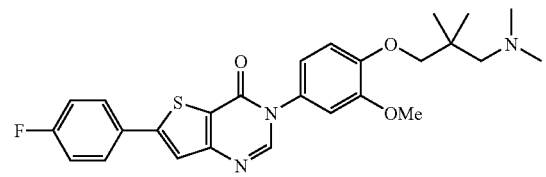

6-(4-Fluorophenyl)-3-{4-[3-(dimethylamino)-2,2-dimethylpropoxy]-3-methoxyphenyl}thieno[3,2-d]pyrimidin-4(3H)-one Characterized as the HCl salt: $^1$H NMR (300 MHz, DMSO-d$_6$) δ 9.23 (br s, 1H), 8.38 (s, 1H), 7.95 (dd, J=8.8, 5.1 Hz, 2H), 7.92 (s, 1H), 7.36 (apparent t, J=8.8 Hz, 2H), 7.23 (d, J=2.3 Hz, 1H), 7.15 (d, J=8.6 Hz, 1H), 7.07 (dd, J=8.6, 2.3 Hz, 1H), 3.94 (s, 3H), 3.80 (br s, 1H), 3.22 (s, 2H), 2.87 (s, 2H), 1.15 (s, 6H). LCMS m/z482 (M+H$^+$).

EXAMPLE O4

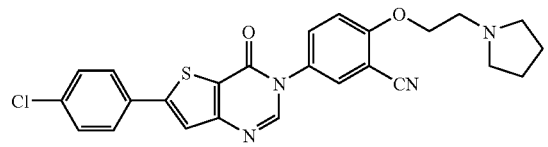

5-[6-(4-Chlorophenyl)-4-oxothieno[3,2-d]pyrimidin-3(4H)-yl]-2-(2-pyrrolidin-1-ylethoxy)benzonitrile Characterized as the HCl salt: $^1$H NMR (300 MHz, DMSO-d$_6$) δ 10.65 (br s, 1H), 8.44 (s, 1H), 8.09 (d, J=2.6 Hz, 1H), 8.00 (s, 1H), 7.93 (obscured d, J=9.2, 1H), 7.57 (d, J=8.7 Hz, 2H), 7.50 (d, J=9.2 Hz, 1H), 4.60 (t, J=4.6 Hz, 2H), 3.71-3.65 (m, 4H), 3.17 (m, 2H), 2.04 (m, 2H), 1.89 (m, 2H). LCMS m/z 477 (M+H$^+$).

EXAMPLE O5

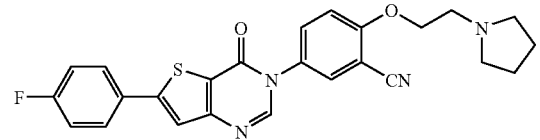

5-[6-(4-Fluorophenyl)-4-oxothieno[3,2-d]pyrimidin-3(4H)-yl]-2-(2-pyrrolidin-1-ylethoxy)benzonitrile Characterized as the HCl salt: $^1$H NMR (300 MHz, DMSO-d$_6$) δ 10.59 (br s, 1H), 8.43 (s, 1H), 8.10 (d, J=2.6 Hz, 1H), 7.96-7.92 (m, 4H), 7.51 (d, J=9.2 Hz, 1H), 7.36 (apparent t, J=8.8 Hz, 2H), 4.60 (t, J=4.6 Hz, 2H), 3.73-3.60 (m, 4H), 3.17 (m, 2H), 2.04 (m, 2H), 1.88 (m, 2H). LCMS m/z461 (M+H$^+$).

EXAMPLE O6

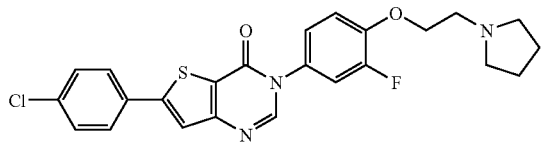

6-(4-Chlorophenyl)-3-[3-fluoro-4-(2-pyrrolidin-1-ylethoxy)phenyl]thieno[3,2-d]pyrimidin-4(3H)-one $^1$H NMR (300 MHz, DMSO-$d_6$) δ 8.40 (s, 1H), 7.97 (s, 1H), 7.92 (d, J=8.5 Hz, 2H), 7.57 (d, J=8.5 Hz, 2H), 7.55 (m, 1H), 7.36-7.32 (m, 2H), 4.22 (t, J=5.7 Hz, 2H), 2.84 (m, 2H), 2.51 (br s, 4H), 1.86 (m, 4H). LCMS m/z 471 (M+H$^+$).

The activity of the compounds used in this invention may be assessed in a functional assay of MCHR1 as follows:

Materials

Black, 96-well, tissue culture-treated plates (#3904) were obtained from Corning Costar, (Cambridge, Mass.), Luc-Plus™ Luciferase Reporter Gene Assay Kit (# 6016969) was from Packard (Meriden, Conn.), plate seals (#097-05-00006) were from Beckman/Sagian (Fullerton, Calif.). DMEM/F12 medium (#11039-021), fetal bovine serum (# 16140-071), L-glutamine (#25030-081), 0.05% trypsin (# 25300-054), G418 (#10131-035) and dPBS (#4190-144) were obtained from Gibco BRL (Gaithersburg, Md.). Thrombin (T7009) was obtained from Sigma Chemical Co (St. Louis, Mo.), MCH peptide (H-1482) was obtained from BaChem California (Torrance, Calif.). Chinese hamster ovary (CHO-K1) cells were obtained from the American Type Culture Collection (Rockville, Md.).

Methods

CHO cells, stably expressing an elkgal4-luc$^+$ reporter gene (host) were transfected by electroporation with the human melanin-concentrating hormone one receptor. A stable clone was selected using G418 for functional antagonist assays. MCH1R-elkgal4-luc$^+$ CHO cells were propagated in complete medium (DMEM/F12, 5% FBS, 2 mM I-glutamine) in T225 flasks. Forty-eight hours prior to assay, cells were harvested with 2 mL of 0.05% trypsin, washed with complete medium and plated at a concentration of 10,000 cells/well in complete medium in black 96-well plates. Eighteen hours prior to the assay, the medium was removed from the cells by aspiration and replaced with 90 μl/well of serum-free DMEM/F12. At the time of the assay, antagonists (1 μL, 100% DMSO) as 10-point concentration curves were pipetted into the medium and plates were incubated for forty-five minutes at 37° C. in a cell culture incubator. Following this incubation, 10 uL of an EC$_{80}$ concentration of MCH was added to the medium and plates were incubated for five hours at 37° C. in a cell culture incubator. The medium was aspirated by vacuum followed by the addition of 50 μl of a 1:1 mixture of LucPlus™ and dPBS/1 mM CaCl$_2$/1 mM MgCl$_2$. The aspiration step was performed in order to avoid potential assay interference by compounds which could inhibit or stimulate luciferase activity or could inhibit light signal. Plates were sealed and subjected to dark adaptation at room temperature for 10 minutes before luciferase activity was quantitated on a TopCount™ microplate scintillation counter (Packard) using 3 seconds/well count time. The ability of the antagonist to inhibit the MCH EC$_{80}$ response was quantified by non-linear regression analysis using a curve-fitting program based in Microsoft ExCel. Specificity of the MCHR1 response was determined using the same protocol by measuring the ability of said antagonists to inhibit an EC$_{80}$ thrombin response (endogenous) in the host cells.

The compounds described in Examples have a pIC$_{50}$ value of greater than 7. For example, the compounds of Examples H1, J1, and I3 have the respective MCHR1 pIC$_{50}$ values shown below.

| Example | MCHR1 pIC$_{50}$ |
| --- | --- |
| H1 | 7.1 |
| J1 | 7.2 |
| I3 | 9.1 |

What is claimed is:
1. A compound of formula (Ia) comprising:

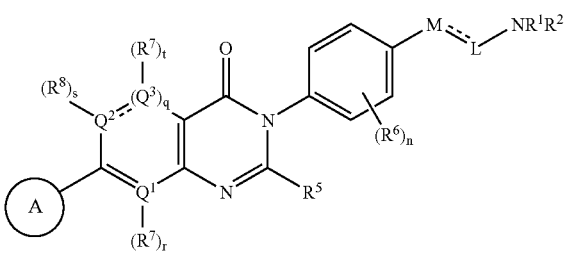

(Ia)

or a pharmaceutically acceptable salt thereof, wherein:
- Ⓐ is aryl, optionally substituted by one to four C$_{1-6}$ straight or branched alkyl, alkenyl, halo, amino, alkylamino, dialkylamino, hydroxy, C$_{1-6}$ alkoxy, cyano, or alkylthio groups;
- a dashed line represents an optional double bond between M and L;
- q and s are 0; r is 1; and t is 0;
- Q$^1$ is C; Q$^3$ is absent;
- Q$^2$ is S;
- R$^8$ is selected from hydrogen, C$_{1-6}$ straight or branched alkyl, C$_{3-6}$ cycloalkyl, C$_{1-6}$, alkoxy, amino, alkylamino, dialkylamino, hydroxy, cyano, alkylthio, and halo;
- R$^7$ is independently selected from the group consisting of hydrogen, C$_{1-6}$ straight or branched alkyl, C$_{3-6}$ cycloalkyl, C$_{1-6}$ alkoxy, amino, alkylamino, dialkylamino, hydroxy, cyano, alkylthio, and halo;
- R$^5$ is selected from the group consisting of hydrogen, and C$_{1-6}$ straight or branched alkyl;
- each R$^6$ is selected from the group consisting of hydrogen, C$_{1-6}$ straight or branched alkyl, C$_{1-6}$ alkoxy, trihaloalkyl, trihaloalkoxy, amino, alkylamino, dialkylamino, hydroxy, cyano, acetyl, alkylthio, and halo; and n is 1 to 4;
- M is selected from the group consisting of O, S, S(O)$_2$, S(O)$_2$NR, N—R, C(O), C(R)$_2$, N—C(O)R, and N—S(O)$_2$R;
- wherein R is selected from the group consisting of hydrogen, phenyl, heteroaryl, C$_{1-6}$ straight or branched alkyl, and C$_{3-6}$ cycloalkyl;
- L is C$_{2-3}$ alkyl, C$_{2-3}$ alkenyl, or —C(O)(CH$_2$)—;
- (i) R$^1$ and R$^2$ each independently are selected from the group consisting of hydrogen, C$_{1-6}$ straight or branched alkyl, C$_{3-6}$ cycloalkyl, and a 5- or 6-membered heterocycle wherein said alkyl, said cycloalkyl and said heterocycle are optionally substituted by phenyl, one to four C$_{1-3}$ alkyl, hydroxy, oxo, alkoxy or halo;

or (ii) $R^1$ and $R^2$ may be selected from the group consisting of aryl and a 5- or 6-membered heteroaryl containing 1, 2, or 3 heteroatoms selected from N, O, and S, wherein said aryl and said heteroaryl are optionally substituted 1, 2, or 3 times with a substituent selected from halo, $C_{1-6}$ straight or branched alkyl, $C_{3-6}$ cycloalkyl, $C_{1-6}$ alkenyl, $C_{3-6}$ cycloalkenyl, hydroxy, $C_{1-6}$ alkoxy, oxo, amino, $C_{1-6}$ alkylamino, $C_{1-6}$ dialkylamino, $C_{1-6}$ alkylthio, $C_{1-6}$ alkylsulfinyl, and phenyl;

or (iii) $R^1$ and $R^2$ together with the nitrogen atom to which they are bonded form a 4-8 membered heterocyclic ring or a 7-11 membered bicyclic heterocyclic ring, each of said 4-8 membered heterocyclic ring and said 7-11 membered bicyclic heterocyclic ring contain 1, 2 or 3 heteroatoms selected from the group consisting of N, O, and S, and wherein either said heterocyclic ring or said bicyclic heterocyclic ring may be optionally substituted by phenyl, one to four $C_{1-3}$ alkyl, hydroxy, $C_{1-3}$ alkoxy oxo, or halo;

or (iv) either $R^1$ or $R^2$ may be independently linked either to the group L or linked to the group M when M is selected from the group consisting of $S(O)_2NR$, N—R, $C(R)_2$, N—C(O)R, and N—S(O)$_2$R, and wherein R is $C_{1-6}$ straight or branched alkyl, to form a 3-7 membered cyclic group which may be optionally substituted by phenyl, one to four $C_{1-3}$ alkyl, hydroxy, alkoxy, oxo, or halo.

2. The compound according to claim 1 wherein said Ⓐ is an aryl substituted with a group selected from the group consisting of halo, $C_{1-3}$ alkyl, and $C_{1-3}$ alkoxy.

3. The compound according to claim 2 wherein said aryl is substituted with a group selected from the group consisting of fluoro, chloro, and methoxy.

4. The compound according to claim 1 wherein L is $C_{2-3}$ alkyl or $C_{2-3}$ alkenyl.

5. The compound according to claim 4 wherein L is $C_{2-3}$ alkyl.

6. The compound according to claim 1, wherein M is selected from the group consisting of O, S, $S(O)_2NR$, N—R, N—C(O)R, and N—S(O)$_2$R.

7. The compound according to claim 6 wherein R is selected from the group consisting of hydrogen, phenyl, $C_{1-6}$ straight or branched alkyl, and $C_{3-6}$ cycloalkyl.

8. The compound according to claim 7 wherein R is selected from the group consisting of hydrogen, $C_{1-6}$ straight or branched alkyl, and $C_{3-6}$ cycloalkyl.

9. The compound according to claim 1 wherein $R^5$ is hydrogen or $C_{1-3}$ alkyl.

10. The compound according to claim 9 wherein $R^5$ is hydrogen or methyl.

11. The compound according to claim 1 wherein $R^6$ is selected from the group consisting of hydrogen, $C_{1-3}$ alkyl, $C_{1-3}$ alkoxy, and halo; and n 1 or 2.

12. The compound according to claim 11 wherein $R^6$ is selected from the group consisting of hydrogen and methoxy; and n is 1.

13. The compound according to claim 1 wherein in (i) above $R^1$ and $R^2$ are selected from the group consisting of hydrogen, $C_{1-6}$ straight or branched alkyl, and $C_{3-6}$ cycloalkyl.

14. The compound according to claim 13 wherein $R^1$ and $R^2$ in (i) are selected from the group consisting of hydrogen, $C_{1-3}$ alkyl, and $C_{3-6}$ cycloalkyl.

15. The compound according to claim 1 wherein in (iii) $R^1$ and $R^2$ together with the nitrogen atom to which they are bonded form a 5- or 6-membered heterocyclic ring or an 8- to 11-membered bicyclic heterocyclic ring having 1 or 2 heteroatoms selected from group N, O, and S, wherein said heterocyclic ring and said bicyclic heterocyclic ring may be optionally substituted up to two times with a substituent selected from the group consisting of oxo and halo.

16. The compound according to claim 1 wherein in (iv) $R^1$ and $R^2$ may be independently linked to the group M when M is selected from the group consisting of $S(O)_2NR$, N—R, $C(R)_2$, N—C(O)R, and N—S(O)$_2$R, and wherein R is $C_{1-6}$ straight or branched alkyl, to form a 5-7 membered cyclic group which may be optionally substituted by phenyl, one to four $C_{1-3}$ alkyl, hydroxy, alkoxy, oxo, or halo.

17. The compound according to claim 1 wherein L is $C_2$-$C_3$ alkyl or $C_2$-$C_3$ alkenyl;
in (i) $R^1$ and $R^2$ are selected from the group consisting of hydrogen, $C_1$-$C_3$ straight or branched alkyl, $C_3$-$C_6$ cycloalkyl substituted with a substituent selected from the group consisting of halo, alkyl, hydroxy, oxo, and alkoxy; or
in (iii) $R^1$ and $R^2$ together with the nitrogen atom to which they are bonded form a 4-6 membered heterocyclic ring wherein said heterocyclic ring is optionally substituted with a substituent selected from the group consisting of one to four $C_1$-$C_3$ alkyl, hydroxy, alkoxy, oxo, and halo.

18. The compound according to claim 17 wherein L is a $C_2$-$C_3$ alkyl;
in (i) $R^1$ and $R^2$ are each independently selected from the group consisting of hydrogen and $C_3$-$C_6$ cycloalkyl substituted with a substituent selected from the group consisting of oxo and halo;
or in (iii) $R^1$ and $R^2$ together with the nitrogen atom to which they are bonded form a 5 or 6 membered heterocyclic wherein said heterocyclic ring is optionally substituted with a substituent selected from the group consisting of one to two oxo and halo.

19. The compound according to claim 18 wherein L is $CH_2CH_2$ and in (iii) $R^1$ and $R^2$ together with the nitrogen atom to which they are bonded form a pyrrolidine ring substituted at the 3-position with a fluorine atom.

20. The compound according to claim 1 wherein M is O, N—R or N—C(O)R where R is hydrogen or $C_1$-$C_6$ straight or branched alkyl and $R^6$ is selected from the group consisting of hydrogen, $C_1$-$C_6$ straight or branched alkyl, $C_1$-$C_3$ alkoxy, trihaloalkyl, trihaloalkoxy, cyano, and halo.

21. The compound according to claim 20 wherein M is O or N—R where R is hydrogen and $R^6$ is selected from the group consisting of hydrogen, $C_1$-$C_2$ straight or branched alkyl, $C_1$-$C_2$ alkoxy, or halo.

22. The compound according to claim 21 wherein M is O and $R^6$ is methoxy.

23. The compound according to claim 1 wherein the compound is selected from the group consisting of 6-(4-chlorophenyl)-3-{3-methoxy-4-[2-(3-oxopyrrolidin-1-yl)ethoxy]phenyl}thieno[3,2-d]pyrimidin-4(3H)-one and 6-(4-chlorophenyl)-3-{4-[2-(3-fluoropyrrolidin-1-yl)ethoxy]-3-methoxyphenyl}thieno[3,2-d]pyrimidin-4(3H)-one.

24. A pharmaceutical composition comprising the compound according to claim 1, or a salt thereof in combination with at least one specie selected from the group consisting of (i) an agent for treating diabetes, (ii) an agent for treating hypertension, and (iii) an agent for treating arteriosclerosis.

25. A pharmaceutical composition comprising a compound of claim 1, and at least one pharmaceutically acceptable component selected from the group consisting of a carrier, a diluent, an excipient, and a mixture thereof.

* * * * *